(12) United States Patent
Ramachandra et al.

(10) Patent No.: US 7,691,370 B2
(45) Date of Patent: *Apr. 6, 2010

(54) SELECTIVITY REPLICATING VIRAL VECTOR

(75) Inventors: Muralidhara Ramachandra, San Diego, CA (US); Paul W. Shabram, Olivehain, CA (US)

(73) Assignee: Canji, Inc., Palo Alto, CA (US)

( * ) Notice: Subject to any disclaimer, the term of this patent is extended or adjusted under 35 U.S.C. 154(b) by 1802 days.

This patent is subject to a terminal disclaimer.

(21) Appl. No.: 10/062,216

(22) Filed: Jan. 30, 2002

(65) Prior Publication Data

US 2002/0150557 A1 Oct. 17, 2002

Related U.S. Application Data

(63) Continuation-in-part of application No. 09/416,812, filed on Oct. 13, 1999, now abandoned.

(60) Provisional application No. 60/104,399, filed on Oct. 15, 1998.

(51) Int. Cl.
*A01N 63/00* (2006.01)
*A61K 35/713* (2006.01)
*A61K 48/00* (2006.01)
*C07H 21/04* (2006.01)
*C12N 15/00* (2006.01)
*C12N 15/12* (2006.01)
*C12N 15/34* (2006.01)

(52) U.S. Cl. .................. 424/93.6; 424/93.1; 435/320.1; 435/325; 536/23.4; 514/44

(58) Field of Classification Search ................ 424/93.1, 424/93.6; 435/320.1, 325; 514/44; 536/23.4
See application file for complete search history.

(56) References Cited

U.S. PATENT DOCUMENTS

| | | | |
|---|---|---|---|
| 5,302,706 A | 4/1994 | Smith | |
| 5,424,400 A | 6/1995 | Smith | |
| 5,648,478 A | 7/1997 | Henderson | |
| 5,677,178 A | 10/1997 | McCormick | |
| 5,698,443 A | 12/1997 | Henderson et al. | |
| 5,801,029 A | 9/1998 | McCormick | |
| 5,837,520 A | 11/1998 | Shabram et al. | |
| 5,846,945 A | 12/1998 | McCormick | |
| 5,856,181 A | 1/1999 | McCormick | |
| 5,886,149 A | 3/1999 | Buckbinder et al. | |
| 5,994,934 A | 11/1999 | Yoshimura et al. | |
| 5,998,205 A * | 12/1999 | Hallenbeck et al. | 435/325 |
| 6,047,850 A | 4/2000 | Matthews | |
| 6,074,850 A | 6/2000 | Antelman et al. | |
| 6,110,735 A | 8/2000 | Chartier et al. | |
| 6,117,911 A | 9/2000 | Grainger et al. | |
| 6,210,939 B1 | 4/2001 | Gregory et al. | |
| 6,281,000 B1 | 8/2001 | Chartier et al. | |
| 6,379,927 B1 | 4/2002 | Antelman et al. | |
| 6,489,305 B1 | 12/2002 | Demers | |
| 6,627,190 B2 * | 9/2003 | Wold et al. | 424/93.2 |
| 6,649,158 B1 * | 11/2003 | LaFace | 424/93.2 |
| 6,689,600 B1 * | 2/2004 | Wu et al. | 435/235.1 |

FOREIGN PATENT DOCUMENTS

| | | |
|---|---|---|
| CA | 2051289 A1 | 3/1992 |
| WO | WO 93/19191 A1 | 9/1993 |
| WO | WO 94/18992 A1 | 9/1994 |
| WO | WO 98/53853 A1 | 7/1995 |
| WO | WO 9519367 * | 7/1995 |
| WO | WO 96/25515 A1 | 8/1996 |
| WO | WO 96/30512 A1 | 10/1996 |
| WO | WO 97/01358 A1 | 1/1997 |
| WO | WO 9725072 * | 7/1997 |
| WO | WO 98/13508 A1 | 4/1998 |
| WO | WO 98/21350 A1 | 5/1998 |
| WO | WO 9821228 A1 * | 5/1998 |
| WO | WO 98/28555 A2 | 7/1998 |
| WO | WO 98/39464 A2 | 9/1998 |

OTHER PUBLICATIONS

Parr et al, Nature Medicine 3(10):1145-1149, 1997.*
Iwase et al, J. Biol. Chem. 272(19):12406-12414, 1997.*
Bett et al, Virus Research 39(1):75-82, 1995; Abstract only.*
Kichina et al, Oncogene 22(31):4911-4917, 2003; Abstract only.*
Zhang, et al., (1994), The requirement of the carboxyl terminus of p53 for DNA binding and transcriptional activation depends on the specific p53 binding DNA element, Oncogene vol. 9, pp. 2513-2521.

(Continued)

*Primary Examiner*—Joseph Woitach
*Assistant Examiner*—Kevin K. Hill
(74) *Attorney, Agent, or Firm*—Townsend and Townsend and Crew LLP

(57) ABSTRACT

The present invention provides recombinant viruses which replicate the viral genome selectively in response to the intracellular conditions of the target cell through the use a pathway-responsive promoter which substantially inhibits viral replication in the host cell based on the phenotypic or genotypic of the infected cell. In the target cell, the promoter element of the pathway-responsive promoter is inactive and thus the virus is permitted to replicate. This results in: (1) killing the cells by natural lytic nature of the virus, and/or (2) provides a therapeutic dose of a transgene product (amplified in comparison to replication incompetent vectors) to the target cell, and (3) producing a localized concentration of the virus facilitating the infection of surrounding cells to the recombinant virus. The invention further provides therapeutic and diagnostic methods of use of the vectors, pharmaceutical formulations comprising the vectors, methods of making the vectors and transformed cells comprising the vectors.

16 Claims, 25 Drawing Sheets

OTHER PUBLICATIONS

Dennier et al. (1998), Direct binding of Smad3 and Smad4 to critical TGFβ-inducible elements in the promoter of human plasminogen activator inhibitor-type 1 gene, The EMBO Journal, vol. 17, No. 11, pp. 3091-3100.

Elsing, et al., (1998), The adenovirus E3/10.K-14.5 K proteins downmodulate the apoptosis receptor Fas/Apo-1 by inducing its internalization, Proceedings of the National Academy Science vol. 95, pp. 10072-10077.

Kim et al., (1996), Replicating viruses as selective cancer therapeutics, Molecular Medicine, pp. 519-527.

Dang et al., Gene therapy and Translational Cancer Therapy, Clinical Cancer Research, vol. 5, pp. 471-474 Feb. 1999.

Eck, S.L. et al., 1996, Ch. 5. Gene Based Therapy, Goodman & Gillman's The Pharmacological Basis of Therapeutics, pp. 77-101ck, et al.

Robbins et al., Review: Viral Vectors for Gene Therapy, Trends in Biotechnology, vol. 16, Jan. 1998, pp. 35-40.

Miller, et al., (1996), Towards the use of replicative adenoviral vectors for cancer gene therapy, Gene Therapy vol. 3, pp. 557-559.

Doronin, et al., (2000), Adenovirus Replication-competent, Tumor-specific Vectors that Overexpress ADP, Academic Press Program No. 5.

Andersson, M. et al., (Nov. 1985), "Impaired Intracellular Transport of Class I MHC Antigen as a Possible Means for Adenoviruses to Evade Immune Surveillance", Cell vol. 43, pp. 215-222.

Burgert, H. et al., (Mar. 1987), "E3/19K" protein of adenovirus type 2 Inhibits lysis of cytolytic T lymphocytes by blocking cell-surface expression of histocompatibility class I antigens, Proceedings of the National Academy of Science (USA) vol. 84, pp. 1356-1360.

Chartier, C. et al., (1996), Efficient Generation of Recombinant Adenovirus Vectors by Homologous Recombination in *Escherchia coli*, Journal of Virology, pp. 4805-4810.

Howe, J. et al., (Aug. 1990), Retinoblastoma growth suppressor and a 300-kDa protein appear to regulate cellular DNA synthesis, Proceedings of the National Academy of Science (USA), vol. 87, pp. 5883-5887.

Prives, C et al., (1999), "The P53 Pathway", J. Pathol vol. 187, pp. 112-126.

Whyte, P. et al., (Jan. 13, 1989), Cellular Targets for Transformation by the Adenovirous E1A Proteins, Cell vol. 56, pp. 67-75.

Verma et al.; (1997), "Gene Therapy-Promises, Problems and Prospects," Nature, vol. 389, pp. 239-242.

Ogawa et al.; (1997),"Novel Combination Therapy for Human Colon Cancer With Adenovirus-Mediated Wild-Type p53 Gene Transfer and DNA Damaging Chemotherapeutic Agent," International Journal of Cancer, vol. 73, pp. 367-370.

Song et. al; (1997), "Sensitization of cis-Platinum by a Recombinant Adenovirus Vector Expressing Wild-Type P53 Gene in Human Ovarian Carcinomas," Oncology Research, vol. 9, pp. 603-609.

Zhang et al.; (1995), "Gene Therapy Strategies for Cancer," Expert Opinion on Investigative Drugs, vol. 4, No. 6, pp. 487-514.

Anderson; (1998), "Human Gene Therapy," Nature vol. 392 (6679 Suppl), pp. 25-30.

Lusky et al.; (1998), "In Vitro and in Vivo Biology of Recombinant Adenovirus Vectors With E1, E1/E2A, or E1/E4 Deleted," Journal of Virology, vol. 72, No. 3, pp. 2022-2032.

Wilson; (1996), "Adenoviruses as Gene-Delivery Vehicles," New England Journal of Medicine, vol. 334, No. 18, pp. 1185-1187.

Egan et al.; (1998), "Mapping of Cellular Protein-Binding Sites on the Products of Early-Region 1A of Human Adenovirus Type 5," Molecular and Cellular Biology, vol. 8, No. 9, pages 3955-3959.

Bernstein; (1998), "Have You Used an Adeno Vector . . . lately?," Nature Genetics, vol. 18, No. 4, pp. 305-306.

Ginsberg et al.; (1989), "Role of Early Region 3 (E3) in Pathogenesis of Adenovirus Disease," PNAS, vol. 86, pp. 3823-3827.

Steegena et al.; (1998) "The Large E1B Protein Together With the E4orf6 Protein Target p53 for Active Degradation in Adenovirus Infected Cells," Oncogene, vol. 16, No. 3, pp. 349-357.

Raper et al.; (1998), "Selective Gene Transfer Into the Liver of Non-Human Primates With E1-Deleted, E2A-Defective, or E1-E4 Deleted Recombinant Adenoviruses," Human Gene Therapy, vol. 9, No. 5, pp. 671-679.

Russell et al.; (1998), "Human Gene Targeting by Viral Vectors," Nature Genetics, vol. 18, pp. 625-330.

Vile et al.; (1998), "Strategies for Achieving Multiple Layers of Selectivity in Gene Therapy," Molecular Medicine Today, vol. 4, No. 2, pp. 84-92.

Gemma et al.; (1998), "hSmad5 gene, a Human hSmad Family Member: Its Full Length cDNA, Genomic Structure, Promoter Region and Mutation Analysis In Human Tumors", Oncogene, vol. 7, pp. 951-956.

Bayley et al.; (1994), "Adenovirus E1A Proteins and Transformation (Review)," International Journal of Oncology, vol. 5, No. 3, pp. 425-444.

Deonarain et al.; (1995), "Genetic Delivery of Enzymes for Cancer Therapy," Gene Therapy, vol. 2, No. 4, pp. 235-244.

Jelsma et al.; (1998), "Sequences in E1A Proteins of Human Adenovirus 5 Required for Cell Transformation, Repression of a Transcriptional Enhancer, and Induction of Proliferating Cell Nuclear Antigen," Virology, vol. 171, No. 1, pp. 120-130.

Howe et al.; (1992), "Effects of Ad5 E1A Mutant Viruses on the Cell Cycle in Relation to the Binding of Cellular Proteins Including the Retinoblastoma Protein and Cyclin A," Virology, vol. 186, No. 1, pp. 15-24.

Horowitz; (1990), "Adenoviridae and Their Replication," Virology, ed. Fields et al., vol. 2, 2nd ed., New York, NY: Raven Press, pp. 1679-1721.

Jones et al.; (1979), "An Adenovirus Type 5 Early Gene Function Regulates Expression of Other Early Viral Genes," PNAS, vol. 76, No. 8, pp. 3665-3669.

Chang et al.; (1995), "Cystostatic Gene Therapy for Vascular Proliferative Disorders With a Constitutively Active Form of the Retinoblasatoma Gene Product,"Science, vol. 267, No. 5197, pp. 518-522.

Jelsma et al.; (1988), "Use of Deletion and Point Mutants Spanning the Coding Region of the Adenovirus 5 E1A Gene to Define a Domain That is Essential for Transcriptional Activation," Virology, vol. 163, No. 2, pp. 494-502.

Kim et al.; (1998), "Requirement for Specific Proteases in Cancer Cell Intravasation as Revealed by a Novel Semiquantitative PCR-Based Assay," Cell, vol. 94, No. 3, pp. 353-362.

Smth et al.; (1994), "Interaction of the p53-Regulated Protein Gadd45 with Proliferating Cell Nuclear Antigen," Science, vol. 266, No. 5189, pp. 1376-1380.

Hiyoshi et al.; (1992), "Clinicopathological Significance of Nuclear Accumulation of Tumor Suppresor Gene p53 Product in Primary Lung Cancer," Japanese Journal of Cancer Research, vol. 83, No. 1, pp. 101-106.

Chen et. al; (1991), "Expression of Wild-type p53 in Human A673 Cells Suppresses Tumorigenicity But Not Growth Rate," Oncogene, vol. 6, No. 10, pp. 1799-1805.

Russ et. al; (1996), "Self-Deleting Retrovirus Vectors for Gene Therapy," Journal of Virology, vol. 70, No. 8, pp. 4927-4932.

Lachmann et al.; (1997), "Utilization of the Herpes Simplex Virus Type 1 Latency-Associated Regulatory Region to Drive Stable Reporter Gene Expression in the Nervous System," Journal of Virology, vol. 71, No. 4, pp. 3197-3207.

Grodzicker et al.; (1980), "Expression of Unselected Adenovirus Genes in Human Cells Co-Transformed With the HSV-1 tk Gene and Adenovirus 2 DNA," Cell, vol. 21, No. 2, pp. 453-463.

Wersto et al.; (1998), "Recombinant, Replication-Defective Adenovirus Gene Transfer Vectors Induce Cell Cycle Dysregulation and Inappropriate Expression of Cyclin Proteins," Journal of Virology, vol. 72, No. 12, pp. 9491-9502.

Roth; (1999), "Snapshots of ARF1: Implications for Mechanisms of Activation and Inactivation," Cell, vol. 97, No. 2, pp. 149-152.

Shenk; (1996), "Adenoviridae: The Viruses and Their Replication," Fields Virology, ed. Fields et al., 3rd ed., Philadelphia, PA: Lippencott-Raven Publishers, pp. 2111-2148.

Vile et al.; (1994), "Gene Transfer Technologies For the gene Therapy of Cancer," Gene Therapy, vol. 1, No. 2, pp. 88-98.

Friedmann; (1992), "A Brief History of Gene Therapy," *Nature Genetics*, vol. 2, No. 2, pp. 93-98.
Gluzman et al.; (1982), "Helper-Free Adenovirus Type 5 Vectors," *Eukaryotic Viral Vectors*, ed. Y. Gluzman, Cold Spring Harbor, NY: Cold Spring Harbor Laboratory Press, pp. 187-192.
Newman; (1954), "Virus Treatment in Advanced Cancer; A Pathological Study of Fifty-Seven Cases," *Cancer*, vol. 7, No. 1, pp. 106-118.
Momand et al.; (1992), "The mdm-2 Oncogene Product Forms a Complex With the p53 Protein and Inhibits p53-Mediated Transactivation," *Cell*, vol. 69, No. 7, pp. 1237-1245.
Mietz et al.; (1992), "The Transcriptional Transactivation Function of Wild-Type p53 Is Inhibited by SV40 Large T-antigen and by HPV-16 E6 Oncoprotein," *The EMBO Journal*, vol. 11, No. 13, pp. 5013-5020.
Graham et al.; (1991), "Manipulation of Adenovirus Vectors," *Methods in Molecular Biology*, vol. 7, ed. E. J. Murray, Clifton, NJ: The Humana Press Inc., pp. 109-128.
Phelps et al.; (1992), "Structure-Function Analysis of the Human Papillomavirus Type 16-E7 Oncoprotein," *Journal of Virology*, vol. 66, No. 4, pp. 2418-2427.
Brokaw et al.; (1994), "A Mutational Analysis of the Amino Termainal Domain of the Human Papillomavirus Type 16 E7 Oncoprotein," *Virology*, vol. 205, No. 2, pp. 603-607.
Maxwell et al.; (1986), "Regulated Expression of a Diphtheria Toxin A-Chain Gene Transfected Into Human Cells: Possible Strategy for Inducing Cancer Cell Suicide," *Cancer Research*, vol. 46, No. 9, pp. 4660-4664.
Martuza et al.; (1991), "Experimental Therapy of Human Glioma by Means of Genetically Engineered Virus Mutant," *Science*, vol. 252, No. 5007, pp. 854-856.
Cote et. al; (1991), "Genetic Alterations of the p53 Gene Are a Feature of Malignant Mesotheliomas," *Cancer Research*, vol. 51, No. 19, pp. 5410-5416.
Maxwell et al.; (1993), "Binding of Cellular Protiens to a Conformational Domain of Tumor Suppressor Protein p53," *Oncogene*, vol. 8, No. 12, pp. 3421-3426.
Iwabuchi et al.; (1994), "Two Cellular Proteins That Bind to Wild-Type But Not Mutant p53," *PNAS*, vol. 91, No. 13, pp. 6098-6102.
Hamel et al.; (1992), "Transcriptional Repression of the E2-Containing Promoter EllaE, c-myc, and RB1 by the Product of the RB1 Gene," *Molecular and Cellular Biology*, vol. 12, No. 8, pp. 3431-3438.
Crook et al.; (1991), "Degradation of p53 Can Be Targeted by HPV E6 Sequences Distinct From Those Required for p53 Binding and Trans-Activation," *Cell*, vol. 67, No. 3, pp. 547-556.
Takimoto et al.; (1994), "Identification of Cellular Proteins That Bind the Central Conserved Region of p53," *Biochemical and Biophysical Research Communications*, vol. 202, No. 1, pp. 490-496.
Chen et. al; (1994), "Hot-spot p53 Mutants Interact Specifically With Two Cellular Proteins During Progression of the Cell Cycle," *Molecular and Cellular Biology*, vol. 14, No. 10, pp. 6764-6772.
Barak et al.; (1992), "Enhanced Binding of 95 kDa Protein to p53 in Cells Undergoing p53-Mediated Growth Arrest," *The EMBO Journal*, vol. 11, No. 6, pp. 2115-2121.
Truant et al.; (1993), "Direct Interaction Between the Transcriptional Activation Domain of Human p53 and the TATA Box-Binding Protein," *Journal of Biological Chemistry*, vol. 268, No. 4, pp. 2284-2287.
Velcich et al.; (1988), "Adenovirus E1a ras Cooperation Activity is Separate From Its Positive and Negative Transcription Regulatory Functions," *Molecular and Cellular Biology*, vol. 8, No. 5, pp. 2177-2183.
Subramanian et al.; (1995), "p53-independent Apoptotic and Necrotic Cell Deaths Induced by Adenovirus Infection: Suppression by E1B 19K and Bcl-2 Proteins," *Cell Growth & Differentiation*, vol. 6, no. 2, pp. 131-137.
Barker et al.; (1987), "Adenovirus Proteins From Both E1B Reading Frames are Required for Transformation of Rodent Cells by Viral Infection and DNA Transfection," *Virology*, vol. 156, No. 1, pp. 107-121.

Mak et al.; (1990), "Separate Regions of an Adenovirus E1B Protein Critical for Different Biological Fucntions," *Virology*, vol. 176, No. 2, pp. 553-562.
Horowitz; (1985), "Adenoviral Diseases," *Virology*, ed. B. N Fields, New York, NY: Raven Press, pp. 477-495.
Bjorn et al.; (1990), "Selective elemination of Breast Cancer Cells from Human Bone Marrow Using an Antibody-Pseudomonas Exotoxin A Conjugate," *Cancer Research*, vol. 50, No. 18, pp. 5992-5996.
Shepherd et al.; (1993), "Induction of the Cell Cycle in Baby Rat Kidney Cells by Adenovirus Type 5 E1A in the Absence of E1B and a Possible Influence of p53," *Journal of Virology*, vol. 67, No. 5, pp. 2944-2949.
Shingu et al.; (1991), "Therapeutic Effects of Bovine Enterovirus Infection on Rabbits With Experimentally Induced Adult T Cell Leukaemia," *Journal of General Virology*, vol. 72, pt. 8, pp. 2031-2034.
Huebner et al.; (1956), "Studies on the Use of Viruses in the Treatment of Carcinoma of the Cervix," *Cancer*, vol. 9, No. 6, pp. 1211-1218.
Von Hoff et al.; (1998), "Advances in the Treatment of Patients With Pancreatic Cancer: Improvements in Symptoms and Survival Time," *British Journal of Cancer*, vol. 78, Suppl. 3, pp. 9-13.
Bernards et al.; (1986), "Role of Adenovirus Early Region 1B Tumor Antigens in Transformation and Lytic Infection," *Virology*, vol. 150, No. 1, pp. 126-139.
Osborne et al.; (1982), "The TATA Homology and the mRNA 5' Untranslated Sequence Are Not Required for Expression of Essential Adenovirus E1A Functions," *Cell*, vol. 29, No. 1, pp. 139-148.
Nevins; (1981), "Mechanism of Activation of Early Viral Transcription by the Adenovirus E1A Gene Product," *Cell*, vol. 26, pp. 213-220.
Curtois et al.; (1984), "Adenovirus E1A Protein Activation of an Integrated Viral Gene," *The EMBO Journal*, vol. 3, No. 5, pp. 1145-1149.
Dion et al.; (1996), "E1A RNA Transcripts Amplify Adenovirus-Mediated Tumor Reduction," *Gene Therapy*, vol. 3, No. 11, pp. 1021-1025.
Kim et al.; (1998), "Onyx-015: Clinical Data Are Encouraging," *Nature Medicine*, vol. 4, No. 12, pp. 1341-1342.
Rothmann et. al; (1998), "Replication of Onyx-015, a Potential Anticancer Adenovirus, Is Independent of p53 Status in Tumor Cells," *Journal of Virology*, vol. 72, No. 12, pp. 9470-9478.
Rittner et al.; (1997), "Conditional Repression of the E2 Transcription Unit in E1-E3-Deleted Adenovirus Vectors is Correlated With a Strong Reduction in Viral DNA Replication and Late Gene Expression in Vitro," *Journal of Virology*, vol. 71, No. 4, pp. 3307-3311.
Heise et al.; (1997), "Onyx-015, An E1B Gene-Attenuated Adenovirus, Causes Tumor-Specific Cytolysis and Antitumoral Efficacy That Can Be Augmented by Standard Chemotherpeutic Agents," *Nature Medicine*, vol. 3, No. 6, pp. 639-645.
Hall et al.; (1998), "p-53-Dependent Cell Death/Apoptosis Is Required for a Productive Adenovirus Infection," *Nature Medicine*, vol. 4, No. 9, pp. 1068-1072.
Goodrum; (1998), "p53 Status Does Not Determine Outcome of E1B 55-Kilodalton Mutant Adenovirus Lytic Infection," *Journal of Virology*, vol. 72, No. 12, pp. 9479-9490.
Bischoff et al.; (1996), "An Adenovirus Mutant That Replicates Selectively in p-53-Deficient Human Tumor Cells," *Science*, vol. 274, No. 5286, pp. 373-376.
Turnell et al.; (1999), "The Replicative Capacities of Large E1B-Null Group A and Group C Adenoviruses Are Independent of Host Cell p53 Status," *Journal of Virology*, vol. 73, No. 3, pp. 2074-2083.
Ridgway et al.; (1997), "p53/E1b58kDa Complex Regulates Adenovirus Replication," *Virology*, vol. 237, No. 2, pp. 404-413.
Hay et al.; (1999), "Targeting the Replication of Adenoviral Gene Therapy Vectors to Lung Cancer Cells: The Importance of the Adenoviral E1b-55kD Gene,"0 *Human Gene Therapy*, vol. 10, No. 4, pp. 579-590.
Querido et al.; (1997), "Regulation of p53 Levels by the E1B 44-Kilodalton Protein and E4orf6 in Adenovirus-infected Cells," *Journal of Virology*, vol. 71, No. 5, pp. 3788-3798.

Herbst et al.; (1988), "Regulation of Adenovirus and Cellular Gene Expression and of Cellular Transformation by the E1B-Encoded 175-Amino-Acid Protein," *Journal of Virology*, vol. 62, No. 12, pp. 4634-4643.

Yew et al.; (1990), "Dissection of Functional Domains in the Adenovirus 2 Early 1B 55k Polypeptide by Suppressor-Linker Insertional Mutagenesis," *Virology*, vol. 179, No. 2, pp. 795-805.

Sabramanian et al.; (1986), "Separation of the Functions Controlled by Adenovirus 2Ip+ Locus," *Virology*, vol. 150, No. 2, pp. 381-389.

Pilder et al.; (1986, "The Adenovirus E1B-55k Transforming Polypeptide Modulates Transport or Cytoplasmic Stabilization of Viral and Host Cell mRNAs," *Molecular and Cellular Biology*, vol. 6, No. 2, pp. 470-476.

Moore; (1954), "Effects of Viruses on Tumors," *Annual Review of Microbiology*, vol. 8, pp. 393-410.

Orkin et al.; (1995), *Report and Recommendations of the Panel to Assess the NIH Investment in Research on Gene Therapy*, 39 pages.

Jones et al.; (1979), "Isolation of Adenovirus Type 5 Host Range Deletion Mutant Defective for Transformation of Rat Embryo Cells," *Cell*, vol. 17, No. 3, pp. 683-689.

Jones et al.; (1978), "Isolation of Deletion and Substitution Mutants of Adenovirus Type 5," *Cell*, vol. 13, No. 1, pp. 181-188.

Thummel et al.; (1981), "Expression of SV40 T Antigen Under Control of Adenovirus Promoter," *Cell*, vol. 23, No. 3, pp. 825-836.

Solnick; (1981), "Construction of an Adenovirus-SV40 Recombinant Producing SV40 T Antigen From an Adenovirus Late Promoter," *Cell*, vol. 24, No. 1, pp. 135-143.

Berk et. al; (1979), "Pre-Early Adenovirus 5 Gene Product Regulates Synthesis of Early Viral Messenger RNAs," *Cell*, vol. 17, No. 4, pp. 935-944.

Chang et al.; (1993), "Tumourigenesis Associated With the p53 Tumour Suppressor Gene," *British Journal of Cancer*, vol. 68, No. 4, pp. 653-661.

Barbeau et al.; (1994), "Functional Interactions within Adenoviruses E1A Protein Complexes," *Oncogene*, vol. 9, No. 2, pp. 359-373.

Graham; (1984), "Transformation by and Oncogenicity of Human Adenoviruses," *The Adenoviruses*, ed. H. S. Ginsberg, New York, NY: Plenum Press, pp. 339-398.

Mulligan; (1993), "The Basic Science of Gene Therapy," *Science*, vol. 260, No. 5110, pp. 926-932.

* cited by examiner

US 7,691,370 B2

SELECTIVITY REPLICATING VIRAL VECTOR

RELATION TO OTHER APPLICATIONS

The present application is a Continuation-in-Part of U.S. patent application Ser. No. 09/416,812 filed Oct. 13, 1999 now abandoned and claims the benefit of this application in accordance with 35 U.S.C. 120. This application also claims the benefit of U.S. Provisional Application Ser. No. 60/104,399 filed Oct. 15, 1998 pursuant to 35 U.S.C. 119.

BACKGROUND OF THE INVENTION

Recombinant adenoviruses are currently used for the delivery of therapeutic transgenes in a variety of therapeutic regimens. However, the broad range of infectivity of these vector systems has raised concerns that the expression of the virus in non-tumor cells might cause collateral damage to non-neoplastic cells. Consequently, a broad range of targeting systems have been developed to preferentially express the transgene in a given cell type. Tissue specific and tumor specific promoters have been employed to preferentially replicate the vector in certain cell types. For example, International Patent Application No. PCT/US96/10838 published Jan. 16, 1997 (International Publication No. WO97/01358) describes the use of vectors which replicate in a specific host cell by the use of prostate specific promoter elements driving the E1, E2 or E4 functions, optionally containing a cytotoxic transgene expression cassette. In particular, this publication describes a construct where prostate specific enhancer controls expression of E1 and has a expression cassette comprising the CMV-promoter driving expression of the cytosine deaminase gene which is inserted into the E3 region. These vectors are replication competent and are capable of packaging into intact virions in a particular cell type.

An alternative approach to the use of tumor specific promoters to drive viral replication is to employ specific deletions in the adenoviral E1b 55K protein coding sequence. Recombinant adenoviruses which contain defects in the nucleotide sequence encoding E1b 55K are described in U.S. Pat. No. 5,677,178 issued Oct. 14, 1997. However, these tissue or tumor specific control elements have been observed to be "leaky", i.e. permitting replication in cell types other than the preferred target cells.

Alternative to this type of selectively replicating vector is the employment of a replication deficient adenoviral vector containing extensive elimination of E1 function. In particular, vectors containing elimination of E1, E2 E3 and partial E4 deletions have been employed to delivery exogenous transgenes. Such vectors have been employed to deliver the p53 gene to target cells. It has been demonstrated that the expression of an exogenously administered wild type p53 in a p53 deficient (p53 mutated or p53 null) tumor cell is capable of inducing p53 mediated apoptosis in the tumor cell. Such viral vectors for the delivery of p53 are currently under development Schering Corporation and Introgen Corporation. Again these vectors have demonstrated acceptable toxicology profiles and therapeutic efficacy for human therapeutic applications and are in Phase II clinical trials in man for the treatment of p53 related malignancies.

Replication deficient and selectively replicating vectors have, at least in theory, design drawbacks which are of concern to clinicians. Because replication deficient vectors will not propagate uncontrollably in the patient, they theoretically have a more appealing safety profile. However, as effective tumor elimination requires the infection of the substantial majority of the tumor cells being infected, a substantial molar excess of vector is commonly used to insure therapeutic effectiveness. Selectively replicating vectors are viewed as being more of an issue from a safety perspective because of their ability to replicate and potentially mutate to form fully replication competent vectors in the patient. However, by maintaining the natural ability to the virus to propagate under particular conditions enables these vectors to spread to surrounding tumor cells. Since the vectors themselves are able to replicate, a lower initial dose of such vectors is required. This is favorable from an immunological perspective as well as for economic reasons in the manufacture of such agents. Therefore, there is a need in the art for a selectively replicating vector which addresses the perceived safety problems while providing the increased therapeutic index.

The present invention solves these problems by providing a selectively replicating adenoviral vector containing a pathway targeted pathway-responsive promoter driving expression of a repressor of viral replication such that the vector replicates preferentially in cells defective in the pathway. The present invention also provides pharmaceutical formulations comprising such vectors. The present invention also provides methods of eliminating pathway defective cells from a population of normal cells by using such vectors.

SUMMARY OF THE INVENTION

The present invention provides recombinant viruses which replicate the viral genome selectively in response to the intracellular conditions of the target cell through the use a pathway-responsive promoter driving expression of an inhibitor of viral replication which substantially inhibits viral replication in the host cell based on the phenotypic or genotypic of the infected cell. In the target cell, the promoter element of the pathway-responsive promoter is inactive and thus the virus is permitted to replicate. This results in: (1) killing the cells by natural lytic nature of the virus, and/or (2) provides a therapeutic dose of a transgene product (amplified in comparison to replication incompetent vectors) to the target cell, and (3) producing a localized concentration of the virus facilitating the infection of surrounding target cells to the recombinant virus. The invention further provides therapeutic and diagnostic methods of use of the vectors, pharmaceutical formulations comprising the vectors, methods of making the vectors and transformed cells comprising the vectors.

DETAILED DESCRIPTION OF THE INVENTION

Figure 1:
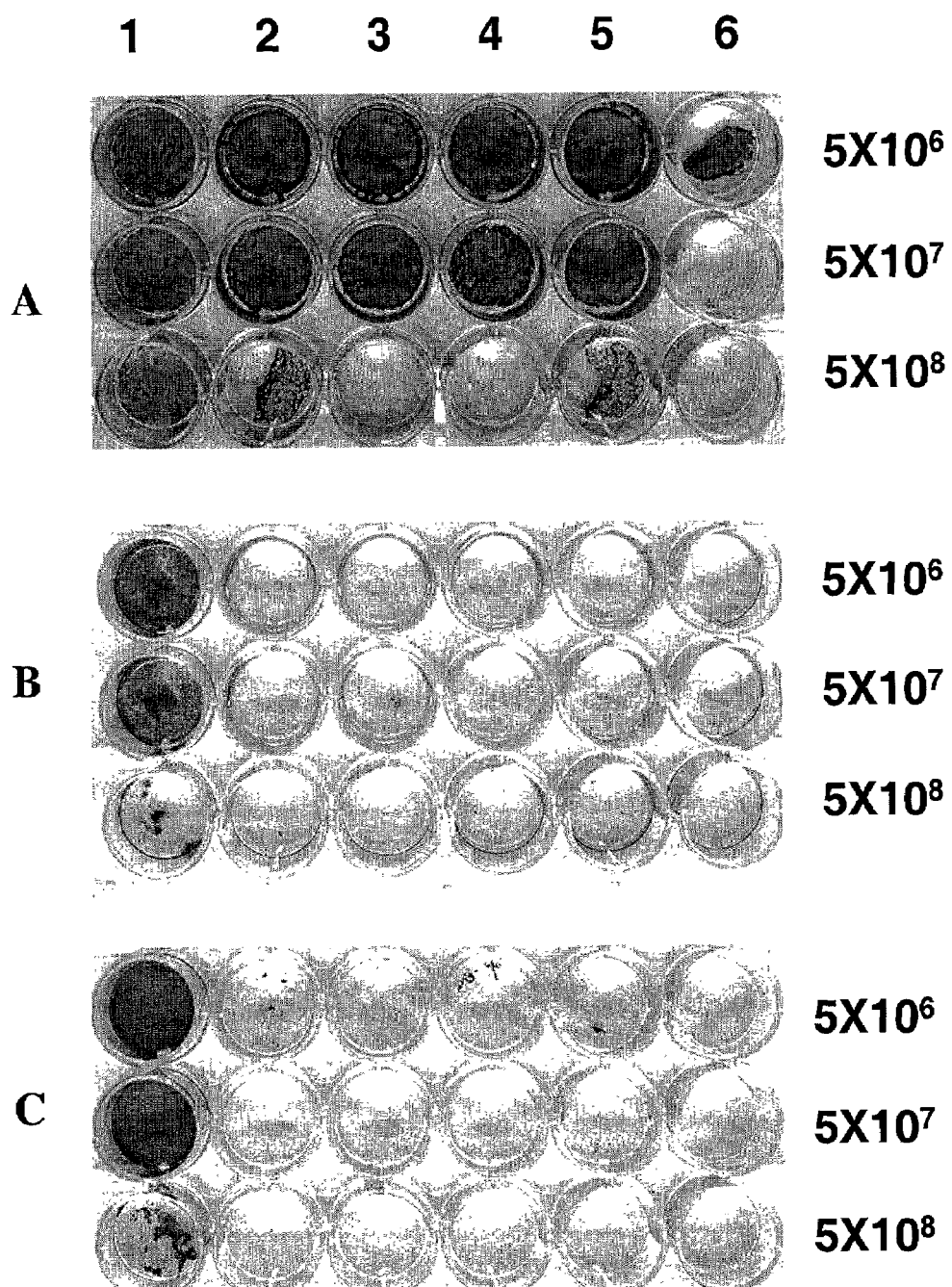
FIG. 1. Results of CPE assay to determine cytopathic effect of recombinant adenovirus vectors encoding E2F-Rb fusion coding sequence under the control of either TGF-β pathway-responsive promoter (PAI or SRE) or p53 pathway-responsive promoter (RGC or p53CON) were generated. In addition, the gene encoding green fluorescent protein was also incorporated in the vectors as a reporter. Panel A represents MRC-9 cells, Panel B represents the Hep3B cells, and Panel C represents WIDR cells. Lane 1: replication deficient (E1 deleted) recombinant adenovirus expressing the green fluorescent protein (GFP); Lane 2: PAI-Ad; Lane 3: SRE-Ad; Lane 4: RGC-Ad; Lane 5 p53CON-Ad. Particle concentrations are as indicated at the right of the Figure.
Figure 2:
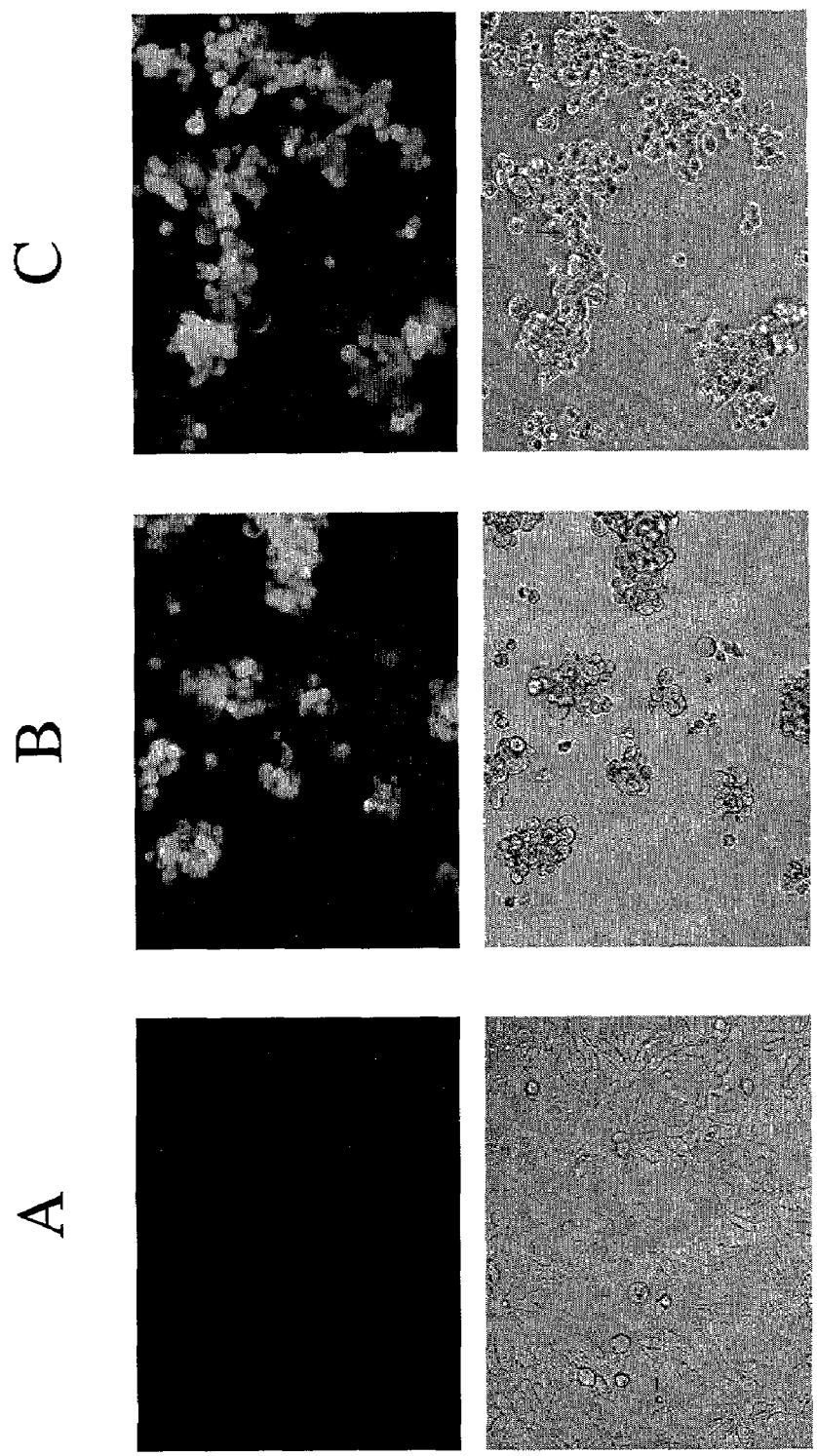
FIG. 2. Results of fluororesence microscopy (upper panels) illustrating GFP expression with pathway targeted vectors. Panel A represents the GFCB control vector, Panel B the SRE-Ad vector and Panel C the p53CON-Ad vector. Infection was at $5 \times 10^5$ particles per milliliter.

The present invention provides a selectively replicating recombinant virus comprising a pathway-responsive promoter operably linked to a repressor of viral replication.

The term "selectively replicating" refers to a vector capable of preferential replication in a cell in one phenotypic state relative to another phenotypic state. Examples of different phenotypic states would include the p53 pathway defective versus a normal cell of a given cell type. A virus which exhibits preferential replication indicates that the virus replicates at least five times as efficiently in the target cell type relative to a normal (control) cell of the same type at a given dosage level. In order to determine if a virus is truly selective, it is necessary to evaluate the ability of the virus to replicate in target cells as compared to normal cells of the same cell type in regard to a number of factors.

It is preferred that one compare the ability of a given vector to replicate in a target cell containing the condition to be targeted and normal cell of the same type which does not possess this condition. For example, the first step following viral infection is to induce the cell to enter the cell cycle because factors essential in for maximal viral replication efficiency are present only in S-phase. However, if one were attempting to evaluate the selectivity of a vector for selectivity in tumor cells, evaluation of the ability to replicate in a tumor cell relative to another cell which has already entered the cell cycle (such as an immortalized or transformed cell line), the selectivity of the virus for tumor cells will, to some degree, be obscured. Additionally, it has been observed that different cell types possess widely differing infectivities to a given virus. Although some viruses such as adenoviruses possess broad tissue tropism, other viruses are more restricted in the type of cells which they infect. By attempting to evaluate the performance of a given vector in cells of widely differing infectivities, it will be difficult to assess whether a lack of effect is due to the performance of the vector within the cell or merely the failure of the virus to infect the cell at all. By evaluating selectivity in target and normal cells of a given type, one minimizes this infectivity effect.

The temporal nature of the viral life cycle must also be considered. For example, even a wild-type vector may appear to possess selectivity in tumor cells relative to normal cells early after infection because the cell is already cycling. However this apparent selectivity diminishes over time once the virus has stimulated the cell cycle. Consequently, the time at which selectivity is evaluated following infection must be sufficient to avoid this initial replication lag in normal cells. Although this will vary with the type of virus being employed, this initial lag can readily be determined by one of skill in the art.

The effect of dosage must also be considered in the determination of whether a given recombinant adenovirus is demonstrating a selective effect in the target cell type. For example, if one is targeting the elimination of tumor cells and measuring the effect by cytotoxicity, a virus may be made to appear to have selective cytotoxicity by differing dosages. It has been observed that a sufficiently high dose almost any virus, regardless of the degree to which its genome has been modified, will be cytotoxic due simply to the effects of the presence of the viral proteins (such as hexon in the case of adenovirus) which are known to be cytotoxic. Similarly, even though the scientific literature may refer to a virus as "replication defective" (suggesting that the virus is absolutely incapable of replication in the absence of a cell line capable of complementing the viral defect), such viruses are more accurately described as "attenuated for replication." For example, adenoviruses containing a deletion of the entire E1 region which are frequently referred to as "replication deficient" or "replication defective" will replicate to some degree, particularly in cycling or rapidly dividing cells. As Mulligan observed (1990, Science 260:926-932):

Although the expression of the E1 region has been shown to affect the expression of other viral gene products necessary for replication (citing Horwitz, M. in Virology, B. N. Fields Ed. (Raven, N.Y., 1990) Chapter 60)), the required of E1 gene expression for viral replication does not appear to be absolute. The early characterization of E1-deficient viruses demonstrate that at high multiplicities of infection, the E1 region was dispensable for replication (citing Jones and Shenk (1979) PNAS (USA) 76(8):3665-3669).

Consequently, the effect of viral dose cannot be ignored when determining whether or not a virus is replicating in a selective manner.

One means to evaluate the replication selectivity of a virus for the target cells is to use evaluate the virus's "selectivity index" as follows. The commonly used parameter $ED_{50}$ (which is defined as the dose sufficient to induce cell death in 50% of the cells) provides an appropriate basis of comparison. The $ED_{50}$ of a virus can readily be determined by typical in vitro dose escalation experiments. In order to ensure the most consistent basis of comparison, the $ED_{50}$ is most appropriately expressed relative to a viral control to minimize the effects of variations of infectivity between the cell types being compared and any assay variations. Consequently the unitless ratio: $ED_{50}(virus)/ED_{50}(control)$ is used to express the relative toxicity of the virus in the cell and will be referred to as the "relative toxicity index" or "RTI." The "selectivity index" of a given virus is expressed by the ratio: RTI(target cells)/RTI(normal cells). Selectively replicating vectors will possess a selectivity index of at least 10, but preferably 50, 100 or greater.

For example, the selectively replicating adenoviral vectors U3EE and T1LT are designed to achieve selective replication and killing of tumor cells having p53 pathway defects. The U3EE is prepared in substantial accordance with the teaching of Examples 10 herein. Briefly, the U3EE virus contains a first expression cassette comprising a p53 response element (p53 CON) driving expression of the E2F-Rb fusion protein. The E2F-Rb fusion protein is a potent inhibitor of adenoviral E2 promoter activity and its presence in the cell will effectively suppress viral replication. The p53 response element is active in response to the presence of a functional p53 pathway. Consequently, in normal cells where the p53 pathway is intact, the U3EE virus will express the E2F-Rb fusion protein and the virus will not replicate. However, in cells having p53 pathway defect (the majority of tumor cells), the p53CON response element is not active and thus there is no repression of viral replication. The U3EE vector also contains an expression cassette comprising the MLP promoter driving expression of the Ad5 E3-10.5K pro-apoptotic gene. The use of the temporal promoters (such as the MLP promoter) is preferred when employing pro-apoptotic genes because one wishes to facilitate replication of viral DNA within the target cell prior to activating the pro-apoptotic signal. The MLP promoter is activated approximately seven hours post-infection following onset if replication of the U3EE genome thus inducing the activity of the E3-10.5 K protein. The T1LT adenoviral vector is essentially the same as the U3EE vector except that it contains an additional deletion in the E1a region to removes amino acids 4-25 of the 243R and 289R adenoviral E1a proteins. This deletion disrupts the ability of the p300 protein to bind to these E1a proteins.

Figure 3:
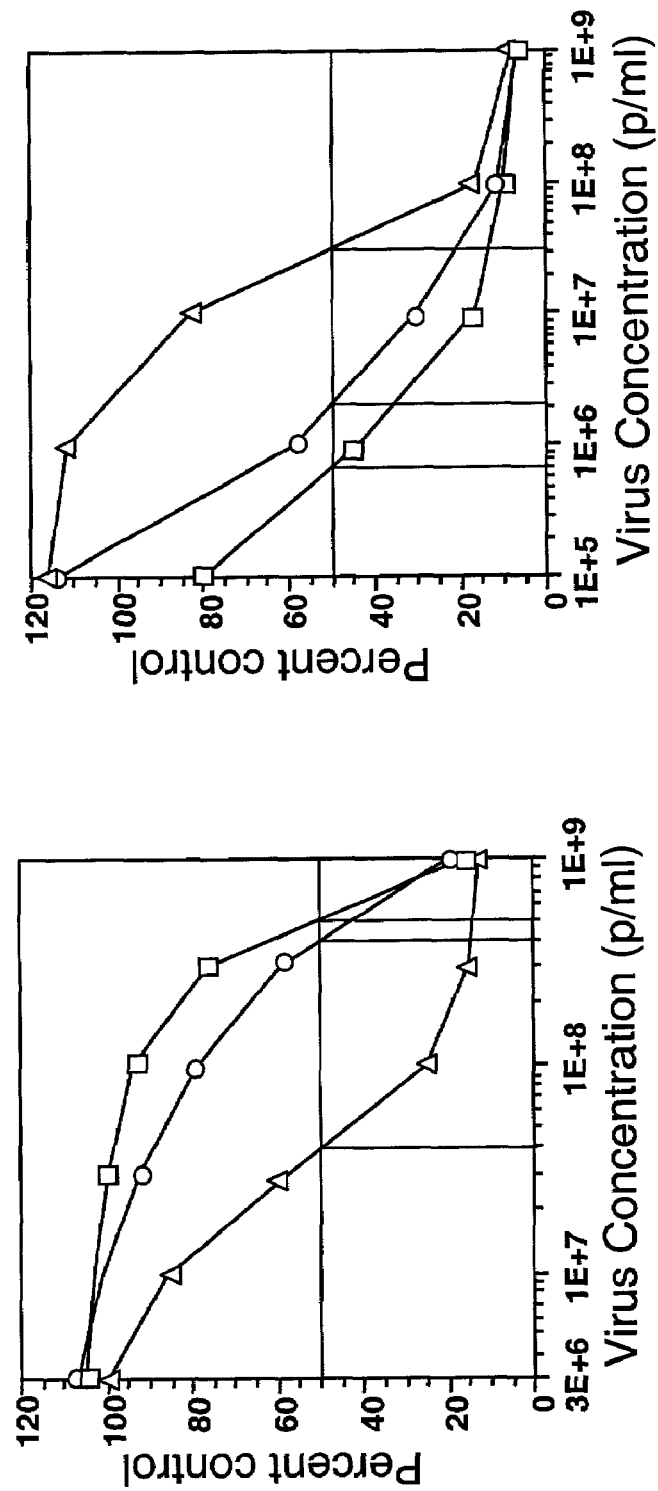
FIG. 3. Results of infection of normal bronchial epithelial cells (Panel A) and C33A cells (Panel B) with the recombinant viruses U3EE (squares), T1LT (circles) and L9IU (triangles). The vertical axes represent the percent of uninfected controls and the horizontal axes represent the viral dose in particles per milliliter. The experiments were performed by exposing a culture of each cells to six different concentrations of virus from $10^5$ to $10^9$ viral particles per milliliter. The cells were exposed to the virus for a period of one hour, the excess virus washed and the percent of viable cells at six days following infection was determined the MTS assay (Promega, Madison Wis.) in substantial accordance with the manufacturer's instructions. The horizontal line represents the level at which 50% of the cells remained viable. The intersection of the curves generated by the data and the horizontal dotted line is a measure of the $ED_{50}$ of the virus.

The U3EE and T1LT viruses were evaluated for their ability to replicate in and kill normal human brochial epitheial cells (NHBE) and C33A (an epithelial tumor cell line having a p53 defective pathway) using the L9IU vector as the control. The results of these experiments are presented in FIG. 3 of the accompanying drawings. The following table summarizes the data presented:

TABLE 1

Summary of RTI and Selectivity Indices of Viruses

| Virus | RTI (normal cells) | RTI (tumor cells) | Selectivity Index |
|---|---|---|---|
| L9IU | 1.0 | 1.0 | 1.0 |
| U3EE | 12.5 | 0.0233 | 536 |
| T1LT | 10 | 0.066 | 152 |

As can be seen from the data presented, the U3EE and T1LT viruses possesses high selectivity for tumor cells. As previously discussed, the L9IU virus possesses a slight replication advantage in the cycling tumor cells relative to the quiescent normal cells. By comparing the ratios of $ED_{50}(virus)/ED_{50}(control)$ in each of the cell types prior to calculating the selectivity index, the effects of such variations is minimized.

The term "recombinant" refers to a genome which has been modified through conventional recombinant DNA techniques.

The term "virus" refers to any of the obligate intracellular parasites having no protein-synthesizing or energy-generating mechanism. The viral genome may be RNA or DNA contained with a coated structure of protein of a lipid membrane. Examples of viruses useful in the practice of the present invention include baculoviridiae, parvoviridiae, picornoviridiae, herepesviridiae, poxviridiae, adenoviridiae, picotrnaviridiae. The term recombinant virus includes chimeric (or even multimeric) viruses, i.e. vectors constructed using complementary coding sequences from more than one viral subtype. See, e.g. Feng, et al. Nature Biotechnology 15:866-870

The term "adenovirus" is synonymous with the term "adenoviral vector" and refers to viruses of the genus adenoviridiae. The term adenoviridiae refers collectively to animal adenoviruses of the genus mastadenovirus including but no limited to human, bovine, ovine, equine, canine, porcine, murine and simian adenovirus subgenera. In particular, human adenoviruses includes the A-F sugenera as well as the individual serotypes thereof the individual serotypes and A-F subgenera including but not limited to human adenovirus types 1, 2, 3, 4, 4a, 5, 6, 7, 8, 9, 10, 11 (Ad11A and Ad 11P), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. The term bovine adenoviruses includes but is not limited to bovine adenovirus types 1, 2, 3, 4, 7, and 10. The term canine adenoviruses includes but is not limited to canine types 1 (strains CLL, Glaxo, RI261, Utrect, Toronto 26-61) and 2. The term equine adenoviruses includes but is not limited to equine types 1 and 2. The term porcine adenoviruses includes but is not limited to porcine types 3 and 4. In the preferred practice of the invention, the adenovirus is derived from the human adenovirus serotypes 2 or 5.

The term "pathway-responsive promoter" refers to DNA sequences that bind a certain protein and cause nearby genes to respond transcriptionally to the binding of the protein in normal cells. Such promoters may be generated by incorporating response elements which are sequences to which transcription factors bind. Such responses are generally inductive, though there are several cases where increasing protein levels decrease transcription. Pathway-responsive promoters may be naturally occurring or synthetic. Pathway-responsive promoters are typically constructed in reference to the pathway or a functional protein which is targeted. For example, a naturally occurring p53 pathway-responsive promoter would include transcriptional control elements activated by the presence of functional p53 such as the p21 or bax promoter. Alternatively, synthetic promoters containing p53 binding sites upstream of a minimal promoter (e.g. the SV40 TATA box region) may be employed to create a synthetic pathway-responsive promoter. Synthetic pathway-responsive promoters are generally constructed from one or more copies of a sequence that matches a consensus binding motif. Such consensus DNA binding motifs can readily be determined. Such consensus sequences are generally arranged as a direct or head-to-tail repeat separated by a few base pairs. Elements that include head-to-head repeats are called palindromes or inverted repeats and those with tail-to-tail repeats are called everted repeats.

Examples of pathway-responsive promoters useful in the practice of the present invention include synthetic insulin pathway-responsive promoters containing the consensus insulin binding sequence (Jacob, et al. (1995). J. Biol. Chem. 270:27773-27779), the cytokine pathway-responsive promoter, the glucocorticoid pathway-responsive promoter (Lange, et al. (1992) J Biol Chem 267:15673-80), IL1 and IL6 pathway-responsive promoters (Won K.-A and Baumann H. (1990) Mol. Cell. Biol. 10: 3965-3978), T3 pathway-responsive promoters, thyroid hormone pathway-responsive promoters containing the consensus motif: 5' AGGTCA 3.', the TPA pathway-responsive promoters (TREs), TGF-β pathway-responsive promoters (as described in Grotendorst, et al. (1996) Cell Growth and Differentiation 7: 469-480). Examples of other pathway-responsive promoters are well known in the art and can be identified in the Database of Transcription Regulatory Regions on Eukaryotic Genomes accessible through the world wide web at eimb.rssi.ru/TRRD.

In the preferred practice of the invention as exemplified herein, the vector comprises a synthetic TGF-β pathway-responsive promoter active in the presence of a functional TGF-β pathway such as the promoter containing SRE and PAI-RE response elements. PAI-RE refers to a synthetic TGF-β response element comprising sequences responsive to TGF-β signal isolated from the plasminogen activator-I promoter region. The construction of PAI-RE is described in Example 3 herein. The PAI-RE pathway-responsive promoter may be isolated as a 749 base pair fragment isolatable from the plasmid p800luc (as described in Zonneveld, et al. (1988) PNAS 85:5525-5529 and available from GenBank under accession number J03836). SRE refers to a synthetic TGF-β response element comprising a repeat of 4 of the Smad-4 DNA binding sequences (GTCTAGAC as described in Zawel, et al. (1988) Mol. Cell 1:611-617 The construction of SRE is described in Example 3 herein. The SRE response element may be generated by annealing complimentary oligonucleotides encoding the Smad-4 binding sequences and cloning in plasmid pGL#3-promoter luciferase vector (commercially available from ProMega).

Similarly, a "p53 pathway-responsive promoter" refers to a transcriptional control element active in the presence of a functional p53 pathway. The p53 pathway-responsive promoter may be a naturally occurring transcriptional control region active in the presence of a functional p53 pathway such as the p21 or mdm2 promoter. Alternatively, the p53 pathway-responsive promoter may be a synthetic transcriptional control region active in the presence of a functional p53 pathway such as the SRE and PAI-RE pathway-responsive promoters. p53-CON describes a p53 pathway-responsive promoter containing a synthetic p53 response element constructed by insertion of two synthetic p53 consensus DNA binding sequences (as described in Funk, et al. (1992) Mol. Cell Biol. 12:2866-2871) upstream of the SV40 TATA box. The construction of the p53-CON pathway-responsive promoter is described in Example 3 herein. RGC refers to a synthetic p53 pathway-responsive promoter using a single p53 binding domain identified in the ribosomal gene cluster. Kern, et al. (1991) Science 252:1708-1711 and Park, et al (1996) Molecular Carcinogenesis 16:101-108. p53CON and RGC response elements can be constructed by annealing complimentary oligonucleotides and p53 responsive promoters can be constructed (as described more fully in Example 3) by cloning in plasmid pGL3-promoter luciferase vector (commercially available from ProMega)

The term "target cell" refers to a cell of a given phenotypic state which is desired to be treated by administration of a therapeutic transgene. By the use of various pathway responsive promoter elements, one can target the expression of the virus to any given cell with an intact pathway. For example the repressor of viral replication may be expressed in a neoplastic target cell through the use of TGF-beta or p53 pathway responsive promoters. Similarly, the repressor of viral replication may be expressed in a arthritic target cell through an inflammatory responsive promoter, wherein the vector optionally encodes IL-10.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleotide sequences being linked are typically contiguous. However, as enhancers generally function when separated from the promoter by several kilobases and intronic sequences may be of variable lengths, some polynucleotide elements may be operably linked but not directly flanked and may even function in trans from a different allele or chromosome.

The term "repressor of viral replication" refers to a protein, if expressed in a given cell, substantially represses viral replication. As will be appreciated by those of skill in the art, the repressor of viral replication will be dependent on the nature of the parent adenoviral vector from which the recombinant vector of the present invention is derived. For example, in the case of adenoviral vectors or other DNA tumor viruses a E2F-Rb fusion construct may be employed. E2F-Rb fusion protein consists of the DNA binding and DP1 heterodimerizations domains of the human E2F transcription factor protein (amino acids 95-286 of wild type E2F) fused to the Rb growth suppression domain (amino acids 379-928 of the wild type Rb protein). The E2P-Rb fusion protein is a potent repressor of E2F-dependent transcription and arrests cells in G1. The DNA binding domain is located at amino acids 128-193 and the dimerization domain is located at 194-289. The sequence of the human E2F-1 protein is available from GenBank under accession number M96577 deposited Aug. 10, 1992. The sequences of E2F from other E2F family members of E2F from other species may be employed when constructing a vector for use in other species. In the situation where the recombinant virus is based on adeno-associated virus (AAV), the rep protein and its derivatives is an effective repressor of viral replication in the absence of adenovirus infection. In the situation where the virus is derived from herpes simplex virus, the ICPO-NX, a deleted form of the immediate early protein ICPO (Liun, et al. (1998) J. Virol. 72:7785-7795), protein may be used as an effective repressor of viral replication. Similarly, any protein with dominant negative activity can be used as a repressor of viral replication.

TGF-β and related proteins including activin, inhibins, and BMP are potent natural antiproliferative agents and are believed to play important roles in suppression of tumorigenicity. In its bioactive form, TGF-β is a 25-kDa disulfide-linked homodimer and is expressed in virtually all human tissues. Interestingly, many malignant cell types have retained the expression patterns that are seen in normal cells. TGF-β signals through heteromeric receptor complexes of type I and type II serine/threonine kinase receptors. Among the two receptor kinases, type II receptor possess an intrinsic kinase activity and upon binding to the to TGF-β ligand, the type II receptor heteromerizes with and transphosphorylates type I receptor. Phosphorylation of type I receptor activates its kinase activity, which in turn results in the phosphorylation of Smads, which are intracellular effectors. The phosphorylated type I receptor convey signals the inside of the cell resulting in cellular response like growth inhibition. Once inside the nucleus, the Smad complexes are known to activate transcription of target genes either by themselves acting as transcription factors or by regulating the activity of other transcription factors. Transcription factors that are believed to regulated by the TGF-β signal include CTF/NF-1, FAST-1, Sp1, Jun, SRF/TRF, Oct and CREB. The net results of these interactions lead to various known pleiotropic effects of TGF-β.

Transforming growth factor-β (TGF-β) and related proteins are potent inhibitors of proliferation of many cell types. The malignant progression of several tumors of epithelial and hematopoietic origin correlates with the loss of anti-proliferative and anti-invasive action of TGF-β. Failure of the TGF-β signaling has been shown to involve mutations or deletions or lack of expression of the receptors and/or intracellular effectors of the signal transduction pathway. Many malignant tumors that are resistant to TGF-β are also multiply defective for other tumor suppressor genes, thus limiting the utility of tumor suppressor gene replacement for effective therapy.

TGF-β pathway responsive promoters were constructed by incorporating sequences from plasminogen activator inhibitor-1 (PAI-promoter) or binding sites for Smad4/DPC4 (SRE-promoter) upstream of SV40 TATA box. Activities of these promoters were evaluated in transient transfection assays using luciferase as the reporter. The results are presented in Table 2 below:

These results demonstrate that both these promoters are active only in cells with functional TGF-β signal transduction. In a TGF-β pathway defective cell line such as MDA-MB468, which is defective for TGF-β signal transduction because of homozygous deletion of Smad4/DPC4, transfection of PAI-promoter or SRE-promoter operably linked to luciferase and infection with a recombinant adenovirus encoding Smad4 restored the activity of both of the above response elements, further confirming the specificity of these response element-containing promoters for TGF-β pathway as demonstrated by the data presented in Table 3 below.

TABLE 3

Restoration of TGF-β Responsive Promoter Activity in MDA-MB-468 Cells upon Infection with a Recombinant Adenovirus Encoding Smad4/DPC4 (Relative Luciferase Activity*(fold))

| Virus | Dose | PAI promoter − TGF-β | PAI promoter + TGF-β | SRE promoter − TGF-β | SRE promoter + TGF-β |
| --- | --- | --- | --- | --- | --- |
| BGCA | $1 \times 10^8$ | 1.0 | 1.53 | 1.00 | 1.00 |
| BGCA | $1 \times 10^9$ | 0.86 | 1.06 | 0.33 | 0.77 |
| DCCA | $1 \times 10^8$ | 1.13 | 4.86 | 8.50 | 139.17 |
| DCCA | $1 \times 10^9$ | 1.93 | 31.60 | 22.00 | 370.84 |

*Luciferase activity is expressed relative to the activity obtained with a contruct with BGCA in the absence of TGF-β.addition.
BGCA is a recombinant adenovirus expressing the β-gal gene.
DCCA is a recombinant adenovirus encoding Smad4/DPC4.

A plasmid containing PAI-promoter operably linked to E2F-Rb was then constructed and tested for its ability of selectively repress E2 promoter in cells with intact TGF-β pathway. In transient transfection assays, co-transfection of E2 promoter linked to luciferase with PAI-promoter operably linked to E2F-Rb showed selective repression of E2 promoter activity in 293 cells (with normal TGF-β pathway) and not in MDA-MB 468 cells (with a defective TGF-β pathway) as shown in Table 4, because of selective expression of E2F-Rb in 293 cells. As expected, co-transfection with CMV-E2F-Rb which expresses E2F-Rb in both these cell lines inhibited the activity of E2 promoter in both cell lines.

TABLE 2

Relative Luciferase Activity* (fold)

| Cell Line | TGF-β pathway | PAI promoter − TGF-β | PAI promoter + TGF-β | SRE promoter − TGF-β | SRE promoter + TGF-β |
| --- | --- | --- | --- | --- | --- |
| Hep3B | Normal | 68.82 | 128.42 | 105.02 | 86.47 |
| 293 | Normal | 51.62 | 88.78 | 9.40 | 46.94 |
| A549 | Normal | 33.26 | 56.76 | 2.87 | 17.93 |
| Panc1 | Normal | 15.36 | 141.80 | 1.14 | 29.03 |
| U87 | Normal | 110.40 | 73.88 | 7.42 | 7.85 |
| MCF-7 | Defective | 18.93 | 10.72 | 1.28 | 1.22 |
| WIDR | Defective | 10.66 | 4.41 | 1.24 | 1.57 |
| MDA-MB468 | Defective | 2.28 | 1.10 | 1.33 | 0.62 |
| AsPC-1 | Defective | 6.56 | 1.24 | 1.79 | 0.76 |
| Caco2 | Defective | 13.01 | 13.8 | 1.18 | 0.96 |
| MicaPaca2 | Defective | 14.08 | 1.81 | 0.79 | 26.34 |

*Luciferase activity is expressed relative to the activity obtained with a construct with no promoter.

TABLE 4

Selective Repression of E2 Promoter Activity by PAI-E2F-Rb In 293 Cells v. MDA-MB-468 Cells (Relative Luciferase Activity*(%))

| Repressor | MDA-MB-468 Cells | 293 Cells |
|---|---|---|
| None | 100 | 100 |
| CMV-E2F-Rb | 9.38 | 10.53 |
| PAI-E2F-Rb | 124.02 | 17.38 |

*Luciferase activity is expressed a a percentage relative to the activity obtained with a construct with no promoter.

p53 pathway responsive promoters were constructed by incorporating known p53 binding sites from either ribosomal gene cluster (RGC-promoter) or high affinity p53 binding sites (p53CON-promoter). Activities of these promoters were evaluated in transient transfection assays using luciferase as the reporter. The results of these experiments are presented in Table 5 below.

TABLE 5

Activities of p53 Responsive Promoters In Various Cell Lines (Relative Luciferase Activity*)

| Cell Line | p53 Status | p53 CON Promoter | RGC-Promoter |
|---|---|---|---|
| U87 | Wild-type | 3,921.12 | 112.33 |
| A549 | Wild-type | 647.30 | 16.36 |
| MCF-7 | Wild-type | 445.25 | 12.26 |
| 293 | Wild-type; inactive | 13.03 | 0.62 |
| Hep3B | Null | 4.62 | 1.22 |
| NCI-H358 | Null | 0.35 | 0.56 |
| Panc1 | Mutant | 1.56 | 1.02 |
| WIDR | Mutant | 16.17 | 1.07 |
| MDA-Mb-468 | Mutant | 4.88 | 0.87 |
| AsPC-1 | Mutant | 0.54 | 1.08 |
| Caco-2 | Mutant | 14.59 | 1.13 |
| MicaPaca2 | Unknown | 28.43 | 1.24 |

*Luciferase activity is expressed relative to the activity obtained with a construct w/o promoter Results indicated that both these response elements are active in cells with functional p53. In order to confirm that the p53 responsive promoter activity is due to functional p53, two cell lines WIDR and U87 were cotransfected with RGC promoter driving expression of luciferase gene and either an empty cassette control adenovirus vector (ZZCB) or a recombinant adenovirus constitutively producing p53 under the control of the CMV promoter (FTCB). The results of these experiments are presented in Table 6.

TABLE 6

Restoration/enhancement of p53 Responsive Promoter Activity in WIDR and U87 cells Upon Infection with a Recombinant Adenovirus Encoding p53 (Relative Luciferase Activity*)

| Virus | Dose | WIDR | U87 |
|---|---|---|---|
| ZZCB | $1 \times 10^8$ | 1.0 | 1.0 |
| ZZCB | $1 \times 10^9$ | 1.25 | 0.67 |
| FTCB | $1 \times 10^8$ | 4.71 | 20.30 |
| FTCB | $1 \times 10^9$ | 29.00 | 109.95 |

*Luciferase activity is expressed relative to the activity obtained with ZZCB infection.

As can be seen from the data presented, activity of p53-responsive promoter increases in a dose-dependent manner with increasing p53 activity.

Recombinant adenovirus vectors encoding E2F-Rb fusion coding sequence under the control of either TGF-β pathway-responsive promoter (PAI or SRE) or p53 pathway-responsive promoter (RGC or p53CON) were generated. In addition, the gene encoding green fluorescent protein was also incorporated in the vectors as a reporter. The resulting viruses were tested for their ability to selectively replicate and kill cells with either TGF-β or p53 pathway defects in cytopathic effect (CPE) assays. The results are shown in FIG. 1 of the attached drawings. In MRC9 (p53 pathway positive and TGF-β pathway positive) the wild type adenovirus was able to replicate and induce CPE even at low concentrations ($1 \times 10^6$ particles/ml), whereas the TGF-β or p53 pathway targeted vectors failed to induce CPE at that concentration. Only at the highest dose tested ($1 \times 10^8$ particles/ml), pathway-targeted vectors showed some CPE. In contrast in cell line such as WIDR (defective in both p53 and TGF-β pathways) and Hep3B (p53 null and TGF-β pathway defective in the absence of exogenous TGF-β) pathway-targeted vectors were effective in inducing CPE similar to the wild type virus even at low concentrations ($1 \times 10^6$ particles/ml). Fluorescence microscopy of Hep3B cells infected with pathway targeted vectors (SRE-Ad and p53Con-Ad) revealed high-level expression of the transgene and the spread of the virus within the culture, even when infected at a low particle concentration ($1 \times 10^5$ particles/ml exposed for two hours). In contrast, Hep3B cells infected with the replication-defective (E1A-deleted) GFP encoding adenovirus (GFCB) at the same concentration ($1 \times 10^5$ particles/ml), showed no GFP expression.

As previously indicated, the vectors of the present invention are capable of selective replication and lysis of the target cell under selective conditions. However, this is not meant to imply that additional layers of selectivity or toxicity cannot be engineered into these vectors. The present invention also provides recombinant adenoviruses containing additional modifications to the viral genome such as targeting modifications, transgene expression cassettes or modifications to the viral genome to facilitate selective replication in a given cell type or phenotypic state.

The term "targeting modification" refers to modifications to the viral genome designed to result in preferential infectivity of a particular cell type. Cell type specificity or cell type targeting may also be achieved in vectors derived from viruses having characteristically broad infectivities such as adenovirus by the modification of the viral envelope proteins. For example, cell targeting has been achieved with adenovirus vectors by selective modification of the viral genome knob and fiber coding sequences to achieve expression of modified knob and fiber domains having specific interaction with unique cell surface receptors. Examples of such modifications are described in Wickham, et al. (1997) J. Virol 71(11):8221-8229 (incorporation of RGD peptides into adenoviral fiber proteins); Arnberg, et al. (1997) Virology 227: 239-244 (modification of adenoviral fiber genes to achieve tropism to the eye and genital tract); Harris and Lemoine (1996) TIG 12(10):400-405; Stevenson, et al. (1997) J. Virol. 71(6):4782-4790; Michael, et al. (1995) gene therapy 2:660-668 (incorporation of gastrin releasing peptide fragment into adenovirus fiber protein); and Ohno, et al. (1997) Nature Biotechnology 15:763-767 (incorporation of Protein A-IgG binding domain into Sindbis virus). Other methods of cell specific targeting have been achieved by the conjugation of antibodies or antibody fragments to the envelope proteins (see, e.g. Michael, et al. (1993) J. Biol. Chem. 268:6866-6869, Watkins, et al. (1997) Gene Therapy 4:1004-1012; Douglas, et al. (1996) Nature Biotechnology 14: 1574-1578. Alternatively, particular moieties may be conjugated to the viral surface to achieve targeting (See, e.g. Nilson, et al. (1996) Gene Therapy 3:280-286 (conjugation of EGF to retroviral proteins). These recombinantly modified vectors may be produced in accordance with the practice of the present invention.

The term "transgene expression cassette" refers to a promoter functional in the target cell operably linked to a therapeutic transgene. The term promoter refers to nucleotide sequences which affect the transcription of another nucleotide sequence. Examples of promoters include weak constitutive promoters, temporal viral promoters or regulatable promoters.

The term "temporal promoters" refers to promoters which drive transcription or the therapeutic transgene at a point later in the viral cycle relative to the promoter controlling expression of the pathway-responsive promoter. Examples of such temporally regulated promoters include the adenovirus major late promoter (MLP), other promoters such as E3. In the preferred practice of the invention, the MLP promoter is employed. For herpes simplex viruses, the Latent Activated Promoters could be used.

The term "regulatable promoters" refers to inducible promoters, tissue specific or tumor specific promoters. The term "inducible promoter" refers to promoters which facilitate transcription of the therapeutic transgene preferable (or solely) under certain conditions and/or in response to external chemical or other stimuli. Examples of inducible promoters are known in the scientific literature (See, e.g. Yoshida and Hamada (1997) Biochem. Biophys. Res. Comm. 230:426-430; Iida, et al. (1996) J. Virol. 70(9):6054-6059; Hwang, et al. (1997) J. Virol 71(9):7128-7131; Lee, et al. (1997) Mol. Cell. Biol. 17(9):5097-5105; and Dreher, et al. (1997) J. Biol. Chem. 272(46); 29364-29371. Examples of radiation inducible promoters are described in Manome, et al. (1998) Human Gene Therapy 9:1409-1417). An additional level of selectivity can be imparted through the use of tissue specific of tumor specific promoters. Tissue specific and tumor specific promoters are well known in the art and include promoters active preferentially in smooth muscle (α-actin promoter), pancreas specific (Palmiter, et al. (1987) Cell 50:435), liver specific Rovet, et. al. (1992) J. Biol. Chem. 267:20765; Lemaigne, et al. (1993) J. Biol. Chem. 268:19896; Nitsch, et al. (1993) Mol. Cell. Biol. 13:4494), stomach specific (Kovarik, et al. (1993) J. Biol. Chem. 268:9917, pituitary specific (Rhodes, et al. (1993) Genes Dev. 7:913, prostate specific, etc.

The term "therapeutic transgene" refers to a nucleotide sequence the expression of which in the target cell produces a therapeutic effect. The term therapeutic transgene includes but is not limited to tumor suppressor genes, antigenic genes, cytotoxic genes, cytostatic genes, pro-drug activating genes, apoptotic genes, pharmaceutical genes or anti-angiogenic genes. The vectors of the present invention may be used to produce one or more therapeutic transgenes, either in tandem through the use of IRES elements or through independently regulated promoters.

The term "tumor suppressor gene" refers to a nucleotide sequence, the expression of which in the target cell is capable of suppressing the neoplastic phenotype and/or inducing apoptosis. Examples of tumor suppressor genes useful in the practice of the present invention include the p53 gene, the APC gene, the DPC-4/Smad4 gene, the BRCA-1 gene, the BRCA-2 gene, the WT-1 gene, the retinoblastoma gene (Lee, et al. (1987) Nature 329:642), the MMAC-1 gene, the adenomatous polyposis coli protein (Albertsen, et al., U.S. Pat. No. 5,783,666 issued Jul. 21, 1998), the deleted in colon carcinoma (DCC) gene, the MMSC-2 gene, the NF-1 gene, nasopharyngeal carcinoma tumor suppressor gene that maps at chromosome 3p21.3. (Cheng, et al. 1998. Proc. Nat. Acad. Sci. 95:3042-3047), the MTS1 gene, the CDK4 gene, the NF-1 gene, the NF2 gene, and the VHL gene.

The term "antigenic genes" refers to a nucleotide sequence, the expression of which in the target cells results in the production of a cell surface antigenic protein capable of recognition by the immune system. Examples of antigenic genes include carcinoembryonic antigen (CEA), p53 (as described in Levine, A. PCT International Publication No. WO94/02167 published Feb. 3, 1994). In order to facilitate immune recognition, the antigenic gene may be fused to the MHC class I antigen.

The term "cytotoxic gene" refers to nucleotide sequence, the expression of which in a cell produces a toxic effect. Examples of such cytotoxic genes include nucleotide sequences encoding pseudomonas exotoxin, ricin toxin, diptheria toxin, and the like.

The term "cytostatic gene" refers to nucleotide sequence, the expression of which in a cell produces an arrest in the cell cycle. Examples of such cytostatic genes include p21, the retinoblastoma gene, the E2F-Rb fusion protein gene, genes encoding cyclin dependent kinase inhibitors such as P16, p15, p18 and p19, the growth arrest specific homeobox (GAX) gene as described in Branellec, et al. (PCT Publication WO97/16459 published May 9, 1997 and PCT Publication WO96/30385 published Oct. 3, 1996).

The term "cytokine gene" refers to a nucleotide sequence, the expression of which in a cell produces a cytokine. Examples of such cytokines include GM-CSF, the interleukins, especially IL-1, IL-2, IL-4, IL-12, IL-10, IL-19, IL-20, interferons of the α, β and γ subtypes especially interferon α-2b and fusions such as interferon α-2α-1.

The term "chemokine gene" refers to a nucleotide sequence, the expression of which in a cell produces a cytokine. The term chemokine refers to a group of structurally related low-molecular cytokines weight factors secreted by cells are structurally related having mitogenic, chemotactic or inflammatory activities. They are primarily cationic proteins of 70 to 100 amino acid residues that share four conserved cysteine residues. These proteins can be sorted into two groups based on the spacing of the two amino-terminal cysteines. In the first group, the two cysteines are separated by a single residue (C-x-C), while in the second group, they are adjacent (C-C). Examples of member of the 'C-x-C' chemokines include but are not limited to platelet factor 4 (PF4), platelet basic protein (PBP), interleukin-8 (IL-8), melanoma growth stimulatory activity protein (MGSA), macrophage inflammatory protein 2 (MIP-2), mouse Mig (m119), chicken 9E3 (or pCEF-4), pig alveolar macrophage chemotactic factors I and I (AMCF-I and -II), pre-B cell growth stimulating factor (PBSF), and IP10. Examples of members of the 'C-C' group include but are not limited to monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1 α (MIP-1-α), macrophage inflammatory protein 1 β (MIP-1-β), macrophage inflammatory protein 1 γ (MIP-1-γ), macrophage inflammatory protein 3-α (MIP-3-α, macrophage inflammatory protein 3 β (MIP-3-β), chemokine (ELC), macrophage inflammatory protein 4 (MIP-4), macrophage inflammatory protein 5 (MIP-5), LD78 β, RANTES, SIS-epsilon (p500), thymus and activation-regulated chemokine (TARC), eotaxin, I-309, human protein HCC-1/NCC-2, human protein HCC-3, mouse protein C10.

The term "pharmaceutical protein gene" refers to nucleotide sequence, the expression of which results in the production of protein have pharmaceutically effect in the target cell.

Examples of such pharmaceutical genes include the proinsulin gene and analogs (as described in PCT International Patent Application No. WO98/31397, growth hormone gene, dopamine, serotonin, epidermal growth factor, GABA, ACTH, NGF, VEGF (to increase blood perfusion to target tissue, induce angiogenesis, PCT publication WO98/32859 published Jul. 30, 1998), thrombospondin etc.

The term "pro-apoptotic gene" refers to a nucleotide sequence, the expression thereof results in the programmed cell death of the cell. Examples of pro-apoptotic genes include p53, adenovirus E3-11.6K (derived from Ad2) or adenovirus E3-10.5K (derived from Ad), the adenovirus E4orf4 gene, p53 pathway genes, and genes encoding the caspases.

The term "pro-drug activating genes" refers to nucleotide sequences, the expression of which, results in the production of protein capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine (5-FC) to 5-fluorouracil (5-FU), a potent antitumor agent. The lysis of the tumor cell provides a localized burst of cytosine deaminase capable of converting 5FC to 5FU at the localized point of the tumor resulting in the killing of many surrounding tumor cells. This results in the killing of a large number of tumor cells without the necessity of infecting these cells with an adenovirus (the so-called bystander effect"). Additionally, the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir may be employed.

The term "anti-angiogenic" genes refers to a nucleotide sequence, the expression of which results in the extracellular secretion of anti-angiogenic factors. Anti-angiogenesis factors include angiostatin, inhibitors of vascular endothelial growth factor (VEGF) such as Tie 2 (as described in PNAS (USA)(1998) 95:8795-8800), endostatin.

It will be readily apparent to those of skill in the art that modifications and or deletions to the above referenced genes so as to encode functional subfragments of the wild type protein may be readily adapted for use in the practice of the present invention. For example, the reference to the p53 gene includes not only the wild type protein but also modified p53 proteins. Examples of such modified p53 proteins include modifications to p53 to increase nuclear retention, deletions such as the Δ13-19 amino acids to eliminate the calpain consensus cleavage site, modifications to the oligomerization domains (as described in Bracco, et al. PCT published application WO97/0492 or U.S. Pat. No. 5,573,925).

It will be readily apparent to those of skill in the art that the above therapeutic genes may be secreted into the media or localized to particular intracellular locations by inclusion of a targeting moiety such as a signal peptide or nuclear localization signal (NLS). Also included in the definition of therapeutic transgene are fusion proteins of the therapeutic transgene with the herpes simplex virus type 1 (HSV-1) structural protein, VP22. Fusion proteins containing the VP22 signal, when synthesized in an infected cell, are exported out of the infected cell and efficiently enter surrounding non-infected cells to a diameter of approximately 16 cells wide. This system is particularly useful in conjunction with transcriptionally active proteins (e.g. p53) as the fusion proteins are efficiently transported to the nuclei of the surrounding cells. See, e.g. Elliott, G. & O'Hare, P. Cell. 88:223-233:1997; Marshall, A. & Castellino, A. Research News Briefs. Nature Biotechnology. 15:205:1997; O'Hare, et al. PCT publication WO97/05265 published Feb. 13, 1997. A similar targeting moiety derived from the HIV Tat protein is also described in Vives, et al. (1997) J. Biol. Chem. 272:16010-16017.

Additionally modifications to increase the potency of the vectors of the present invention include but are not limited to alterations within E1, introductions of mutations in E4 to increase the cytotoxicity (Muller, et al (1992) J. Virol. 66:5867-5878), up-regulation of viral death proteins such as E4orf4 or E3 11.6K proteins.

In the preferred practice of the invention as exemplified herein, the vector of the present invention comprises a conditionally replicating adenovirus containing a p53 or TGF-β pathway-responsive promoter driving expression of the E2F-Rb fusion protein, additionally comprising the cytosine deaminase gene is under control the temporal E3 promoter. In such instances the cytosine deaminase is produced only in tumor cells following viral replication. In the preferred practice of the invention, the prodrug converting gene is under the control of a relatively weak or tissue-specific or tumor specific promoter.

In another embodiment of the invention, the vector comprises a recombinant adenovirus with a p53 or TGF-β pathway-responsive promoter driving expression of the E2F-Rb fusion protein and a transgene expression cassette expressing cytosine deaminase alone or in a bi-cistronic express cassette containing cytosine deaminase, and IRES element and the MIP-3-alpha protein. Because cytosine deaminase is expressed, tumor cell killing is achieved upon administration of a prodrug such as 5-fluorocytosine. Low level expression of MIP-3-alpha will aid in the development of antitumor immunity.

Multi-level, multi-functional or multiple pathway responsive cascade are used interchangeably herein to refer to the construction of a pathway responsive elements so as to produce a therapeutic effect where more than one pathway can be probed simultaneously. It will be apparent to those of skill in the art that the vector control elements as described above may be combined to provide multiple layers of selectivity to the vectors of the present invention. As an example of multi-level control, it would be possible to design a conditionally replicating adenovirus that can replicate and kill cells that have defects in either Rb, TGF-β or p53 pathway. Such a vector would include expression of a dominant negative inhibitor of viral replication controlled by a p53-responsive promoter as a primary level of control. As a result, in any cell (such as all normal cells) with functional p53, but not in cell with inactive p53, the dominant negative inhibitor is expressed and the viral replication is blocked. However, this vector may replicate in tumor cells with functional p53 but with defects in other pathways such as TGF-β and Rb pathway. Therefore, additional levels of control can be inserted which would essentially inactivate functional p53 in tumor cells, thus allowing viral replication, when other pathways are defective.

As a second level of control, the same vector would also consist of an expression cassette containing adenovirus E1B-55K protein, which can functionally inactivate p53, under the control of a promoter that is active only in TGF-β pathway defective cells. A promoter that is active only in TGF-β pathway defective cells can be constructed by inserting repressor binding sites within a promoter such that expression of the repressor using a TGF-β responsive promoter elsewhere on the vector will lead to blockage of the promoter activity in cells with intact TGF-β signaling. On the other hand, in cells where the TGF-β pathway is defective, the repressor is not synthesized, thus the promoter will be active. Because of the expression of E1B-55K from the promoter that is active only in cells in which TGF-β pathway is defective, endogenous p53 is inactivated. Alternatively, any natural promoter that is down-regulated because of TGF-β signaling can be used. The inclusion of the above two expression cassettes will ensure that the dominant negative inhibitor is expressed only when both p53 and TGF-β pathways are normal (leads to blockage of replication), but not when one or both of them are defective (leads to viral replication).

As a third level of control, expression of a protein such as Smad7 or any other dominant negative form of Smad, which is capable of inactivating TGF-β pathway (Nakao et al., Nature Oct. 9, 1997; 389(6651):631-635) controlled by a E2F-responsive promoter is achieved in the same vector. A E2F-responsive promoter (such as E2F1 promoter, E2 promoter or a synthetic promoter with multiple E2F-binding sites upstream of a minimal promoter such as SV40 TATA box) is active when Rb pathway is defective. Because of this third level of control, in cells with defective Rb pathway, Smad7 is expressed which in turn inactivates Smad4 and blocks TGF-β signal transduction. Therefore, E1B-55K is made and p53 is inactivated leading to lack of expression of the dominant negative inhibitor. Therefore, viral replication can proceed unhindered. On the other hand, if Rb pathway is normal, Smad7 is not synthesized, thus TGF-β signal transduction proceeds normally. Therefore, E1B-55K is not made, resulting in a functional p53 capable of expressing the dominant negative inhibitor to block viral replication.

With a above three levels of control, a defect in any one or two or all of the three pathways (Rb, TGF-β and p53) would ultimately lead to viral replication and cell lysis. Viral replication will not occur only when all three pathways are functional as in normal cells.

As can be appreciated by those of skill in the art, the vectors of the present invention can be used in many variations for the detection and treatment of a wide variety of pathway defects using a variety of pathway-responsive promoters. However, in the preferred practice of the invention as exemplified herein, the recombinant adenoviral vector is derived from genus adenoviridiae. Particularly preferred viruses are derived from the human adenovirus type 2 or type 5. When an adenoviral vector is used as the parent vector, the preferred inhibitors of viral replication is the E2F-RB fusion protein.

In the preferred practice of the invention when using the vectors of the present invention to treat diseases associated with uncontrolled cellular proliferation, it is preferred that an adenoviral vector be employed containing specific deletions in the E1A region so as to eliminate the ability of the E1a gene product to bind to the p300 and Rb proteins while retaining the transactivating function of the E1a CR3 domain. The vectors of the present contain deletions in the E1a coding sequence to eliminate p300 and p105-Rb binding sites in the 13S coding sequence. In the preferred practice of the invention, the p300 binding deletions are represented by deletions of amino acids from about 4 to about 25 or from about 36 to about 49.

The deletions in the E1a 289R coding sequence necessary to achieve elimination of p300 and pRb binding are preferably as minimal as possible to prevent major disruption of the secondary and tertiary structure of the E1a 289R protein. In order to eliminate p300 binding it is preferred that a mutation be introduced in the DNA sequence encoding the p300 binding domains of 289R. Deletions of less than about 30 amino acids in the C-terminal region to eliminate p300 binding are preferred, although smaller modifications are preferred. For example, a deletion of amino acids 4 to 25 (dl1101), from about amino acid 30 to amino acid 49 (dl1103) and more particularly 36 to 49 are alternatively preferred to eliminate p300 binding. Point mutations sufficient to disrupt binding p300 are particularly preferred. For example, a point mutation of the second amino acid from arginine to glycine (Arg2→Gly2) in the 289R protein has been demonstrated to disrupt p300 binding (See e.g., pm563, Whyte, et al, (1989) Cell 56:67-75). Similarly, in regard to eliminating pRb105 binding, minimal modifications are preferred. Elimination of selective amino acids in the pRb105 binding domain such as amino acid 111-123 (dl1107) and amino acids 124-127 (dl1108) are preferred. Deletion of amino acids 111-123 (dl1107) is particularly preferred in that it retains the p107 binding activity of the 289R protein.

Additionally, the elimination of amino acids from approximately 219 to 289 of the E1a 289R protein and 173 to 243 of the E1A 243R protein may be introduced. For example, by introducing a point mutation at position corresponding to position 1131 of the human Ad5 genome (i.e., changing the cytosine$^{1131}$ to a guanine) creates a stop codon. This mutation results in the elimination of amino acids 219 to 289 of the E1a 289R protein and 173 to 243 of the E1A 243R protein. This mutation is made optionally in addition to the deletions in Rb and p300 binding described above. Additional examples of such parent vectors are described in co-pending U.S. patent application Ser. No. 60/104,317 and 08/09/172,684 filed Oct. 15, 1998.

In the preferred practice of the invention as exemplified herein, the preferred p53 pathway-responsive promoters are p53-CON and RGC. Preferred TGF-β pathway-responsive promoters are selected from the group consisting of PAI-RE and SRE.

In the preferred practice of the invention the therapeutic gene is a pro-drug activating gene e.g., cytosine deaminase. In the preferred practice of the invention to induce anti-tumor immunity, the vector of the present invention encodes MIP-3-alpha.

Preferred promoters for the expression of the therapeutic gene are the temporal promoters such as MLP and E3.

In adenoviral constructs, the elimination or delay in action of the Ad E3-11.6 K protein to minimize cell lysis induced by adenovirus until replication is achieved. In particular, the elimination of the native E3-11.6K/10.5K gene would be preferable. This would minimize the immune response until after the initial round of localized spreading occurs. At this later time, once apoptosis of the initially infected cells is achieved and localized virus spreading is permitted, the immune response would be advantageous. The 11.6K protein (or the corresponding E3-10.5K protein of Ad5) is a pro-apoptotic gene and may be used to achieve cell killing in tumor cells. However, as one wishes to delay the early lysis of the target cell to maximize viral replication, it is preferred that the 11.6K/10.5K gene be placed under control of a temporal promoter such as the MLP promoter to delay onset of its apoptotic effect.

A particularly preferred embodiment of the invention is the selectively replicating adenoviral vector designated 01/PEME which is a recombinant adenoviral vector which been modified in accordance with the teaching of the present invention and incorporates several of the features described herein: 1) a deletion in the E1a gene corresponding to amino acids 4-25 of the E1a 243R and 289R proteins (dl1101) that prevents viral inactivation of p53 and viral induction of cellular DNA synthesis synthesis (Howe, et al. (1990) PNAS (USA) 87:5883-7.), 2) a deletion in the E3 region derived from dl327 that prevents viral interference with immune response Andersson M, et al. (1985) Cell 43:215-22, and Burgert, et al. (1987) PNAS (USA) 84:1356-60) 3) an expression cassette comprising the PRP promoter expressing the E2F-RB fusion protein (PRP-E2F-Rb, Gregory et al. supra) that blocks viral replication in normal cells, and 4) insertion of a modified viral gene expression cassette wherein the E311.6K protein is under control of the adenovirus type 5 major late promoter (MLP-E3-11.6K) to enhances virus spread in tumor cells (Tollefson, et al. (1996) Virology 220: 152-62 and Tollefson, et al. 1996) J. Virol. 70:2296-306.) In cells in which growth and apoptosis are dysregulated, hallmarks of neoplastic transformation, expression of the inhibitor, E2F-Rb, is blocked and replication of 01/PEME proceeds with efficiencies similar to those of wild type adenovirus. In normal cells, including actively dividing cells, the inhibitor is expressed and viral replication is effectively prevented. In data which is presented in more detail below, when tested in vitro against a panel of 31 tumor cell lines and 4 normal primary cell cultures 01/PEME was highly selective for tumor cells versus normal cells. In mouse models, 01/PEME administered by intravenous administration was effective against established human xenograft tumors derived from lung, colorectal, prostate and cervical carcinomas.

01/PEME was engineered to be attenuated in normal cells by taking advantage of functional p53 in normal cells to decrease virus replication. 01/PEME encodes an inhibitor of viral replication under the control of a p53-responsive promoter (PRP). The inhibitor of viral replication is an E2F antagonist (E2F-Rb) comprising the DNA-binding domain of E2F and the transrepression domain of retinoblastoma protein (Rb). Howe, et al. (1990) PNAS (USA) 87:5883-7. Additionally, because p300/CBP is required for maximal p53 activity (Ramachandra. et al. (2001) Nature Biotechnology 19:1035-41; Tollefson, et al. (1996) Virology 220:152-62) 01/PEME contains a deletion of amino acids 4-25 of the E1a 243R and 289R gene products derived from the adenovirus mutant dl1101. This deletion prevents interaction of E1a with p300/CBP thereby augmenting p53-dependent E2F-Rb expression. Furthermore, the deletion of critical residues in the CR1 domain of E1a abolishes viral induced cellular DNA synthesis. E2F activity regulates viral E2a and E1a promoters that control expression of viral DNA replication proteins and many of the cellular S-phase genes. Therefore, p53-dependent expression of the E2F antagonist would be effective in inhibiting virus replication in cells with higher p53 activity but lower E2F activity. Transcriptional activity of p53 is lost or severely reduced in tumor cells because of alterations in p53 itself, mdm2, p14$^{ARF}$ or interaction with viral proteins such as human papillomavirus E6 protein (Heise, et al. (1997) Nat. Med. 3:639-45). In contrast, E2F-responsive promoters are more active in tumor cells than in normal cells (Heise, et al. (1999) Cancer Res. 59:2623-8) because dysregulation of E2F occurs in virtually all human cancers as a result of mutations including those found in RB1 or CDKN2A, or as a result of overexpression of the CCND/CDK4 complex.

Figure 5:
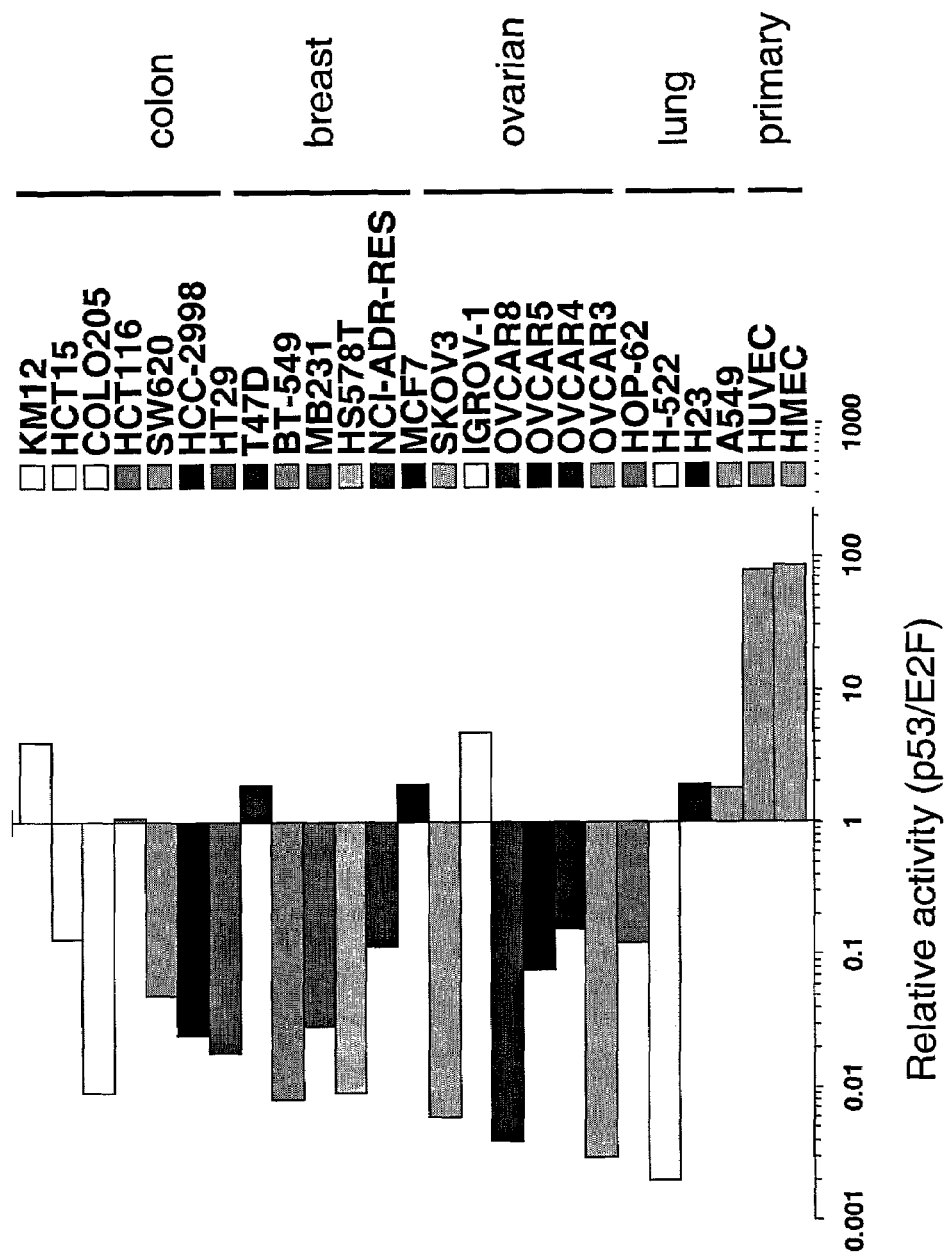
FIG. 5 is a graphical representation of transcriptional activities of E2F and p53 in a variety of human tumor or normal cells as determined by transient transfection assays using reporter plasmids. After determining the activities, the relative activity was calculated by dividing the E2F activity with p53 activity.

Consistent with these concepts, transient transfection assays with reporter plasmids using a number of tumor cell lines and two primary human normal cells, human mammary epithelial cells (HMEC) and human microvascular endothelial cells (HMVEC), indicated that most tumor cells have higher activity of E2F relative to p53 activity. This data is presented in FIG. 5 of the attached drawings.

Following infection of normal cells with 01/PEME, cellular p53 drives expression of E2F-Rb, antagonizing E2F function and inhibition of viral replication. In contrast, tumor cells with p53 inactivating mutations do not support expression of E2F-Rb from 01/PEME and thus allow replication of 01/PEME to proceed unhindered. Tumor cells with functional p53 also allow replication of 01/PEME, because their higher E2F activity facilitates transcription from E2F-dependent viral E1a and E2a promoters immediately after the virus enters the cells and prior to expression of sufficient quantities of E2F-Rb. Additionally, because inhibition by E2F-Rb is dependent upon competition with endogenous E2F activity, E2F-Rb would be less effective in inhibiting adenoviral early promoters when E2F activity is high as in tumor cells. In contrast, p53-dependent E2F-Rb expression would be effective in attenuating the virus propagation in normal cells because of both functional p53 and tightly regulated E2F pathways.

In order for an oncolytic adenovirus to be efficacious, it must also be highly cytopathic to tumor cells. Achievement of preferential replication in tumor cells with p53-regulated E2F-Rb expression provided us an opportunity to increase tumor-specific cytopathicity. To enhance tumor cell killing and promote virus spread, 01/PEME also contains the adenovirus type 2 viral major late promoter (MLP) in the E3 region to drive overexpression of viral E3-11.6K, a protein involved in killing of infected cells and release of the virus (Prives C, Hall P A. The p53 pathway. J. Pathol. 1999; 187:112-26). Utilizing the MLP in this manner provides replication-specific killing because the MLP becomes active after the onset of DNA replication.

Figure 6:
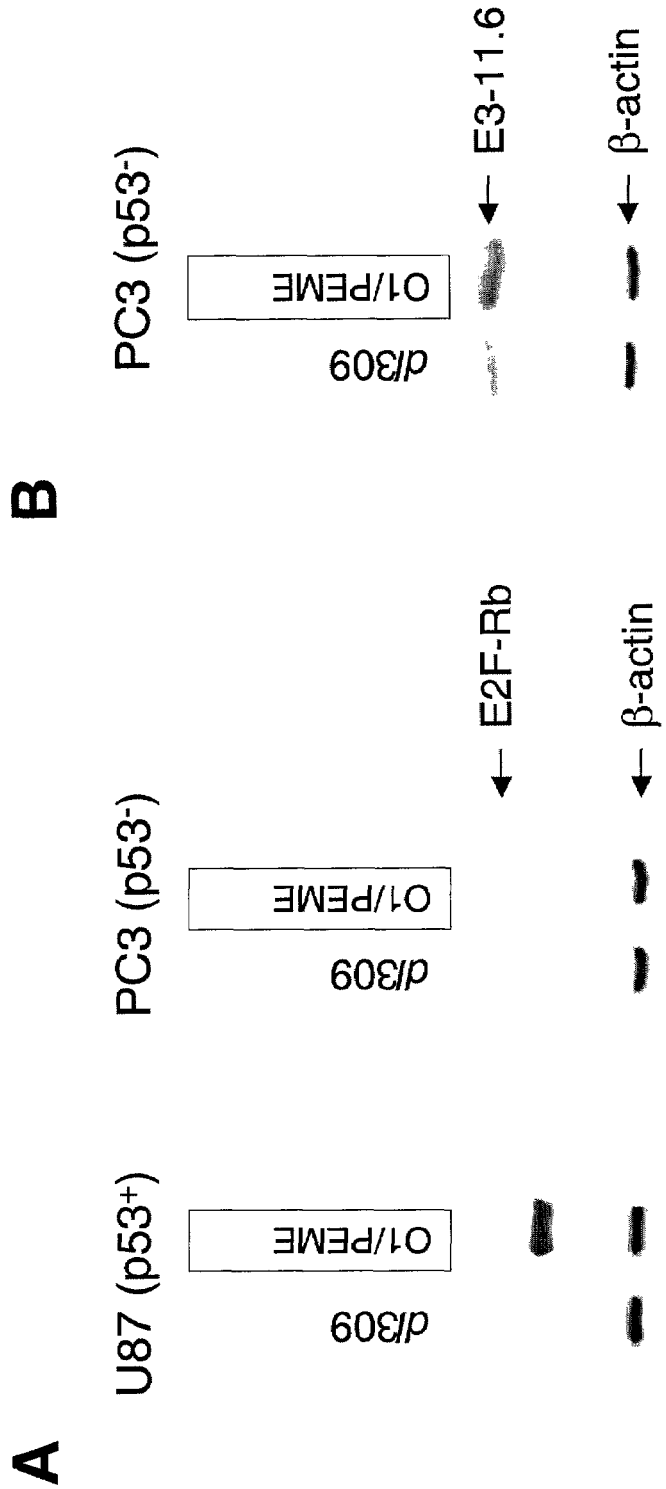
FIG. 6 is a autoradiogram demonstrating the expression of E2F-Rb and E3-11.6K from 01/PEME. Panel A demonstrates p53-dependent expression of E2F-Rb. U87 or PC3 cells infected with indicated vectors were harvested 48 h post-infection and cell lysates were subjected to immunoblot analysis for either E2F-Rb using anti-Rb or beta-actin with anti-alpha-actin antibody. Panel B illustrates the overexpression of E3-11.6K in cells infected with 01/PEME PC3 cell lysates were also subjected to immunoblot analysis as in panel A except with either anti-E3-11.6K or anti-alpha actin antibody.

To assess expression of E2F-Rb and E3-11.6K from 01/PEME, immunoblot analysis was performed, the results of which are presented in FIG. 6 of the attached drawings. As a control, a mutant adenovirus dl309 (Rogulski, et al. (2000) Cancer Res. 60:1193-6.) was included; dl309 carries a partial deletion in the E3 region but retains the endogenous E3-11.6K gene. High level expression of E2F-Rb was observed for 01/PEME in p53 wild-type U87 cells, but not in p53-null PC3 cells, indicating that E2F-Rb expression is p53-dependent. Immunoblot analysis of the PC3 cell lysates also demonstrated overexpression of E3-11.6K in 01/PEME as compared to dl309.

Figure 7:
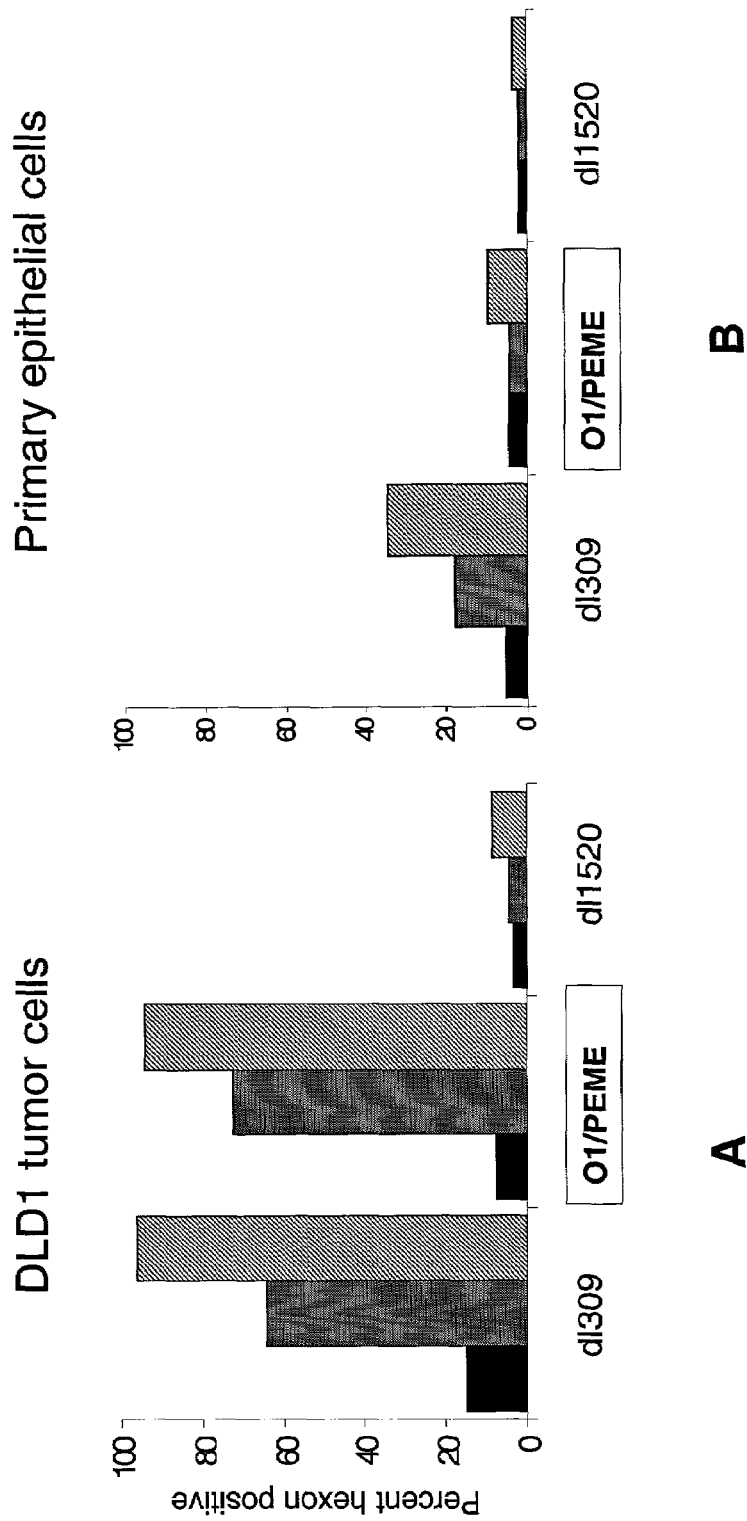
FIG. 7 is a graphical representation of hexon protein expression of dl309, 01/PEME and dl1520 infected cells. DLD1 tumor cells (Panel A) as compared to HMEC (primary epithelial cells, Panel B) were infected with indicated viruses and harvested at 2 (solid bars), 3 (shaded bars) and 4 (hatched bars) days after infection. After staining with FITC-conjugated anti-hexon antibody, expression was assessed by flow cytometric analysis.

In in vitro assays, the activity of 01/PEME was compared to that of dl1520, a replicating adenovirus with a deletion in the E1b55k gene, and dl309, a replicating adenovirus with a deletion in the E3 region. The results of these experiments are provided in graphical form in FIG. 7 of the attached drawings. The dl1520 virus, previously proposed to selectively replicate in cells with p53 pathway defects, is perhaps the most widely evaluated replicating adenovirus for use in cancer therapy in both preclinical and clinical studies (Nemunaitis, et al. (2000) Cancer Res. 60:6359-66; Nemunaitis, et al. (2001). J. Clin. Oncol. 19:289-98; Ganly, et al. (2000). Clin. Cancer Res. 6:798-806; Khuri, et al. (2000) Nat. Med. 6:879-85; Kirn, et al. (1998) Nat. Med. 4:1341-2; Kirn, et al. (1998) Proc. Am. Soc. Clin. Oncol. 17:391a.)

The adenovirus dl309, an adenovirus with partial E3 deletion that exhibits greater cytopathic effects than the wild-type adenovirus, was included as a positive control for cell killing effect. To determine if p53-dependent expression of E2F-Rb would result in selective attenuation of adenovirus in normal cells, the production of hexon, a viral late gene product, was assessed by flow cytometry following infection of tumor or normal cells. In the p53-mutated tumor cell line DLD1, 01/PEME showed similar percentage of hexon positive cells (>90%) as compared to dl309 four days after infection. In contrast, in human mammary epithelial cells (HMEC) 01/PEME showed a markedly diminished percentage of hexon positive cells as compared to dl309 (>4-fold), indicating selective attenuation of 01/PEME in normal cells. Infection with dl1520 resulted in a very low percentage of cells (<10%) positive for hexon in both tumor and normal cells.

In cell proliferation assays, the cytopathicity of 01/PEME was similar to that of dl309 in p53-mutated DLD1, but markedly reduced in HMEC (>2 log dose of the virus required for 50% reduction in cell proliferation), thereby demonstrating selective attenuation. In both cell types, compared to dl309 at least 2-log higher dose of dl1520 was required to achieve 50% reduction in cell proliferation, indicating attenuation of dl1520 in both cell types.

Cell proliferation assays were also performed in other normal and tumor cell types to compare relative attenuation of 01/PEME and dl1520. After performing assays, the concentrations of each of the viruses required for a 50% reduction in cell viability ($ED_{50}$) was determined. Relative attenuation over dl309 was then calculated and plotted. The results are presented in FIG. 8 of the attached drawings. In this analysis 01/PEME was attenuated 30-300-fold in normal HMEC, NHLF and human vascular endothelial cells (HUVEC) but <2-fold in tumor cells. dl1520 was attenuated >60-fold in both normal cells and in tumor cell lines such as DLD1. In other tumor cell lines, such as MDA-MB231, A549 and HepG2, dl1520 was more attenuated than 01/PEME.

Figure 8:
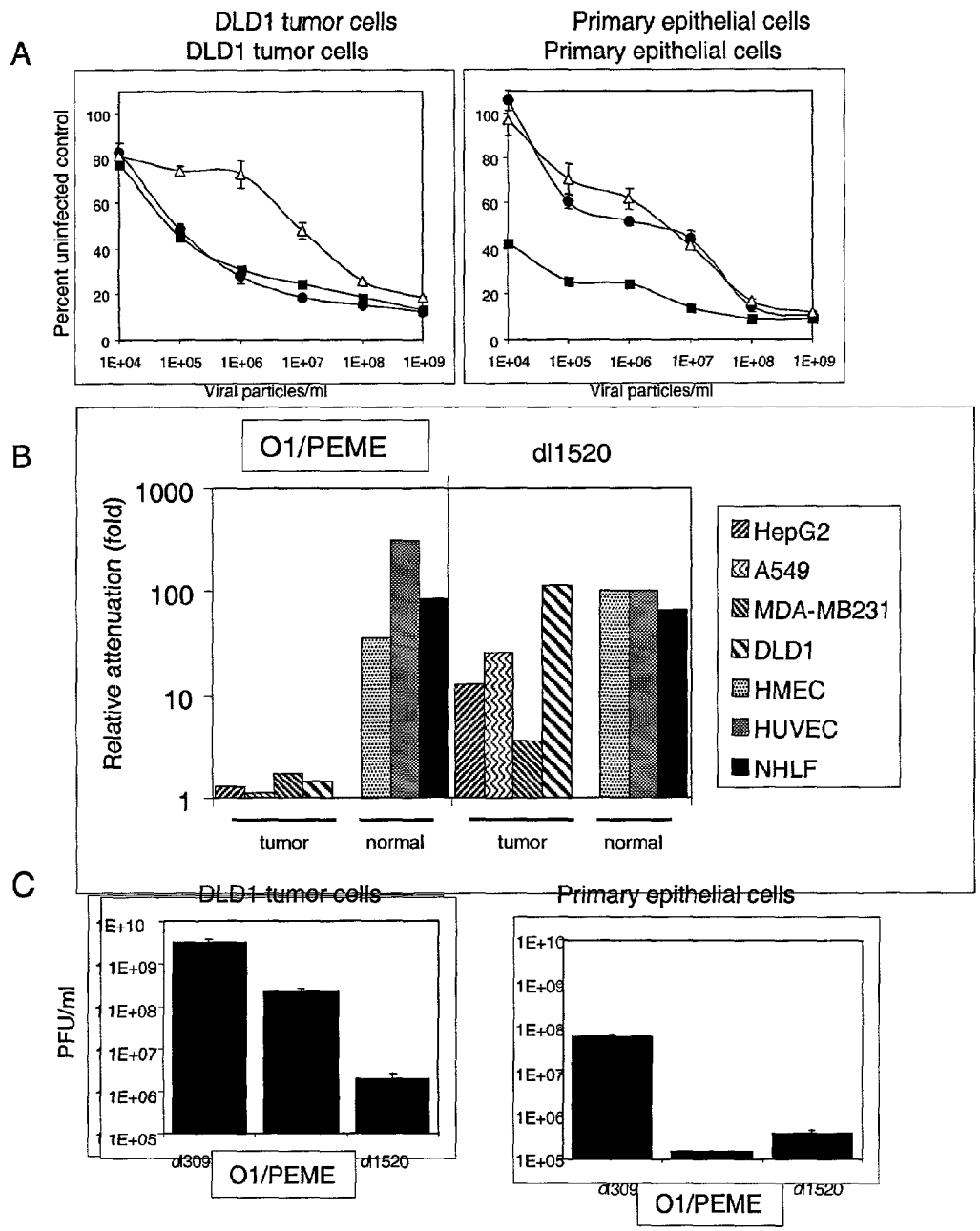
FIG. 8 are graphical representations of proliferation of dl309, 01/PEME and dl1520 in a variety of cell lines replication assays demonstrating that 01/PEME is selectively attenuated in normal cells relative to tumor cells. In panel A, there is a dose-dependent reduction in cell viability following infection of DLD1 or HMEC with dl309 (■) 01/PEME (●) and dl1520 (Δ) is shown. Results are depicted as a function of the value determined for the uninfected negative control sample. In panel B 01/PEME is compared to dl1520 in a variety of normal and tumor cell line. In panel C, the three vectors are compared in DLD-1 tumor cells versus primary fibroblast cells. Cell proliferation and viral. In panel B. human cells of primary or tumor origin were infected with viruses as in panel A. The percentage of viable cells was determined and concentrations of each of the viruses required for a 50% reduction in cell viability i.e., $ED_{50}$ were determined. The relative attenuation was calculated by dividing the $ED_{50}$ of the test virus by the $ED_{50}$ for dl309. A relative attenuation value of 1 indicates that the $ED_{50}$ for dl309. Values >1 are indicative of a virus that is more attenuated than dl309, whereas values <1 are indicative of a virus that is more potent than dl309. In panel C, DLD1 or NHLF were infected with viruses and three day post-infection, both cells and supernatants were collected and subjected to titer determination on HEK-293 cells.

To determine whether selectivity observed for 01/PEME in hexon production and cell proliferation assays can also be seen in viral replication assay, we compared the replication of viral constructs in DLD1 and NHLF cells (FIG. 8, Panel C). Compared to replication of dl309, replication of 01/PEME was reduced by 447-fold in NHLF and only 14-fold in DLD1. In contrast, replication of dl1520 was decreased by 168 and 1630-fold in NHLF and DLD1 respectively. Attenuated replication of dl1520 in both NHLF and DLD1 was also evident when time course of hexon synthesis in infected cells was measured by flow cytometry (data not shown).

Figure 9:
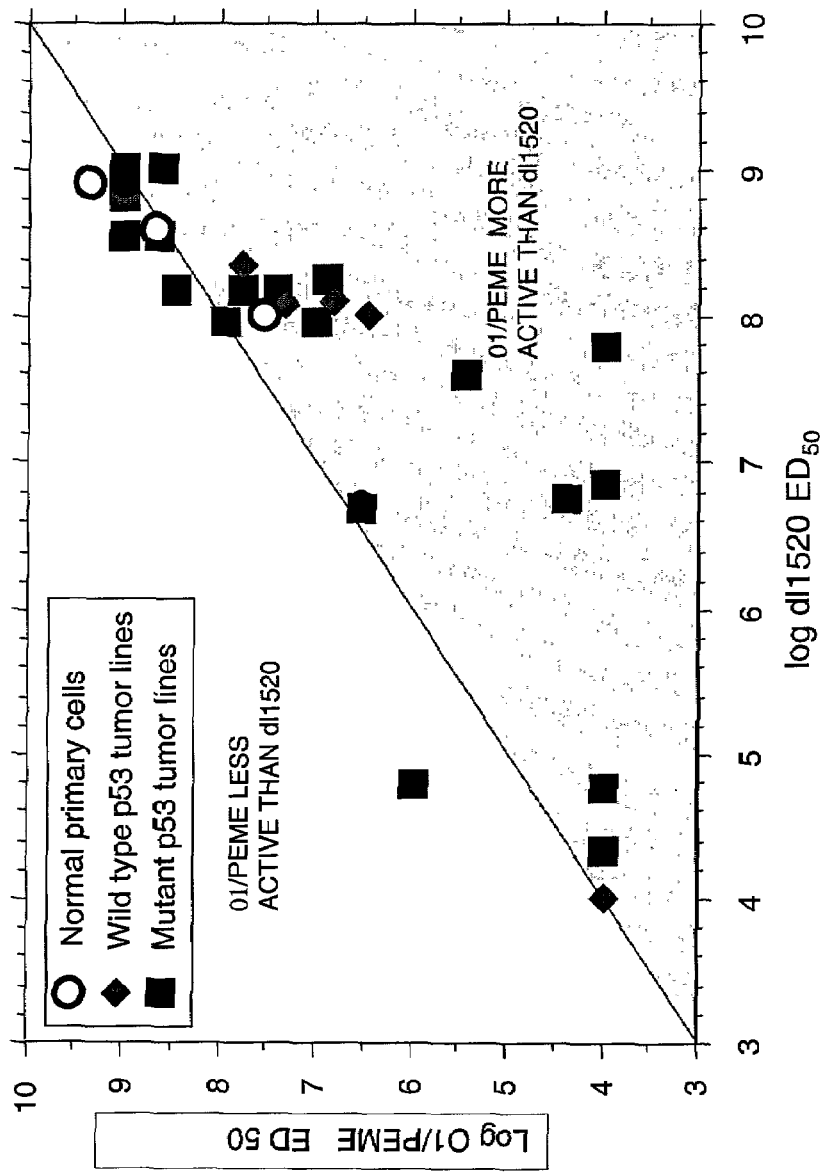
FIG. 9 is a graphical presentation of data demonstrating a correlation between $ED_{50}$ of 01/PEME and dl1520. $ED_{50}$ of 01/PEME and dl1520 in ~30 tumor cell lines (filled) and primary normal cells (open circles) was determined using the MTS viability assay. Data points that fall along the diagonal indicate that the viruses had equal activity, data points within the shaded portion indicate that dl1520 was more attenuated that 01/PEME.

01/PEME exhibits greater cell killing activity than dl1520 in a large number of human tumor cell lines from National Cancer Institute's in vitro anticancer drug screen (NCI-ACDS) panel. Tumor cell lines from NCI-ACDS panel (Monks, et al. (1991) J. Natl. Cancer Inst. 83:757-66) have been very valuable in identification of potent antineoplastic drugs and understanding the molecular alterations that determine sensitivity (Amundson, et al. (2000) Cancer Res. 60:6101-10). We performed cell proliferation assays using more than 30 human tumor cell lines of different tissues of origin of the NCI-ACDS to compare relative efficacy of cell killing by 01/PEME and dl1520. Analysis of the data indicated potent activity of 01/PEME in tumor cells of different tissues of origin and genetic background. After determining the $ED_{50}$ values in each cell line, log $ED_{50}$ for 01/PEME was platted against log $ED_{50}$ for dl1520. The data is presented in FIG. 9 of the attached drawings. The data show higher degree of attenuation of dl1520 compared to 01/PEME in most tumor cell lines examined.

Figure 10:
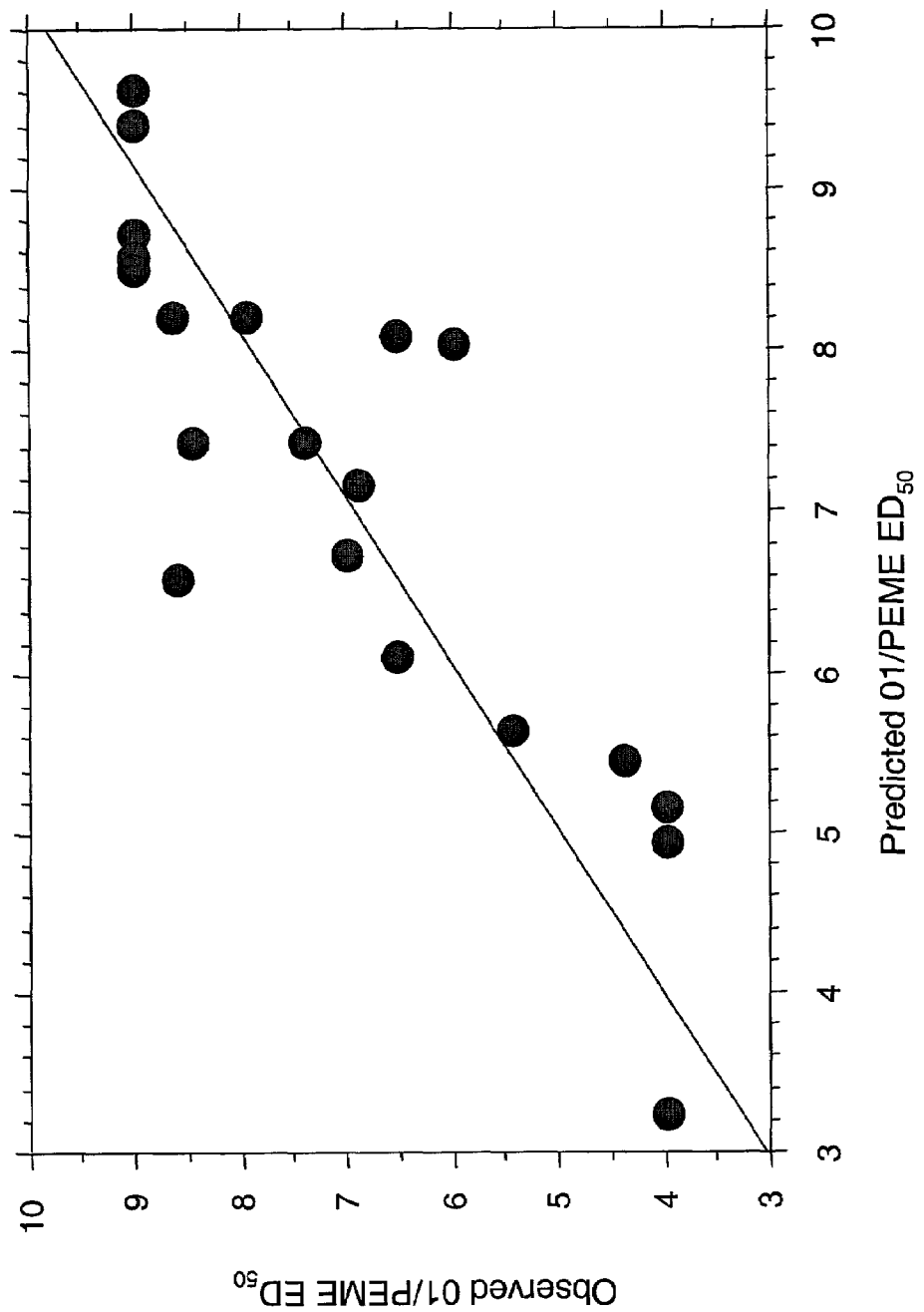
FIG. 10 is a graphical representation of data demonstrating a correlation between observed $ED_{50}$ of 01/PEME and the predicted sensitivity of cell lines based on gene expression profiling. The $ED_{50}$ of 01/PEME was determined on ~30 cell lines using the MTS viability assay. Multiple regression analysis of the RNA expression profiling of those cells lines for CAR, cyclinE, Bcl-2, and Bax could be used to predict the sensitivity of the cell line to 01/PEME.

We sought to determine the molecular characteristics that may assist in predicting the sensitivity of tumor cell lines to killing by 01/PEME. Measurement of gene expression at the mRNA level has been shown to be a good predictor of activity in the cell[24]. Unlike determination of protein expression, measurement of mRNA expression is more quantitative, rapid and sensitive, and requires relatively small sample. We performed quantitation of the relative basal levels of 10 transcripts known for their role in adenovirus entry (Coxsackie B Virus-Adenovirus Receptor, CAR)[25], to be regulated by E2F (cyclin E, cyclin A., cyclin B1 and B-myb)[26] and p53 (p21, MDM2, GADD45)[27] and in conferring sensitivity to apoptosis (Bcl-2, Bax)[28] in about 30 cell lines of the NCI-ACDS. Stepwise regression analysis using the log RNA concentrations (independent variables) versus the log $ED_{50}$ for 01/PEME (dependent variable) was used to generate a formula for the predicted log $ED_{50}$ of 01/PEME as a function of expression of CAR, Bcl-2, BAX and cyclin E. Analysis of the fit between the predicted $ED_{50}$ values and observed $ED_{50}$ values for 01/PEME in the subset of p53 mutant cell lines in the sample (20 cell lines) showed a strong correlation (R=0.893, $R^2$=0.798) which was significant at p<0.0001. The predicted log $ED_{50}$ values versus observed log $ED_{50}$ values for 01/PEME are shown in FIG. 10 of the attached drawings. The line shown is the linear regression for the data (slope=0.967, intercept=0.138).

01/PEME, was observed to have oncolytic activity in cell culture. Therefore we reasoned that delivery of 01/PEME to human tumors in animal models would result in inhibition of tumor growth. The following sections describe studies that demonstrate inhibition of tumor growth by intratumoral and intravenous routes of delivery of 01/PEME. Some studies included A/C/N/53, a nonreplicating adenovirus vector encoding the human p53 cDNA, and/or dl1520, a replicating adenovirus with a deletion in the E1b-55k gene, for comparison. Human tumor cell lines were implanted in the flanks of immunodeficient nude mice. Once tumors were established (tumor size range: 50-100 mm$^3$) 01/PEME was administered daily on five consecutive days. The tumor sizes were measured over time using calipers.

Figure 11:
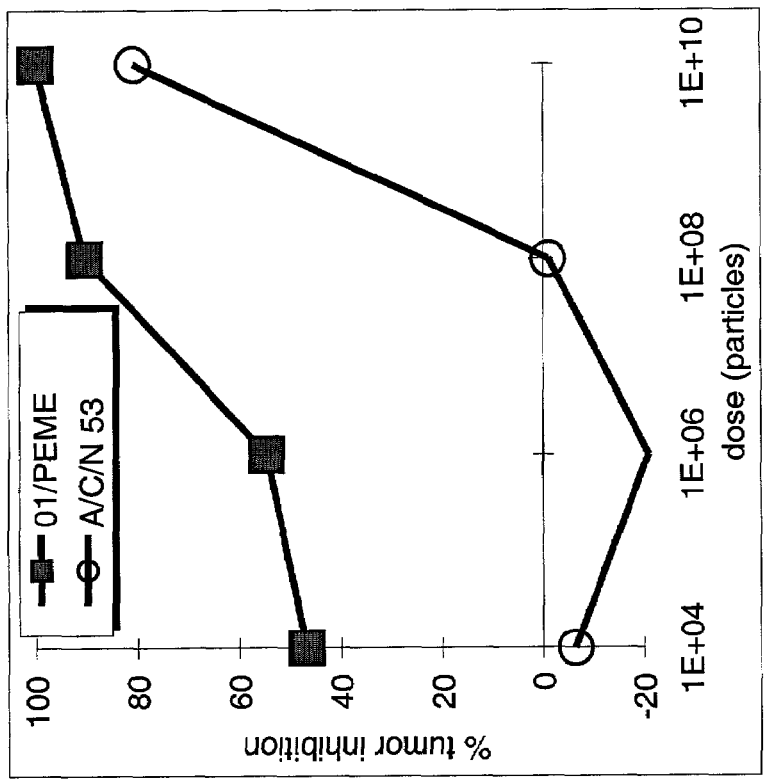
FIG. 11 is a graphical representation of data demonstrating a dose dependent inhibition of PC3 prostate tumor growth with 01/PEME treatment in PC3 subcutaneous tumor model. Nude mice with PC3 subcutaneous tumors were treated by intratumoral administration of the indicated doses on 5 consecutive days. Panel A provides tumor size plotted over time for each 01/PEME dose level. Panel provides a dose response of 01/PEME and A/C/N/53 (Gregory, et al., U.S. Pat. No. 6,210,939 issued Apr. 3, 2001 the entire teaching of which is herein incorporated by reference) based on tumor size on day 30.
Figure 11:
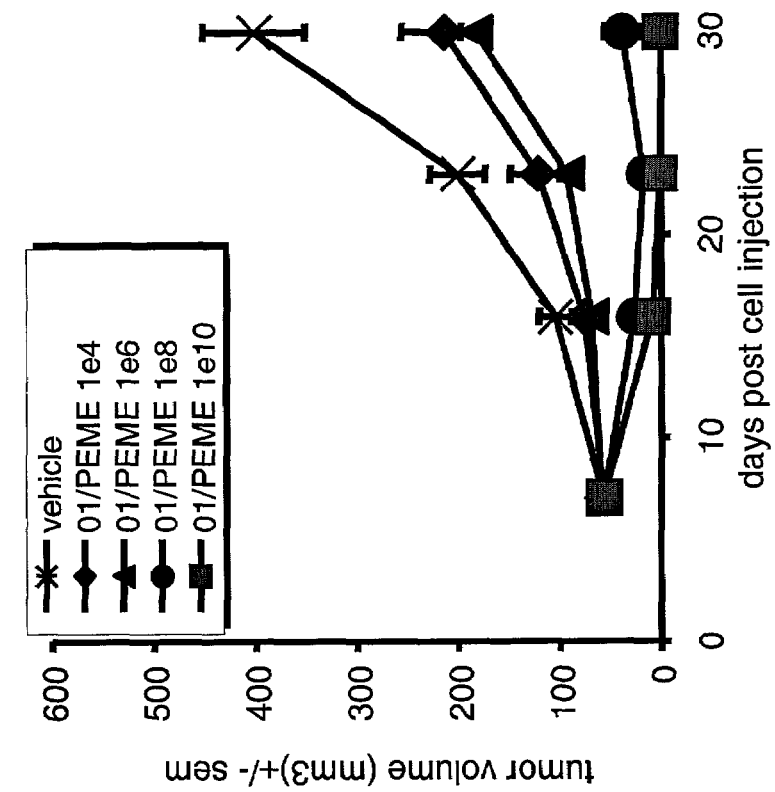

A study was performed to determine the dose response curves of 01/PEME and A/C/N/53 in the PC3 subcutaneous xenograft prostate tumor model. PC3 cells were injected into the flank of female nude mice. Treatment of tumors by intratumoral administration of doses (1×10$^4$, 1×10$^6$, 1×10$^8$, 1×10$^{10}$ particles) of 01/PEME or A/C/N/53 was initiated 9 days after cell injection, with dosing for 5 consecutive days. There were 8 mice in each treatment group. Tumor size was measured one time per week over the following 3 weeks until untreated animals became moribund due to cachexia. For each treatment group, the percent of tumor size inhibition relative to the vehicle treated group was plotted from tumor sizes measured on day 30. The results are presented in FIG. 11 of the attached drawings. Treatment of tumors with 01/PEME required ~10,000 fold less virus than treatment with A/C/N/53 to achieve 50% tumor inhibition (i.e. 50% reduction in mean tumor size relative to vehicle treated group). On day 30, 8 of 8 mice treated with 1×10$^{10}$ particles 01/PEME were tumor free, whereas, 1 of 8 mice treated with 1×10$^{10}$ particles A/C/N/53 were tumor free. At the dose of 1×10$^8$ particles, 3 of 8 mice treated with 01/PEME were tumor free and no mice treated with A/C/N/53 were tumor free. 01/PEME was effective in inhibiting tumor growth by intratumoral administration using the PC3 subcutaneous xenograft tumor model.

Figure 12:
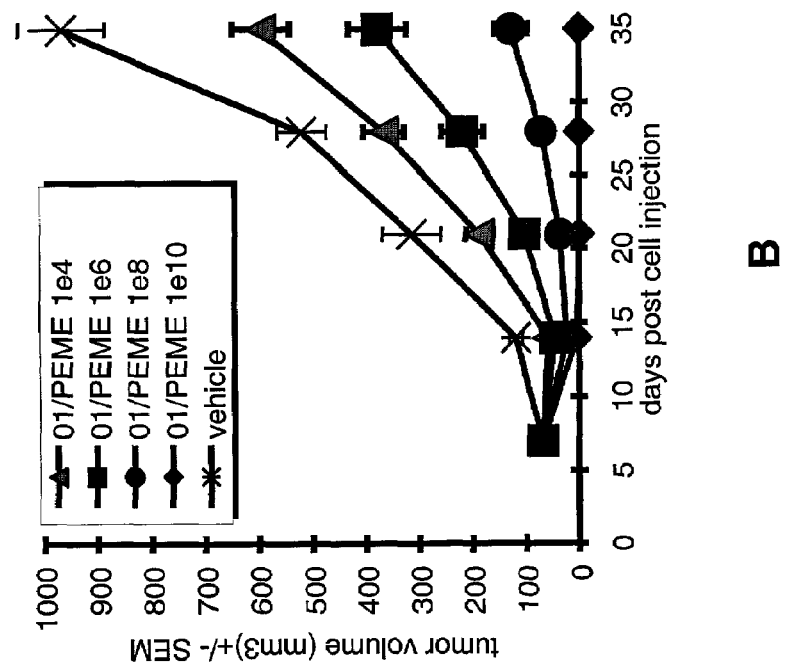
FIG. 12 is a graphical representation of data demonstrating a dose dependent inhibition of PC3 prostate tumor growth with 01/PEME treatment in PC3 subcutaneous tumor model. Nude mice with PC3 subcutaneous tumors were treated by intratumoral administration of the indicated doses on 5 consecutive days. Panel A presents tumor size plotted over time for each 01/PEME dose level. Panel B provides dose response of 01/PEME and dl1520 based on tumor size on day 35.
Figure 12:
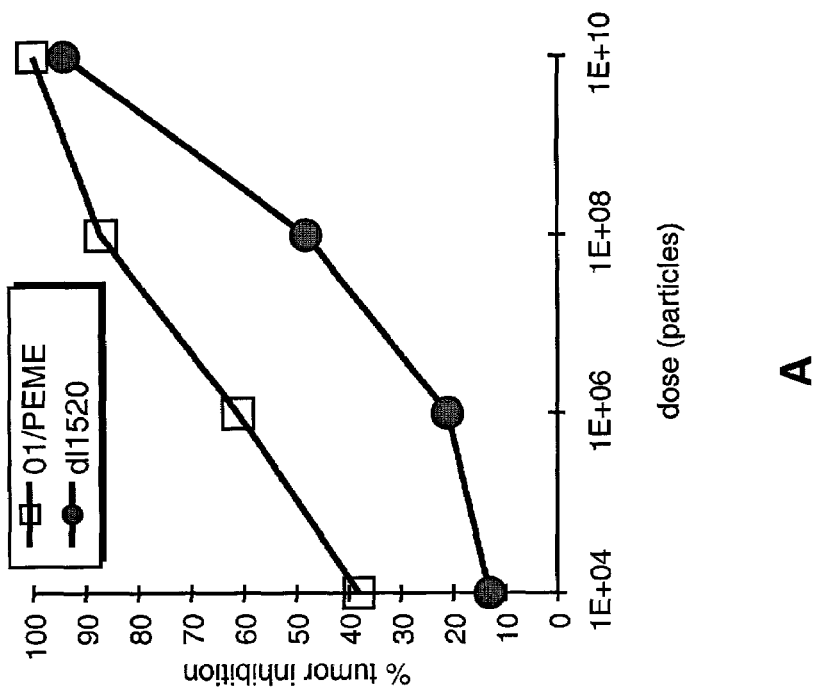

A study was performed to determine the dose response curves of 01/PEME and dl1520 in the PC3 subcutaneous xenograft prostate tumor model. PC3 cells were injected into the flank of female nude mice. Treatment of tumors by intratumoral administration of doses (1×10$^4$, 1×10$^6$, 1×10$^8$, 1×10$^{10}$ particles) of 01/PEME or dl1520 was initiated 7 days after cell injection, with dosing for 5 consecutive days. There were 8 mice in each treatment group. Tumor size was measured one time per week over the following 4 weeks until vehicle treated control animals became moribund due to cachexia. For each treatment group the percent of tumor size inhibition relative to the vehicle treated group was plotted from tumor sizes measured on day 35. The results of these experiments are presented in graphical form in FIG. 12 of the attached drawings. Treatment of tumors with 01/PEME required ~1,000 fold less virus than treatment with dl1520 to achieve 50% tumor inhibition (i.e. 50% reduction in mean tumor size relative to vehicle treated group). On day 35, 8 of 8 mice treated with 1×10$^{10}$ particles 01/PEME were tumor free, whereas, 3 of 8 mice treated with $1\times10^{10}$ particles dl1520 were tumor free. At the dose of $1\times10^8$ particles, 2 of 8 mice treated with 01/PEME were tumor free and no mice treated with dl1520 were tumor free.

Studies were performed with 4 human tumor types to explore the utility of intravenous administration of 01/PEME as an antitumor agent. Human tumor cell lines derived from prostate (PC3), lung (A549), cervical (C33A), and colorectal (SW620) cancer were used to evaluate the effects of 01/PEME administered by the intravenous route.

Figure 13:
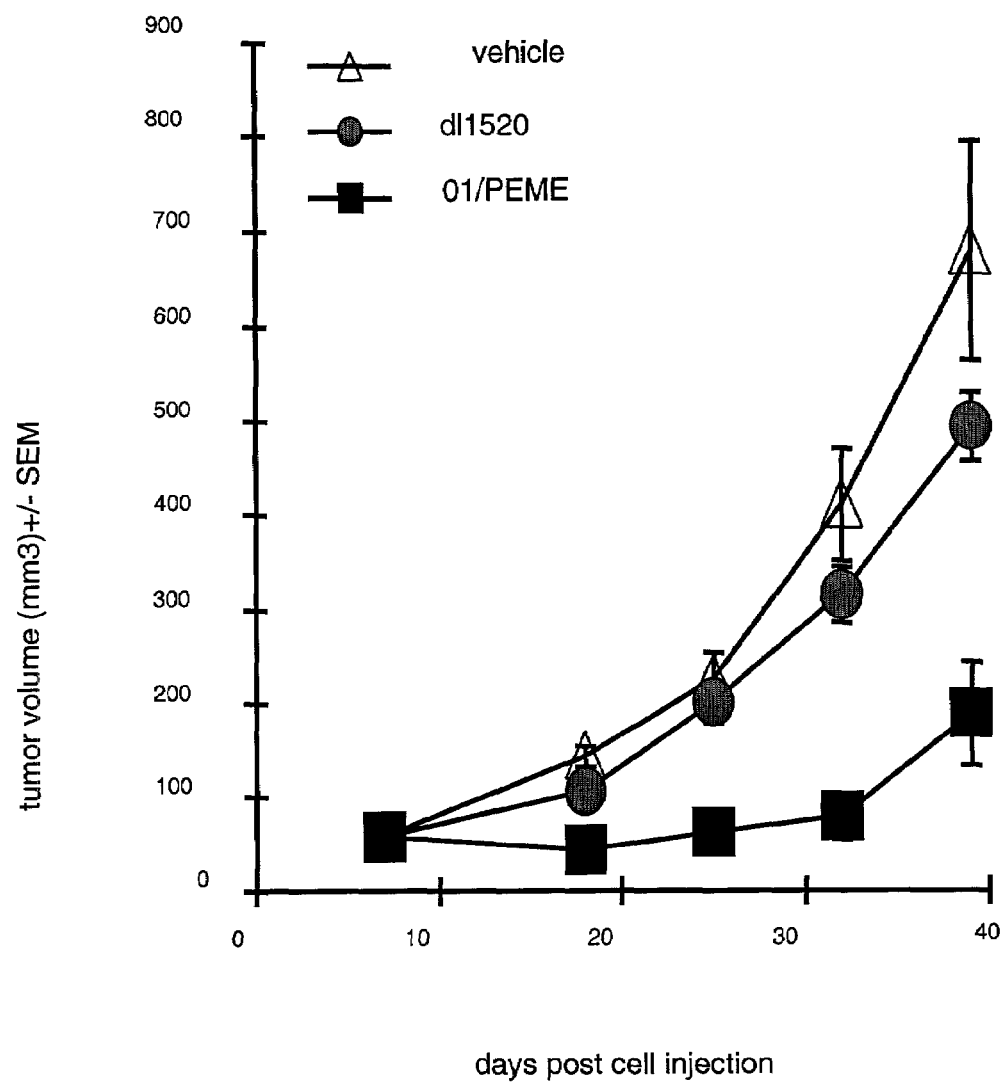
FIG. 13 is a graphical representation of data demonstrating that prostate tumors were inhibited by intravenous delivery of 01/PEME. Nude mice with PC3 subcutaneous tumors were treated by intravenous administration of $1 \times 10^{10}$ particles on 5 consecutive days. Tumor size was plotted over time for each treatment group.

A study was performed to evaluate the effects of intravenous administration of 01/PEME and dl1520 in the PC3 subcutaneous xenograft prostate tumor model. PC3 cells were injected into the flank of female nude mice. Treatment by intravenous administration of $1\times10^{10}$ particles was initiated 7 days after cell injection, with dosing for 5 consecutive days (total dose $5\times10^{10}$ particles). There were 8 mice in each treatment group. Tumor size was measured one time per week over the following 4 weeks until vehicle treated control animals became moribund due to cachexia. The results of these experiments are presented in graphical form in FIG. 13 of the attached drawings. Treatment with 01/PEME inhibited tumor growth by 72% on day 39 relative to the vehicle treated group (p<0.01). The difference in tumor sizes between the vehicle treated group and dl1520 treated group did not achieve statistical significance (p>0.05). Two of 8 animals treated with 01/PEME were tumor free by day 32. These 2 animals have remained tumor free for an additional 7 weeks.

Figure 14:
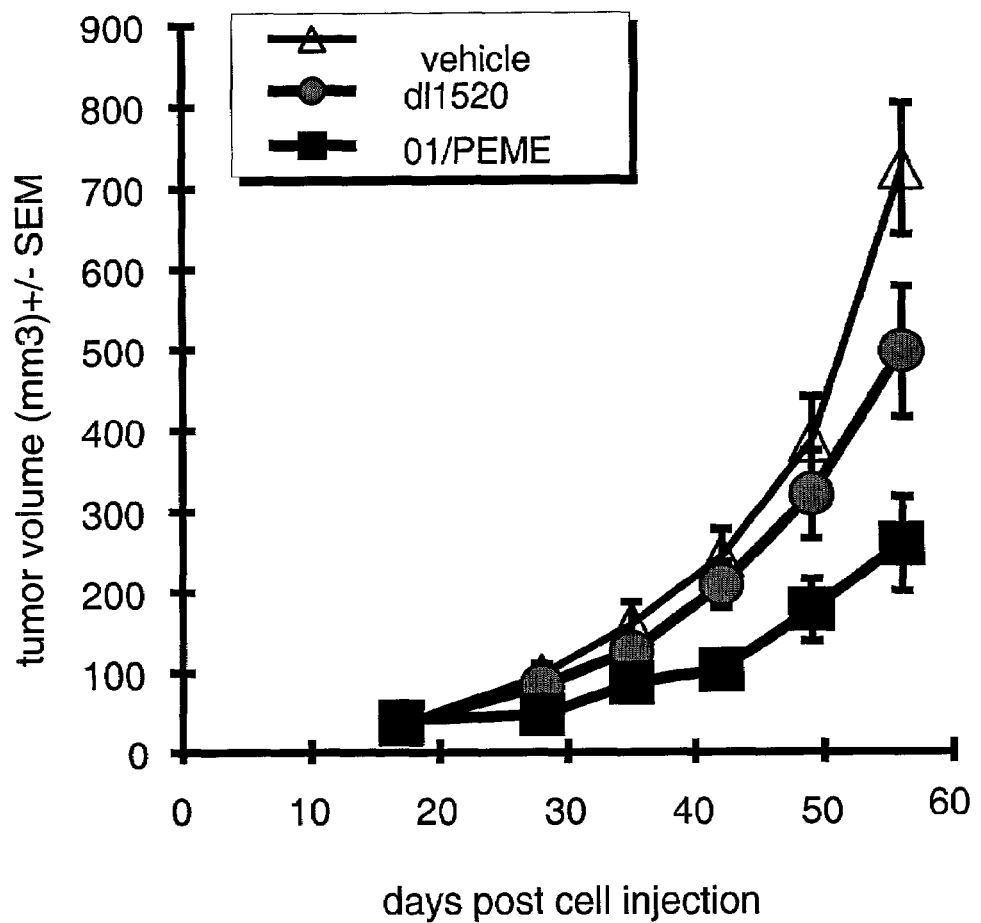
FIG. 14 is a graphical representation of data demonstrating that A549 lung tumors were inhibited by intravenous delivery of 01/PEME. Nude mice with A549 subcutaneous tumors were treated by intravenous administration of $1 \times 10^{10}$ particles on 5 consecutive days. Tumor size was plotted over time for each treatment group.

A second study was performed to evaluate the effects of intravenous administration of 01/PEME and dl1520 in the A549 subcutaneous xenograft lung tumor model. A549 cells were injected into the flank of female nude mice. Treatment by intravenous administration of $1\times10^{10}$ particles was initiated 17 days after cell injection, with dosing for 5 consecutive days (total dose $5\times10^{10}$ particles). There were 8 mice in each treatment group. Tumor size was measured one time per week over the following 5 weeks until vehicle treated control animals became moribund due to tumor size greater than 1000 $mm^3$. The results of these experiments are presented in graphical form in FIG. 14 of the attached drawings. Treatment with 01/PEME inhibited tumor growth by 64% on day 56, respectively, relative to the vehicle treated group (p<0.01). The difference in tumor size between the vehicle treated group and dl1520 treated group did not achieve statistical significance (p>0.05).

Figure 15:
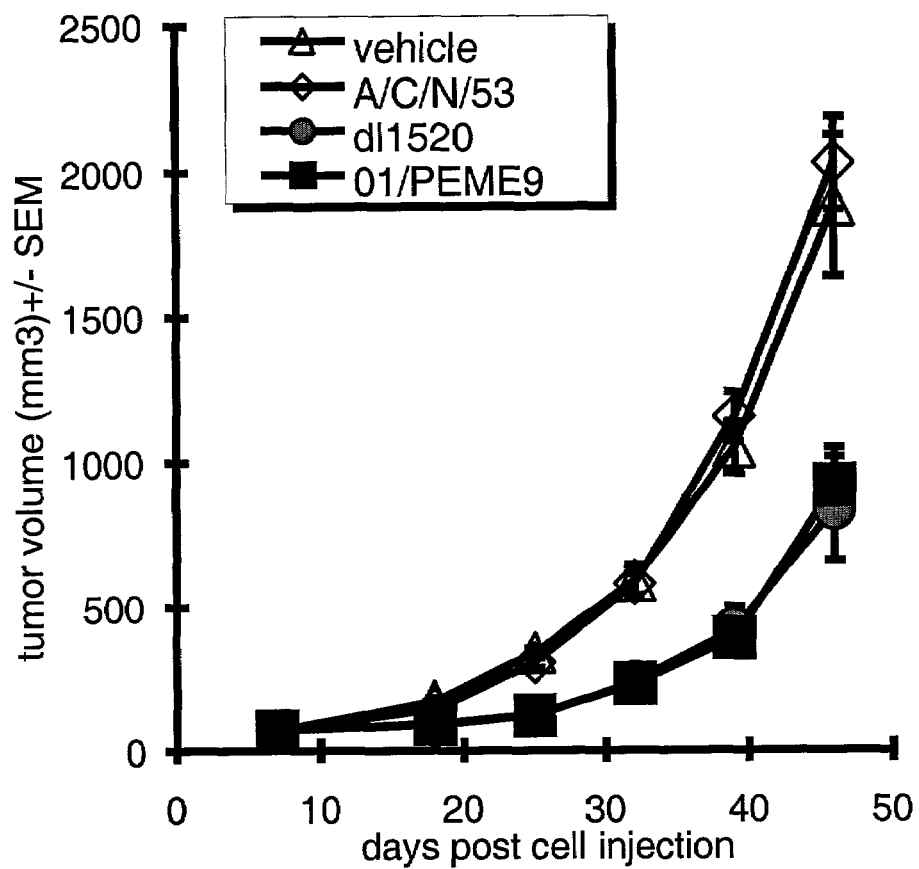
FIG. 15 is a graphical representation of data demonstrating C33A cervical tumors were inhibited by intravenous delivery of 01/PEME. Nude mice with C33A subcutaneous tumors were treated by intravenous administration of $1 \times 10^{10}$ particles on 5 consecutive days. Tumor size was plotted over time for each treatment group.

A third study was performed to evaluate the effect of intravenous administration of 01/PEME, dl1520, and A/C/N/53 in the C33A subcutaneous xenograft cervical tumor model. C33A cells were injected into the flank of female nude mice. Treatment by intravenous administration of $1\times10^{10}$ particles was initiated 7 days after cell injection, with dosing for 5 consecutive days (total dose $5\times10^{10}$ particles). There were 8 mice in each treatment group. Tumor size was measured one time per week over the following 5 weeks until vehicle treated control animals became moribund due to tumor size greater than 1000 $mm^3$. The results of these experiments are presented in graphical form in FIG. 15 of the attached drawings. Treatment with 01/PEME and dl1520 inhibited tumor growth by 51% and 56%, respectively, on day 56 relative to the vehicle treated group (p<0.01). The difference in tumor size between the vehicle treated group and A/C/N/53 treated group did not achieve statistical significance (p>0.05).

Figure 16:
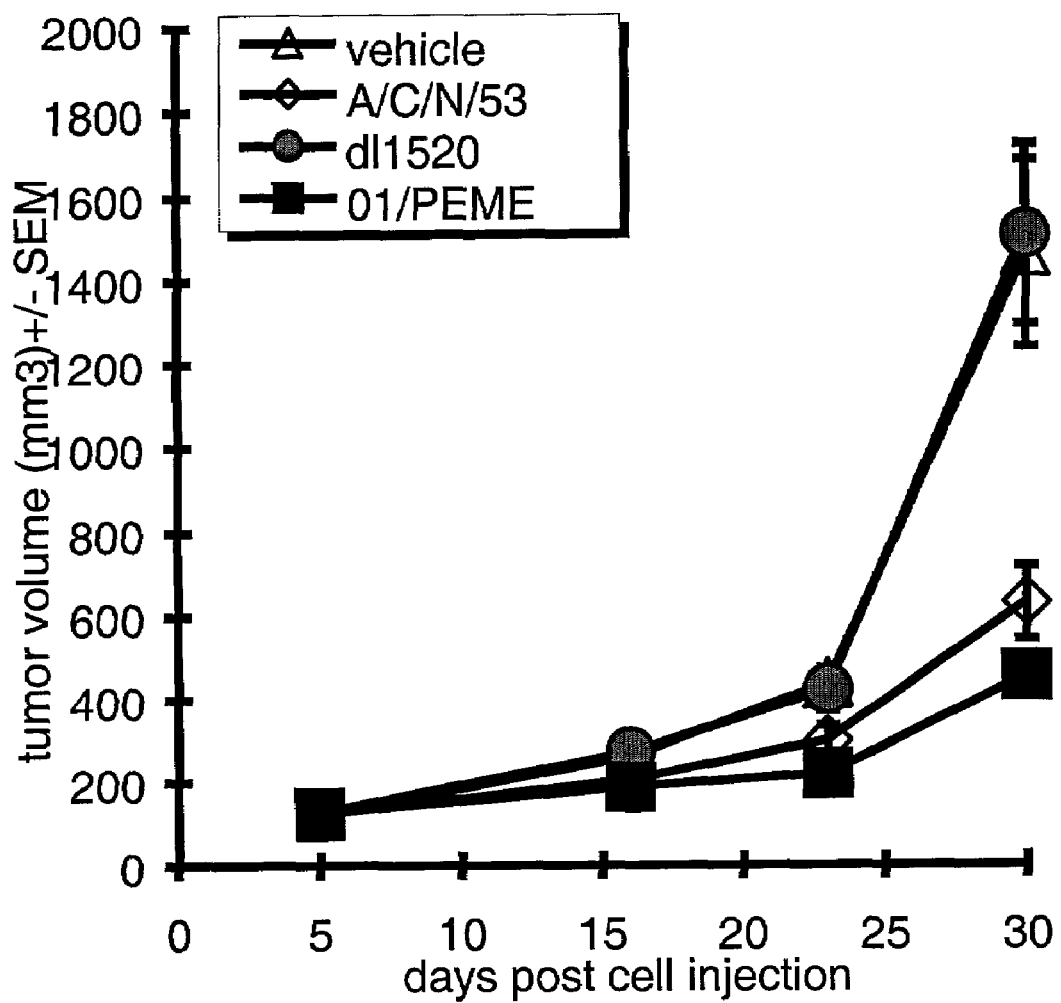
FIG. 16 is a graphical representation of data demonstrating that SW620 colorectal tumors were inhibited by intravenous delivery of 01/PEME. Nude mice with SW620 subcutaneous tumors were treated by intravenous administration of $1 \times 10^{10}$ particles on 5 consecutive days. Tumor size was plotted over time for each treatment group.

A fourth study was performed to evaluate the effect of intravenous administration of 01/PEME, dl1520, and A/C/N/53 in the SW620 subcutaneous xenograft colorectal tumor model. SW620 cells were injected into the flank of female nude mice. Treatment by intravenous administration of $1\times10^{10}$ particles was initiated 5 days after cell injection for 5 consecutive days. There were 8 mice in each treatment group. Tumor size was measured one time per week over the following 3 weeks until vehicle treated control animals became moribund due to tumor size greater than 1000 $mm^3$. The results of these experiments are presented in graphical form in FIG. 16 of the attached drawings. Treatment with 01/PEME and A/C/N/53 inhibited tumor growth by 69% and 57% on day 30 relative to vehicle treated group (p<0.01). The difference in tumor size in the vehicle and dl1520 groups did not achieve statistical significance (p>0.05).

In systemic administration of adenovirus vectors, the presence of circulating neutralizing anti-adenovirus antibodies developed through natural infection has been suggested to be problematic. In order to assess the effective of human anti-adenovirus antibodies on systemic administration, a passive immunization model in SCID/beige was developed using a reporter adenovirus expressing beta-galactosidase (rAd-beta-gal). In this model, the in vitro neutralizing activity of human antibodies used for passive immunization correlated well with inhibition of transduction of the liver following intravenous administration of rAd-beta-gal. In the general population, the neutralizing anti-adenovirus titers varied over a wide range and that based on the in vitro neutralizing antibody results, we predict that the majority (approximately 88% based on these studies) of individuals with anti-adenovirus neutralizing antibodies will be good candidates for systemic adenovirus delivery.

To assess the neutralizing antibody titers of the general population, blood samples from healthy normal blood donors were collected for the study from the San Diego Blood Bank (San Diego, Calif.) at different times (spring, summer, falls, and winter). All 97 serum samples were collected following the San Diego Blood Bank informed consent guideline. Sera were assayed individually for neutralizing activity with the following assay.

Figure 17:
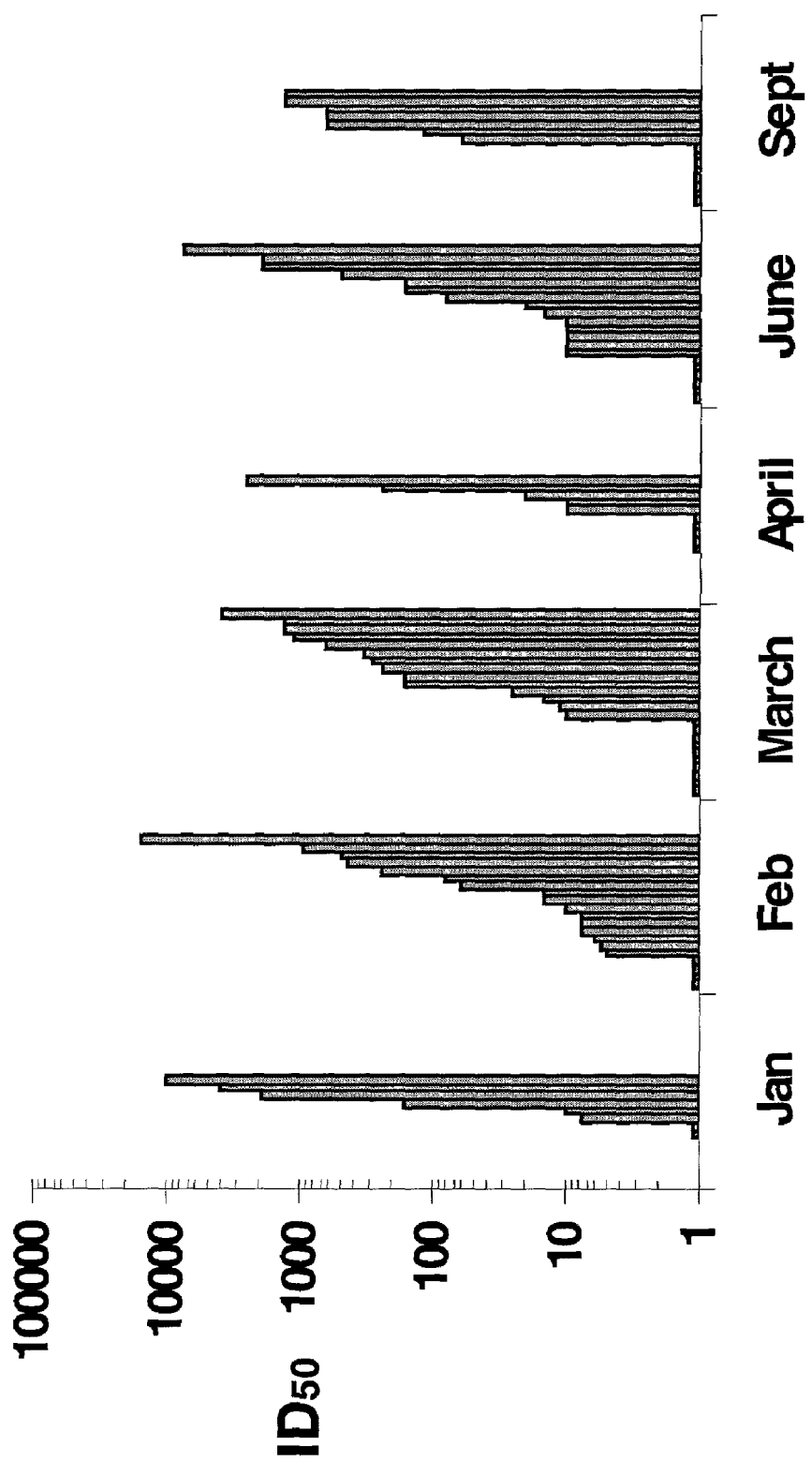
FIG. 17 is a graphical representation of the neutralizing antibody titers determined from 97 healthy blood donors collected at various timepoints throughout the year. ID-50 titers from healthy blood donors were variable between individuals.
Figure 18:
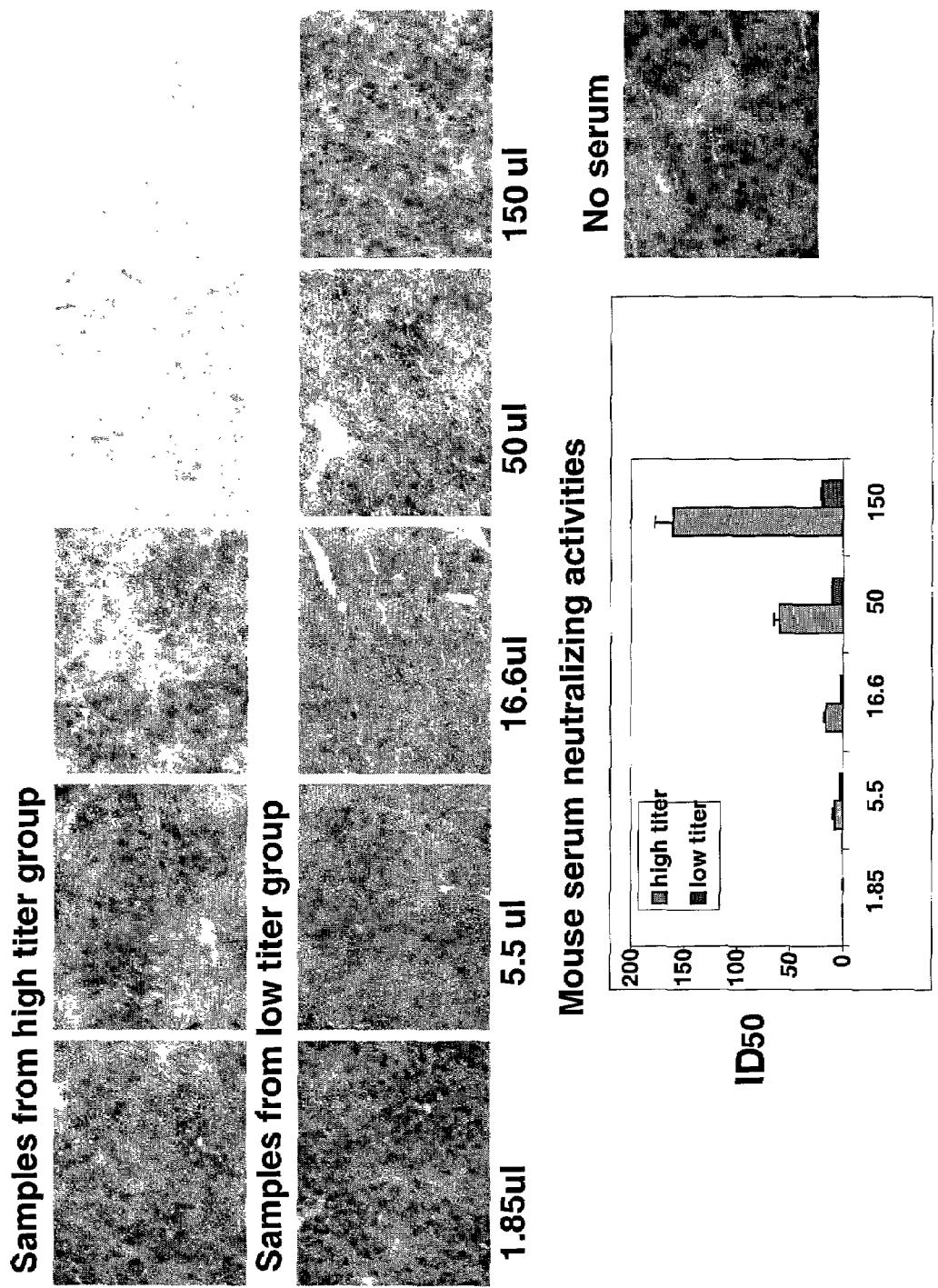
FIG. 18 are photomicrographs of cells stained for beta-galactosidase expression in liver sections of mice injected with rAd-beta-gal. SCID/beige mice were passively immunized with pooled human serum from individuals with high titer (upper panels) or low titer (middle panels). Mice were assayed for neutralizing activity (bar graph) the injected with rAd-beta-gal. Three days later, liver sections were assayed for beta-galactosidase activity (blue) with X-gal substrate

Duplicate two-fold serial dilutions of the serum each serum (starting at 1:20, 1:40, 1:80, etc.) were plated in a 96 well format (60 microliters/well). An E1-region deleted replication deficient recombinant adenoviral vector expressing the green fluorescent protein (GFP) under control of the CMV immediate early promoter (GFCB) was used for detecting transduction. The appropriately diluted serum samples were incubated with equal volumes of GFCB at a final concentration of $4\times10^8$ particles/ml for 1 hr at 37° C. HeLa cells were cultured the day before at $1\times10^4$ cells/well in flat bottom 96 well format. Subsequently, the media from the HeLa cell cultures were removed and 100 microliters of the diluted serum/GFCB mixtures were transferred onto the HeLa cells and were co-incubated overnight. The relative fluorescence was measured the following day on a CytoFluor 4000 Fluorescence Multi-well Plate Reader. Background fluorescence was assessed in wells containing HeLa cells cultured alone, and GFCB fluorescence was determined in wells with HeLa cells cultured with virus in the absence of immune serum. The raw fluorescence numbers were then plotted as % transduction using the following equation: % Transduction=[(Fluorescence Value−Background Fluorescence Value)/(Fluorescence Value of GFCB Control−Background Fluorescence Value)]×100. ID-50 titers were subsequently calculated as the titer at which 50% transduction was observed. The results are presented in FIG. 17 of the attached drawings.

For the passive immunization of human serum, SCID/beige mice were used to avoid possible immune responses toward human serum components. Sera with titers greater than 320 were pooled into a high titer group. Sera with titers less then 320 were pooled into a low titer group. Serum with undetectable titers was not included in the study. Passive immunization was done with 50 microliters of sera (pooled high titer or low titer human serum) diluted to 500 microliters with vPBS, three-fold serial dilutions were made for injection by intraperitoneal route into SCID/beige mice (n=4 for each condition), the following day mice were challenged with $5 \times 10^{10}$ particles of rAd-Bgal, an E1-region deleted adenovirus encoding the beta-galactosidase gene (LacZ) under control of the CMV promoter. The mice were sacrificed 3 days following BGCG challenge and the sera and livers were collected for analysis. Neutralizing activity in the serum samples from the mice was dependent of the volume and titer of the human serum that was adoptively transferred. There was dose dependent inhibition of beta-galactosidase activity in the livers of mice adoptively transferred with human serum samples. Only the 50 and 150 ul volumes of the high titer human serum were capable of inhibiting gene adenovirus delivery. This data suggest that only humans with very high titer samples (10-20% of the population) would adenovirus delivery be inhibited with intravenous administration.

Figure 19:
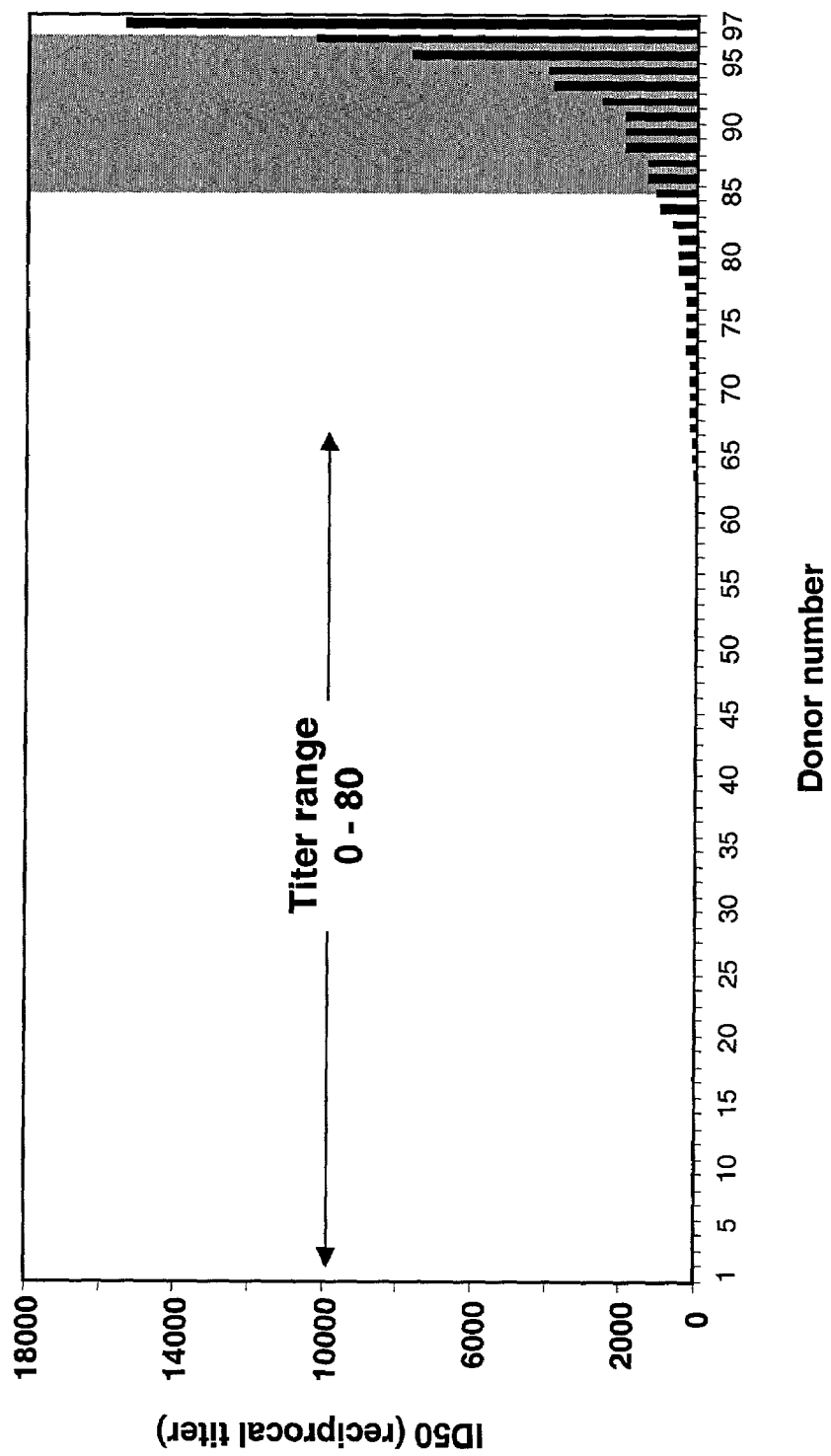
FIG. 19 is a graphical representation of the neutralizing antibody titers determined from 97 healthy blood donors. As can be seen from the data presented, most of the samples have low neutralizing titers.

In summary, the data demonstrates a very good correlation between in vivo transduction efficiency and the titer of neutralizing antibody derived from our in vitro assay. Based on this model, one could predict that approximately 88% of the population would be suitable candidates for systemic adenovirus delivery. (See FIG. 19)

Intravenous administration of non-replicating adenovirus vectors to deliver genes to tumors is limited due to adenovirus distribution to the liver following intravenous administration (Yang, et al. (1994) Immunity 1:433-42.). It is estimated that 90% of the adenovirus delivered to the liver by intravenous administration and virus DNA is rapidly cleared (Schnell, et al. (2001). Mol. Ther. 3:708-22). The advantage of oncolytic replicating adenoviruses would be the ability to start replication at low concentrations in target tissue and increase into therapeutic concentrations. The purpose of this study was to demonstrate replication of 01/PEME in tumor tissue as well as determine the biodistribution of the oncolytic adenovirus, 01/PEME, using intratumoral or intravenous treatment routes in comparison to a nonreplicating adenovirus vector, A/C/N/53.

Figure 20:
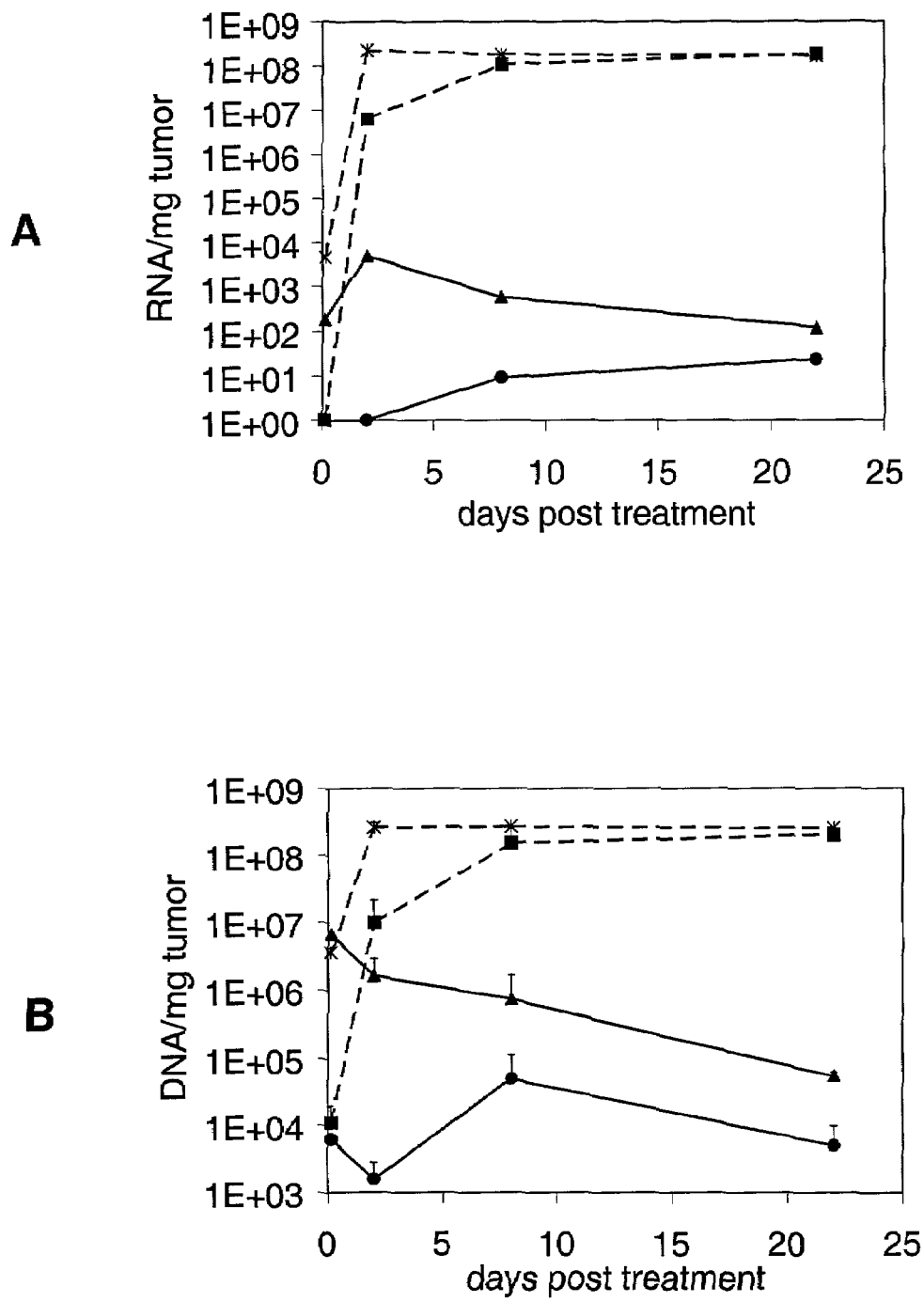
FIG. 20 is a graphical representation of the levels of virus DNA (Panel B) and RNA (Panel A) concentrations in tumor tissue. Concentrations (mean±sd) of virus-DNA, particles/mg of homogenized tumor tissue (Panel B), and hexon RNA, MEQ/mg of tumor tissue, (Panel A) at various time-points after treatment with 01/PEME (dashed lines): iv (■), intratumoral (*); A/C/N/53 (straight lines): iv (●), intratumoral (▲).

Female SCID/beige mice were used. Human lung tumor xenografts (A549 cells) were established (subcutaneous, left flank) and allowed to grow to a volume of ~100 mm$^3$ before treatment was started. 01/PEME or A/C/N/53, at a dose of $5 \times 10^9$ particles, was injected either into the tail vein (200 microliters volume) or intratumoral (100 microliters volume). Two animals per group were sacrificed at 3 hours (0.13 days), 2 days, 8 days, or 22 days after treatment. Tumors and liver-lobes were cut in half; one portion was snap frozen in liquid nitrogen for quantification of virus DNA and RNA by PCR and RT-PCR (Taqman), while the other portion was fixed in formalin for hexon or E1a immunohistochemistry. See FIG. 20.

Similar concentrations of virus DNA were present in the tumor 3 hours (0.13 days) after treatment with both viruses, 01/PEME or A/C/N/53. However, compared to intratumoral administration, over 100-fold less virus DNA (01/PEME or A/C/N/53) was delivered to the tumor by intravenous route. Virus DNA and RNA increased over time in the 01/PEME treatment groups, but not in the A/C/N/53 treatment groups. Within eight days after 01/PEME treatment, concentrations of virus DNA detected in the tumor tissue from intravenous route were equal to concentrations detected in tumors dosed by the intratumoral route. PCR results were confirmed by immunohistochemistry; low levels of viral protein (hexon and E1a) detected 2 and 8 days after treatment increased significantly 22 days after treatment. Hexon positive cells were observed in the tumor tissues from both treatment routes. Hexon and E1a positive staining was detected mainly around necrotic areas of the tumor; hexon was also detected within necrotic tissue.

Figure 21:
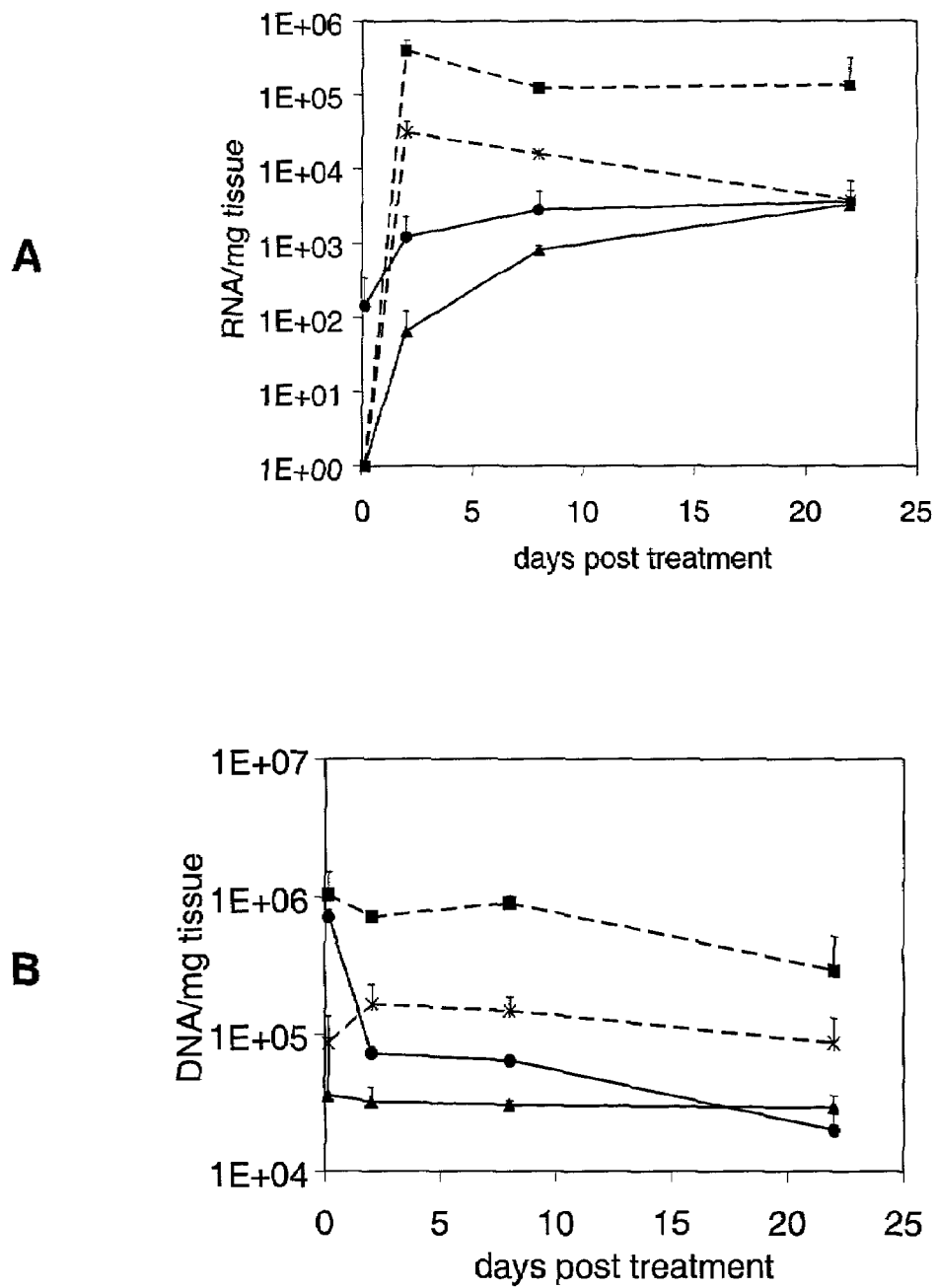
FIG. 21 is a graphical representation of the levels of virus DNA and RNA concentrations in liver tissue. Concentrations (mean±sd) of virus-DNA, particles/mg of homogenized tumor tissue, (Panel B) and hexon RNA, MEQ/mg of tumor tissue, (Panel A) at various time-points after treatment with 01/PEME (dashed lines): iv (■), intratumoral (*); A/C/N/53 (straight lines): iv (●), intratumoral (▲).

Comparable concentrations of virus DNA were detected using PCR analysis of liver homogenates (intravenous administration) 3 hours after treatment with either 01/PEME or A/C/N/53 by the intravenous route. See FIG. 21. But, while virus DNA concentrations decreased over time in the A/C/N/53 group, virus DNA concentrations remained elevated in the 01/PEME treatment group. As expected, less virus DNA was detected in the liver following intratumoral treatment, though concentrations were higher in the 01/PEME group. Immunohistochemistry showed E1a protein, but not hexon protein, in hepatocytes of the 01/PEME treated animals demonstrating adenovirus expression of early viral proteins in mouse liver. A moderate amount of E1a expressing cells (intravenous route) or minimal expression (intratumoral route) in all liver samples harvested at 2, 8, or 22 days after treatment indicated the systemic distribution of infectious virus particles originating from the tumor tissue.

Figure 22:
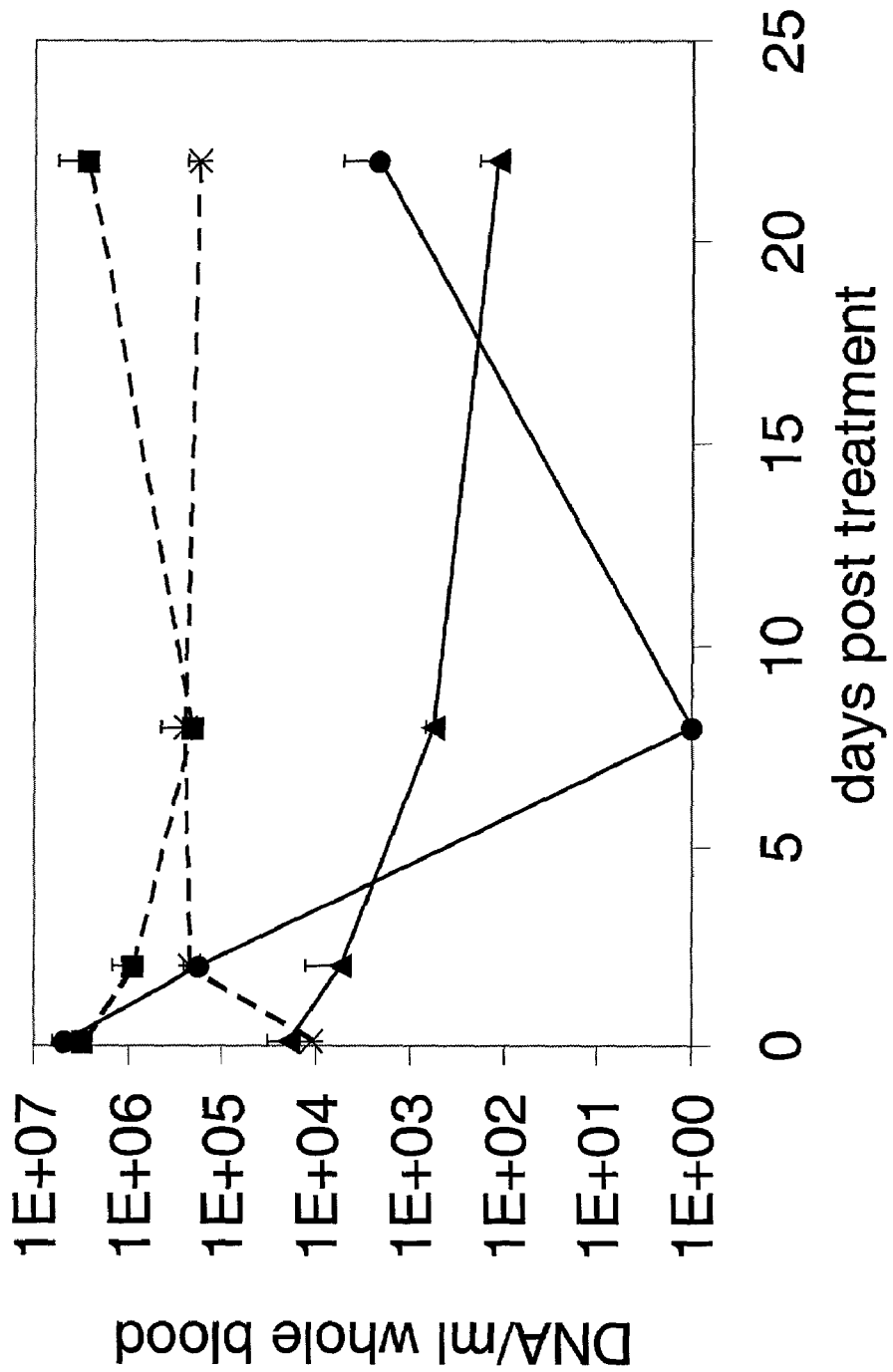
FIG. 22 is a graphical representation of the virus DNA concentrations in whole blood. Concentrations (mean±sd) of virus-DNA (particles/ml whole blood) at various time-points after treatment with 01/PEME (dashed lines): iv (■), intratumoral (*); A/C/N/53 (straight lines): iv (●), intratumoral (▲).

Analysis of blood showed that in contrast to the A/C/N/53 treated groups, in animals treated with 01/PEME virus DNA remained elevated until study end, day 22. See FIG. 22. This suggests that replication of virus in tumor tissue could be monitored by quantification of virus DNA into the blood stream due to apparent leakage of the virus from the tumor site. Comparable indication of replication was observed in the intratumoral treatment group (01/PEME) showing increasing blood virus DNA concentrations from three hours after treatment to two days, followed by persistent elevated virus DNA concentrations.

In summary, an intravenous bolus of 01/PEME was delivered mainly to the liver, but also to tumor tissue in sufficient amounts to support replication such that DNA levels in the tumor tissue to achieve tumor DNA concentrations similar to those obtained with the same dose of 01/PEME injected directly into the tumor. Intratumoral virus replication caused virus to leak into the bloodstream. Analysis of blood concentrations of virus DNA after treatment may be useful as a method to monitor virus replication in clinical studies.

Responses of the host to the introduction of E1a deleted Ad vectors is studied extensively and dependent on the dose of virus, the site of delivery, and the genetic make up of the vector. For example, when administered intravenously into mice, the vast majority of Ad is localized in the liver (Worgall, et al. (1997) Human Gene Therapy 8:37-44). But, when administered intratracheally, lung tissue is infected (Minter, et al. (2000) J. Immunol. 164:443-51). However, independent of the infected tissue, side effects are attributed to the rapid clearance by cellular immune responses including CD8$^+$ and CD4$^+$ cytotoxic T-cells (Kass-Eisler, et al. (1994) Gene Ther 1:395-402; Yang, et al. (1994) Immunity 1:433-42; Schnell, et al. (2001). Mol. Ther. 3:708-22; Tao, et al. (2001). Mol Ther 2001; 3:28-35; Alemany, et al. (2000) J. Gen. Virol. 81:2605-9). Because human replicating adenoviruses infect rodent cells, especially liver tissue (Duncan, et al. (1978) J. Gen. Virol. 40:45-61.), but do not undergo complete replication, the predictive validity of rodent models for toxicity in man is difficult. The availability of various immunodeficient mouse strains allows assessment of pathologic responses to adenoviral early protein expression independent from the immune system mediated clearance. We therefore evaluated the impact of viral protein expression on liver toxic effects in mice.

Different mouse strains, including female BALB/c mice, female nude mice, or female SCID/beige mice were used. PB55, a replicating adenovirus, similar to dl1520 (Wheeler, et al. (2001). J. Leukoc. Biol. 69:622-30), with a deletion in the E1b55k gene, was injected into the tail vein using a dose of $1\times10^{10}$ particles/animal. Animals were sacrificed 24 hours, after treatment. The livers were harvested, fixed in formalin, and serial sections evaluated for pathology (hematoxylin and eosin) or E1a expression (immunohistochemistry).

BALB/c mice and nude mice tolerated intravenous treatment with the replication competent E1b deleted adenovirus construct (PB55) very well. No liver damage was detected in the BALB/c mice and only mild foci of liver necrosis were detected in the nude mice. In contrast, treatment of SCID/beige mice resulted in death of the animals within 24 hours after treatment caused by severe liver necrosis. Liver necrosis was seen also after high doses of A/C/N/53 (Nielsen, et al. (1998) Human Gene Therapy 9:681-94). E1a staining revealed abundant E1a expression in hepatocytes of SCID/beige mice, while only minimal E1a expression was detected in the liver sections of nude mice, and no expression detected in the livers of BALB/c mice. Since most E1a expression was detected in the livers of SCID/beige mice this mouse strain was chosen for further tolerability studies.

TABLE 7

Mouse Strain Background Properties

| strain | genetic background | immune responses to rAd | liver pathology | E1a-expression |
|---|---|---|---|---|
| BALB/c | immune competent | complete immune response | no visible pathology | — |
| nude | T-cell deficient | B/NK cell responses | no visible pathology | + |
| SCID/beige | T, B, and NK cell deficient | macrophages | severe hemorrhagic liver necrosis | +++ |

The different mouse strains were injected with a single bolus of PB55 ($1\times10^{10}$ particles/animal); liver tissue was harvested 24 hours for pathologic evaluation; sections were also evaluated for E1a by immunohistochemistry. E1a positive cells were scored: (−) no E1a positive cell detected; (+) minimal number of cells detected; (++) multiple cells detected; (+++) abundant cells positive for E1a.

Figure 23:
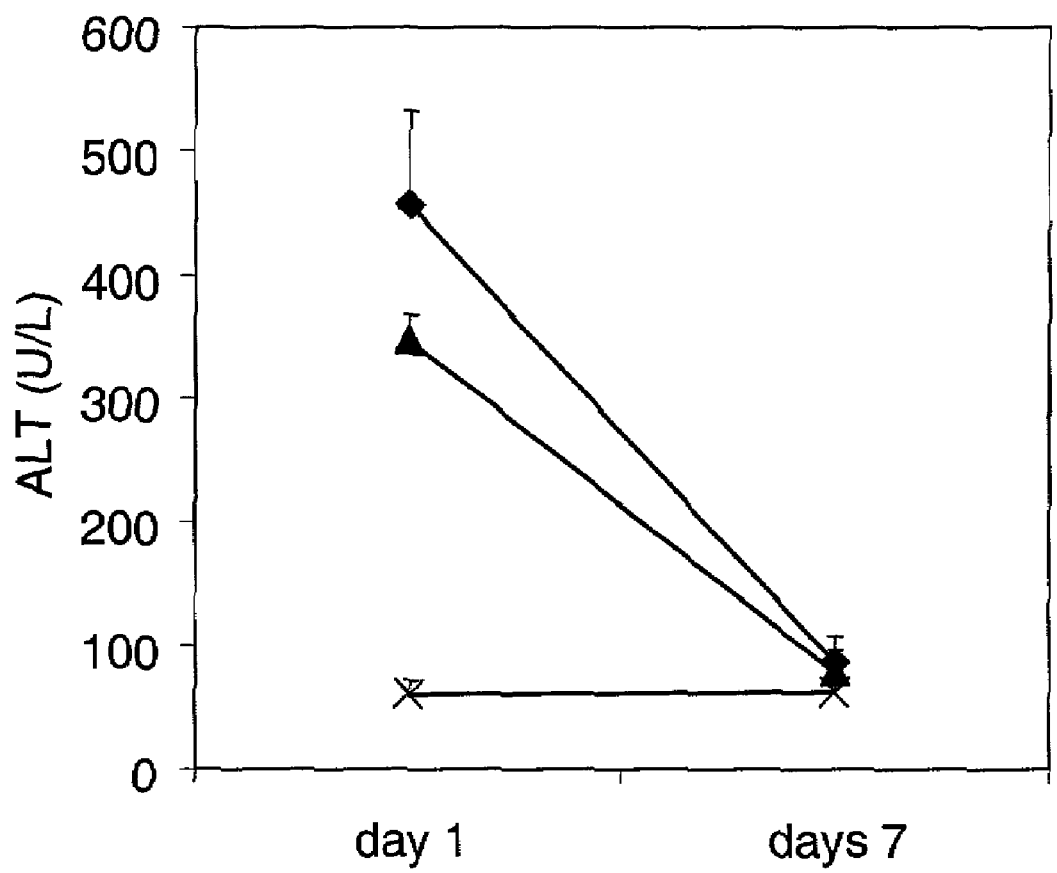
FIG. 23 is a graphical representation of the transaminase levels in sera from animals dosed with adenovirus. Sera from the same animals were analyzed for transaminases (ALT) using the CobasMira autoanalyzer. ALT levels (U/L) are shown on day 1 and days 7 after treatment with dl309 (♦), dl1520 (▲), or ZZCB (×). Shown are the means (n=3) and standard deviation. Serum ALT in untreated: 28±12 U/L. Decreases in serum ALT were significant ($p<0.05$) on day 7 after treatment compared to 1 day after treatment
Figure 24:
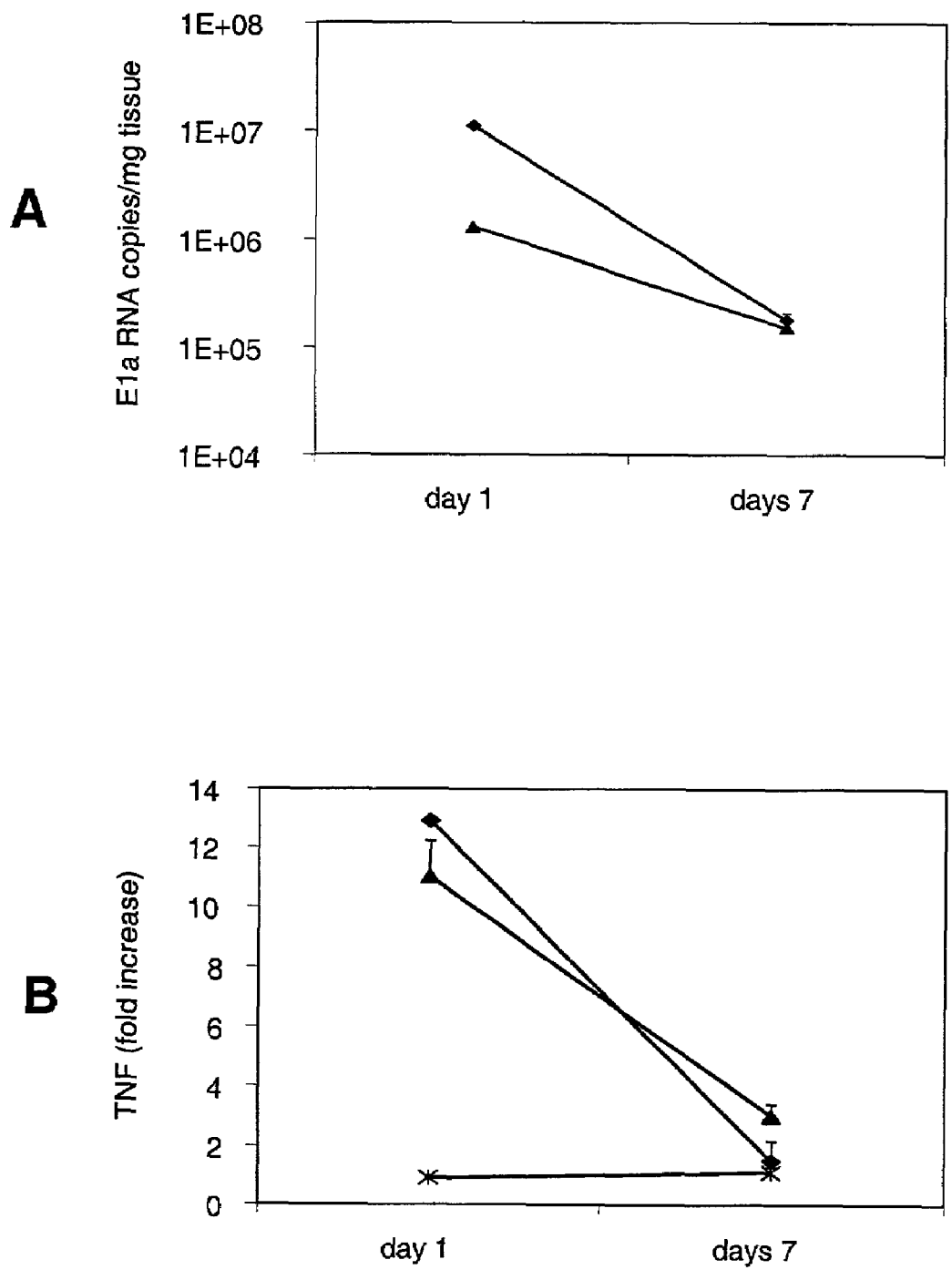
FIG. 24 is a graphical representation of RNA levels in mouse livers after adenovirus dosing. Livers from the animals treated with dl309 (♦), dl1520 (▲), or ZZCB (×) at a dose of $5\times10^9$ particles/animal were homogenized and E1a-RNA, copies/mg of liver tissue, (left panel) or TNFa-RNA, fold increase of TNFa compared to untreated animals, (right panel) analyzed by Taqman. Shown are the means (n=3) and standard deviation. Drop in TNFa (dl309 and dl1520 groups) was significant on day 7 after treatment compared to day 1 after treatment ($p<0.05$).

Female SCID/beige mice were used. Adenoviruses dl309, a replicating adenovirus with a deletion in the E3 region; parent virus to 01/PEME and dl1520, dl1520, a replicating adenovirus with a deletion in the E1b55k gene, or ZZCB, a replication incompetent adenovirus vector with no expression cassette, were injected into the tail vein using doses of $5\times10^9$, or $5\times10^8$ particles/animal; 3 animals served as untreated controls. Animals were sacrificed 1 day or 7 days after treatment. Whole blood was collected for transaminase analysis. Pieces of all major liver lobes were formalin fixed for pathologic evaluation or E1a expression. The other portion of the entire liver was snap-frozen for E1a and TNF-beta RNA analysis in the liver homogenates. See FIG. 23. At a dose of $5\times10^9$ particles/animal, dl309 and dl1520 caused transaminase levels to increase rapidly within 24 hours after treatment that started to resolve within 7 days. At a dose of $5\times10^8$ particles/animal serum transaminases remained normal over the time-period tested. The pattern of transaminases correlated well with E1a expression and tissue TNF• upregulation, thus suggesting a role for early viral gene expression in the observed death of hepatocytes. In this experiment, at 24 hours after treatment, transaminases peaked but resolved within 7 days after treatment. Early acute liver toxicities after E1a competent virus treatment seemed more pronounced than CTL responses observed with E1a deleted adenoviruses in immune competent animals (Yang, et al. (1994) Immunity 1:433-42) in which transaminases peak 7-14 days after treatment. No transaminase elevations were detected with ZZCB.

Prior to initiating intravenous efficacy studies, it was important to identify the maximum dose that can be tolerated by the intravenous route in nude mice. The objective of this experiment was to determine the maximum tolerated dose with five daily injections of 01/PEME, an oncolytic adenovirus modified to express an inhibitor of viral replication in normal cells, in comparison to dl1520, an oncolytic adenovirus with a deletion in the E1b55k gene, and ZZCB, an E1-region deleted nonreplicating empty cassette vector, by intravenous administration in nude mice.

Female nude mice were ear-tagged, weighed, and randomly assigned into treatment groups (6 animals/group) to give a similar distribution of body weights in each group. Test articles were dosed by intravenous (tail vein) administration injected once per day for 5 consecutive days at doses of $1\times10^{10}$, $5\times10^{10}$, or $1\times10^{11}$ particles (first dose on day 0). Blood was collected during treatment from subgroup A (n=3) on days 1, 3 and at necropsy on day 7 and subgroup B (n=3) on days 2, 4 and at necropsy on day 14. Blood collected at days 1-4 was assayed for transaminases. At necropsy whole blood, liver, lungs, kidneys, adrenals, ovaries, uterus, heart, and CNS were harvested, formalin fixed and stained for histopathology and for E1a viral gene expression by immunohistochemistry. Hemogram (RBC, WBC, platelets) were determined from whole blood. Transaminases, BUN, bilirubin, albumin, creatinine were assayed from plasma.

Animals in all treatment-groups tolerated the first two doses. Animals treated with dl1520 at a dose of $5\times10^{10}$ or $1\times10^{11}$ particles died before completion of the scheduled 5 doses but all animals tolerated the $1\times10^{10}$ particles dose of dl1520. Treatment with $1\times10^{11}$ particles 01/PEME resulted in deaths of 6/6 animals: 2/6 animals treated with $5\times10^{10}$ particles 01/PEME died, but all animals tolerated the $1\times10^{10}$ particles dose of 01/PEME. No animals treated with ZZCB at any of the dose levels died.

TABLE 8

Observations in mice after intravenous doing with adenovirus.

| group | n | test articles | dose (particle | dead animals (n/6) | number of doses received |
|---|---|---|---|---|---|
| 1 | 6 | 01/PEME | $1\times10^{11}$ | 6/6 | 4 |
| 2 | 6 | 01/PEME | $5\times10^{10}$ | 2/6 | 5 |
| 3 | 6 | 01/PEME | $1\times10^{10}$ | 0/6 | 5 |
| 4 | 6 | dl1520 | $1\times10^{10}$ | 6/6 | 3 |
| 5 | 6 | dl1520 | $5\times10^{10}$ | 6/6 | 4 |
| 6 | 6 | dl1520 | $1\times10^{10}$ | 0/6 | 5 |
| 7 | 6 | ZZCB | $1\times10^{11}$ | 0/6 | 5 |
| 8 | 6 | ZZCB | $5\times10^{10}$ | 0/6 | 5 |
| 9 | 6 | ZZCB | $1\times10^{10}$ | 0/6 | 5 |
| 10 | 6 | untreated | — | — | — |

Transaminase concentrations were dramatically elevated on day 2 in the dl1520, $5\times10^{10}$ or $1\times10^{11}$ particles doses; as noted above each of these animals died. Animals treated with $1\times10^{10}$ particles dl1520 had transaminase levels within the normal range. Animals treated with 01/PEME at the $5\times10^{10}$ or $1\times10^{11}$ particles doses had elevated transaminase concentrations but the peak concentration was less than was observed with dl1520 treatment. Transaminase concentrations remained with the normal range at the $1\times10^{10}$ particles dose of 01/PEME. Elevated transaminase concentrations were observed later in the time course with ZZCB treatment groups at $5\times10^{10}$ or $1\times10^{11}$ particles. As in treatment with dl1520 or 01/PEME, treatment with $1\times10^{10}$ particles ZZCB did not increase transaminase concentrations. At $1\times10^{10}$ dose or 01/PEME no changes from normal were observed in any of the other parameters tested (RBC, WBC, platelet, BUN, bilirubin, albumin, creatinine).

All the animals that died prior to the completion of scheduled dosing showed severe hepatotoxicity (severe hepatocellular hypertrophy, apoptosis, and increased numbers of mitotic figures). Side effects attributable to liver toxicity also were seen in the medium and high dose treatment groups. As seen with E1a deleted adenoviruses also (Tao, et al. (2001). Mol Ther 2001; 3:28-35) in some livers, lymphoid hyperplasia was present in sections of the spleen (medium, high dose). At the low dose, $1\times10^{10}$ particles, livers and spleens (01/PEME and dl1520) were normal. No histopathologic changes were detected in sections from kidneys, hearts, CNS, lungs, intestine, ovaries and uteri (all treatment groups).

E1a expression was detected in the liver sections of the 01/PEME and dl1520 treated animals on day 7. Fewer cells were E1a positive on day 14. Expression was also detected in the spleens and adrenal glands.

Pharmaceutical Formulations

The present invention further provides a pharmaceutically acceptable formulation of the recombinant viruses in combination with a carrier. The vectors of the present invention may be practice formulated for dose administration in accordance with conventional pharmaceutical with the addition of carriers and excipients. Dosage formulations may include intravenous, intratumoral, intramuscular, intraperitoneal, topical, matrix or aerosol delivery.

The term "carrier" refers to compounds commonly used on the formulation of pharmaceutical compounds used to enhance stability, sterility and deliverability of the therapeutic compound. When the virus is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorption monolaurate, triethanolamine oleate, etc.

The present invention further provides pharmaceutical formulations of the viruses of the present invention with a carrier and a delivery enhancing agent(s). The terms delivery enhancers" or "delivery enhancing agents" are used interchangeably herein and includes one or more agents which facilitate uptake of the virus into the target cell. Examples of delivery enhancers are described in co-pending U.S. patent application Ser. Nos. 09/112,074 filed Jul. 8, 1998 and 08/938,089 filed Sep. 26, 1997. Examples of such delivery enhancing agents include detergents, alcohols, glycols, surfactants, bile salts, heparin antagonists, cyclooxygenase inhibitors, hypertonic salt solutions, and acetates. Alcohols include for example the aliphatic alcohols such as ethanol, N-propanol, isopropanol, butyl alcohol, acetyl alcohol. Glycols include glycerine, propyleneglycol, polyethyleneglycol and other low molecular weight glycols such as glycerol and thioglycerol. Acetates such as acetic acid, gluconic acid, and sodium acetate are further examples of delivery-enhancing agents. Hypertonic salt solutions like 1M NaCl are also examples of delivery-enhancing agents. Examples of surfactants are sodium dodecyl sulfate (SDS) and lysolecithin, polysorbate 80, nonylphenoxypolyoxyethylene, lysophosphatidylcholine, polyethyleneglycol 400, polysorbate 80, polyoxyethylene ethers, polyglycol ether surfactants and DMSO. Bile salts such as taurocholate, sodium tauro-deoxycholate, deoxycholate, chenodesoxycholate, glycocholic acid, glycochenodeoxycholic acid and other astringents such as silver nitrate may be used. Heparin-antagonists like quaternary amines such as protamine sulfate may also be used. Cyclooxygenase inhibitors such as sodium salicylate, salicylic acid, and non-steroidal antiinflammatory drug (NSAIDS) like indomethacin, naproxen, diclofenac may be used. Delivery-enhancing agents includes compounds of the Formula I:

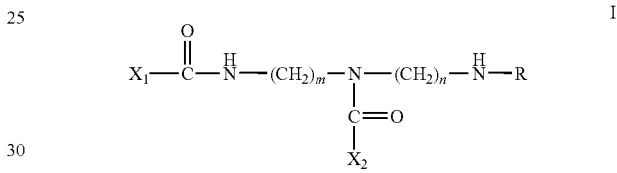

wherein X1 and X2 are selected from the group consisting of a cholic acid group, a deoxcholic acid group and a saccharide group, m is an integer from 2 to 8 and preferably 2 or 3, n is an integer from 2 to 8 and preferably 2 or 3, and R is a cationic group, a saccharide group or a structure —CO—X3 wherein X3 is a saccharide group. The saccharide group may be selected from the group consisting of pentose monosaccharide groups, hexose monosaccharide groups, pentose-pentose disaccharide groups, hexose-hexose disaccharide groups, pentose-hexose disaccharide groups, and hexose-pentose disaccharide groups.

The term "detergent" includes anionic, cationic, zwitterionic, and nonionic detergents. Exemplary detergents include but are not limited to taurocholate, deoxycholate, taurodeoxycholate, cetylpyridium, benalkonium chloride, Zwittergent ZWITTERGENT™ 3-14 detergent, CHAPS (3-[(3-Cholamidopropyl) dimethylammoniol]-1-propanesulfonate hydrate), Big CHAP, Deoxy Big CHAP, TRITON-X-100™ detergent, C12E8, Octyl-B-D-Glucopyranoside, PLURONIC-F68™ detergent, TWEEN 20™ detergent, and TWEEN 80™ detergent (CalBiochem Biochemicals).

Unit dosage formulations of the present invention may be included in a kit of products containing the recombinant virus of claim 1 in lyophilized form and a solution for reconstitution of the lyophilized product. Recombinant viruses of the present invention may be lyophilized by conventional procedures and reconstituted.

The vectors of the present invention may also be administered in combination with calpain inhibitors. The "calpain inhibitor" (abbreviated "CI") refers to a compound which inhibits the proteolytic action of calpain-I, e.g. μ-calpains. The term calpain inhibitors as used herein includes those compounds having calpain I inhibitory activity in addition to or independent of their other biological activities. A wide variety of compounds have been demonstrated to have activity in inhibiting the proteolytic action of calpains. Examples of calpain inhibitors are useful in the practice of the present invention include N-acetyl-leu-leu-norleucinal also known as "calpain inhibitor 1." Calpain inhibitors have been observed to increase infectivity of cells with respect to viral vectors, to enhance transcription from promoters by increasing levels of NF-kappaB and AP-1 transcription factors and to diminish the CTL response to adenoviral vectors. Consequently, the formulations and methods of the present invention may optionally include calpain inhibitors. Calpain inhibitors and their applications are described in Atencio, et al. co-pending U.S. patent application Ser. Nos. 60/104,321 and 09/073,076 filed Oct. 15, 1998.

Methods of Use

The present invention provides a method of killing a cell with a regulatory pathway defect by contacting the target cell with a selectively replicating vector of the present invention. In one embodiment of the invention as exemplified herein, the cell containing a pathway defect is a neoplastic cell. The term "neoplastic cell" is a cell displaying an aberrant growth phenotype characterized by independence of normal cellular growth controls. As neoplastic cells are not necessarily replicating at any given time point, the term neoplastic cells comprise cells which may be actively replicating or in a temporary non-replicative resting state (G1 or G0). Localized populations of neoplastic cells are referred to as neoplasms. Neoplasms may be malignant or benign. Malignant neoplasms are also referred to as cancers. The term cancer is used interchangeably herein with the term tumor. Neoplastic transformation refers the conversion of a normal cell into a neoplastic cell, often a tumor cell.

The present invention provides a method of ablating neoplastic cells in a mammalian organism in vivo by the administration of a pharmaceutically acceptable formulation of the recombinant adenovirus of the present invention. The term "ablating" means the substantial reduction of the population of viable neoplastic cells so as to alleviate the physiological maladictions of the presence of the neoplastic cells. The term "substantial" means a reduction in the population of viable neoplastic cells in the mammalian organism by greater than approximately 20% of the pretreatment population. The term "viable" means having the uncontrolled growth and cell cycle regulatory characteristics of a neoplastic cell. The term "viable neoplastic cell" is used herein to distinguish said cells from neoplastic cells which are no longer capable of replication. For example, a tumor mass may remain following treatment, however the population of cells comprising the tumor mass may be dead. These dead cells have been ablated and lack the ability to replicate, even though some tumor mass may remain.

The term "mammalian organism" includes, but is not limited to, humans, pigs, horses, cattle, dogs, cats. Preferably one employs an adenoviral vector endogenous to the mammalian type being treated. Although it is generally favored to employ a virus from the species to be treated, in some instances it may be advantageous to use vectors derived from different species which possess favorable pathogenic features. For example, it is reported (WO 97/06826 published Apr. 10, 1997) that ovine adenoviral vectors may be used in human gene therapy to minimize the immune response characteristic of human adenoviral vectors. By minimizing the immune response, rapid systemic clearance of the vector is avoided resulting in a greater duration of action of the vector.

The vectors of the present invention are particularly applicable to the treatment of tumors associated with a lack of TGF-β antiproliferative action including but not limited to breast carcinomas, hepatomas, gastric, colon and skin tumors, as well as B and T lymphomas (Markowitz and Roberts, 1996). Mutations of type II TGF-β receptor have been identified in colon, gastric, head and neck squamous carcinomas. Mutations or deletions of type I receptors have also been found in Kaposi's sarcoma, breast, ovarian and colorectal tumors. Among the intracellular effectors of TGF-β signaling, Smads, Smad4/DPC4 was identified as a candidate tumor suppressor genes that was altered in nearly 50% of the pancreatic cancers. Alteration of DPC4 gene has also been found in colon, breast and ovarian tumors although at much lower frequency. The vectors of the present invention are particularly applicable to the treatment of TGF-β insensitive tumors such as pancreatic cancer.

The vectors of the present invention are also applicable to the treatment of tumor cells containing p53-pathway defects. These tumors include those possessing alterations in p53, mdm2 and p14/p19ARF (INK4a gene). The vectors of the present invention are also useful in treating cancer cells with Rb pathway defects. Rb pathway defects result from alterations in Rb, cyclin D, cyclin dependent kinase (such as CDK4) and p16 (INK4a gene).

While the present invention provides a method of use of the recombinant adenoviruses alone, the recombinant adenoviruses of the present invention and formulations thereof may be employed in combination with conventional chemotherapeutic agents or treatment regimens. Examples of such chemotherapeutic agents include inhibitors of purine synthesis (e.g., pentostatin, 6-mercaptopurine, 6thioguanine, methotrexate) or pyrimidine synthesis (e.g. Pala, azarbine), the conversion of ribonucleotides to deoxyribonucleotides (e.g. hydroxyurea), inhibitors of dTMP synthesis (5-fluorouracil), DNA damaging agents (e.g. radiation, bleomycines, etoposide, teniposide, dactinomycine, daunorubicin, doxorubicin, mitoxantrone, alkylating agents, mitomycin, cisplatin, procarbazine) as well as inhibitors of microtubule function (e.g vinca alkaloids and colchicine). Chemotherapeutic treatment regimens refers primarily to non-chemical procedures designed to ablate neoplastic cells such as radiation therapy. Examples of combination therapy when the therapeutic gene is p53 are described in Nielsen, et al. WO/9835554A2 published Aug. 20, 1998.

The immunological response is significant to repeated in vivo administration of viral vectors. Consequently, the vectors of the present invention may be administered in combination with immunosuppressive agents. Examples of immunosuppressive agents include cyclosporine, azathioprine, methotrexate, cyclophosphamide, lymphocyte immune globulin, antibodies against the CD3 complex, adrenocorticosteroids, sulfasalzaine, FK-506, methoxsalen, and thalidomide.

The present invention also provides a method of ablating neoplastic cells in a population of normal cells contaminated by said neoplastic cells ex vivo by the administration of a recombinant adenovirus of the present invention to said population. An example of the application of such a method is currently employed in ex vivo applications such as the purging of autologous stem cell products commonly known as bone marrow purging. The term "stem cell product" refers to a population of hematopoietic, progenitor and stem cells capable of reconstituting the long term hematpoietic function of a patient who has received myoablative therapy. Stem cell products are conventionally obtained by apheresis or mobilized or non-mobilized peripheral blood. Apheresis is conventionally achieved through the use of known procedures using commercially available apheresis apparatus such as the COBE Spectra Apheresis System, commercially available from COBE International, 1185 Oak Street, Lakewood, Colo. It is preferred that treatment conditions be optimized to achieve a "3-log purge" (i.e. removal of approximately 99.9% of the tumor cells from the stem cell product) and most preferably a "5-log purge" (removal of approximately 99.999% of tumor cells from the stem cell product). In the preferred practice of the invention, a stem cell product of 100 ml volume would be treated at a particle number to nucleated cell ratio of approximately $2 \times 10^{11}$ of the vectors of the present invention for a period of approximately 4 hours at 37 C.

Diagnostic Applications

In addition to therapeutic applications described above, the vectors of the present invention are also useful for diagnostic purposes. For example, the vectors of the present invention may incorporate a reporter gene which is expressed upon viral infection or replication. The term "reporter gene" refers to a gene whose product is capable of producing a detectable signal alone or in combination with additional elements. Examples of reporter genes includes the β-galactosidase gene, the luciferase gene, the green fluorescent protein gene, nucleotide sequences encoding proteins detectable by imaging systems such as X-rays or magnetic field imaging systems (MRI). Such vectors would be useful to detect the presence of a functional pathway (e.g. p53 or TGF-beta pathway. Alternatively, such vectors may also be employed to express a cell surface protein capable of recognition by a binding molecule such as a fluorescently labelled antibody. Alternatively where the pathway-responsive promoter is used to drive a repressor of viral replication (e.g E2F-Rb) late viral promoters (for example E2 which is turned off by E2F-Rb or any other promoter with repressor binding sites for example E2F binding sites) could be used to drive the reporter gene for diagnostic applications where the pathway-responsive promoter is off. These diagnostic constructs may be used for diagnostic purposes in vivo or in vitro. Examples of in vivo applications include imaging applications such as X-ray, CT scans or Magnetic Resonance Imaging (MRI).

Methods of Preparing The Vectors

The present invention further provides a method of producing the recombinant viruses described above, said method comprising the steps of:
 a. infecting a producer cell with a recombinant virus
 b. culturing said infected producer cell under conditions so as to permit replication of the viral genome in the producer cell,
 c. harvesting the producer cells, and
 d. purifying the recombinant virus.

The term "infecting" means exposing the recombinant virus to the producer cell under conditions so as to facilitate the infection of the producer cell with the recombinant adenovirus. In cells which have been infected by multiple copies of a given virus, the activities necessary for viral replication and virion packaging are cooperative. Thus, it is preferred that conditions be adjusted such that there is a significant probability that the producer cells are multiply infected with the virus. An example of a condition which enhances the production of virus in the producer cell is an increased virus concentration in the infection phase. However, it is possible that the total number of viral infections per producer cell can be overdone, resulting in toxic effects to the cell. Consequently, one should strive to maintain the infections in the virus concentration in the range of $1 \times 10^6$ to $1 \times 10^{10}$, preferably about $1 \times 10^9$, virions per ml. Chemical agents may also be employed to increase the infectivity of the producer cell line. For example, the present invention provides a method to increase the infectivity of producer cell lines for viral infectivity by the inclusion of a calpain inhibitor. Examples of calpain inhibitors useful in the practice of the present invention include calpain inhibitor 1 (also known as N-acetyl-leucyl-leucyl-norleucinal, commercially available from Boehringer Mannheim). Calpain inhibitor 1 has been observed to increase the infectivity of producer cell lines to recombinant adenovirus.

The term "producer cell" means a cell capable of facilitating the replication of the viral genome of the recombinant adenovirus to be produced. A variety of mammalian cell lines are publicly available for the culture of recombinant adenoviruses. For example, the 293 cell line (Graham and Smiley (1977) J. Gen. Virol. 36:59-72) has been engineered to complement the deficiencies in E1 function and is a preferred cell line for the production of the current vectors. Examples of other producer cells include HeLa cells, PERC.6 cells (as described in publication WO/97/00326, application serial No. PCT/NL96/00244.

The term "culturing under conditions to permit replication of the viral genome" means maintaining the conditions for the infected producer cell so as to permit the virus to propagate in the producer cell. It is desirable to control conditions so as to maximize the number of viral particles produced by each cell. Consequently it will be necessary to monitor and control reaction conditions such as temperature, dissolved oxygen, pH, etc. Commercially available bioreactors such as the CelliGen Plus CELLIGEN PLUS™ Bioreactor (commercially available from New Brunswick Scientific, Inc. 44 Talmadge Road, Edison, N.J.) have provisions for monitoring and maintaining such parameters. Optimization of infection and culture conditions will vary somewhat, however, conditions for the efficient replication and production of virus may be achieved by those of skill in the art taking into considerations the known properties of the producer cell line, properties of the virus, type of bioreactor, etc. When 293 cells are employed as the producer cell line, oxygen concentration is preferably maintained from approximately 50% to approximately 120% dissolved oxygen, preferably 100% dissolved oxygen. When the concentration of viral particles (as determined by conventional methods such as HPLC using a Resource Q column) begins to plateau, the reactor is harvested.

The term "harvesting" means the collection of the cells containing the recombinant adenovirus from the media. This may be achieved by conventional methods such as differential centrifugation or chromatographic means. At this stage, the harvested cells may be stored or further processed by lysis and purification to isolate the recombinant virus. For storage, the harvested cells should be buffered at or about physiological pH and frozen at −70 C.

The term "lysis" refers to the rupture of the producer cells. Lysis may be achieved by a variety of means well known in the art. When it is desired to isolate the viral particles from the producer cells, the cells are lysed, using a variety of means well known in the art. For example, mammalian cells may be lysed under low pressure (100-200 psi differential pressure) conditions or conventional freeze thaw methods. Exogenous free DNA/RNA is removed by degradation with DNAse/RNAse.

The term "purifying" means the isolation of a substantially pure population of recombinant virus particles from the lysed producer cells. Conventional purification techniques such as chromatographic or differential density gradient centrifugation methods may be employed. In the preferred practice of the invention, the virus is purified by column chromatography in substantial accordance with the process of Huyghe et al. (1995) *Human Gene Therapy* 6: 1403-1416 as described in co-pending U.S. patent application Ser. No. 08/400,793 filed Mar. 7, 1995 now, U.S. Pat. No. 5,837,520 Shabram, et al. issued Nov. 17, 1998

Additional methods and procedures to optimize production of the recombinant adenoviruses of the present invention are described in co-pending U.S. patent application Ser. No. 09/073,076, filed May 4, 1998 entitled Viral Production Process which is now issued as U.S. Pat. No. 5,994,134 (the entire teaching of which is herein incorporated by reference).

EXAMPLES

The following examples provide the methodology and results of experiments demonstrating the construction of particular recombinant adenoviral and plasmid vectors. It will be apparent to those of skill in the art to which the invention pertains, the present invention may be embodied in forms other than those specifically disclosed in these examples, without departing from the spirit or essential characteristics of the invention. The particular embodiments of the invention described below, are therefore to be considered as illustrative and not restrictive. In the following examples, "g" means grams, "ml" means milliliters, "mol" means moles, "° C." means degrees Centigrade, "min." means minutes, "FBS" means fetal bovine serum, and "PN" refers to number of particles of recombinant virus.

Example 1

Plasmid Constructions p800luc, a plasmid encoding luciferase under the control of 800 bp PAI promoter was obtained from Dr. David Luskutoff (Scripps Institute, LaJolla, Calif.). Plasmid pCTMIE-E2F-Rb that contains a CMV promoter followed by adenovirus-5 tripartite leader sequence and a SV40 enhancer upstream of the coding sequence for E2F-RB fusion protein was provided by Doug Antelman (Canji).

Example 2

Construction Luciferase Plasmids with TGF-β Responsive Promoters

A. PAI-Luciferase Plasmid:

Sequences of all the fragments are shown in 5'-3' direction. A 749 bp fragment flanked with SacI and XhoI sites at 5' and 3' ends respectively, and SV40 TATA box instead of native TATA box within the promoter, was amplified by PCR using p800luc as the template and primers AGT CGA GCT CCA ACC TCA GCC AGA (SEQ ID NO: 1) and GAT CCT CGA GCT CCT CTG TGG GCC ACT GCC TCC TCA TAA ATA CC (SEQ ID NO:2) (containing SV40 TATA box). The resulting PCR product was digested with SacI and XhoI and ligated to a fragment obtained after digesting PGL3-basic, a luciferase construct with no promoter (Promega), to obtain PAI-luciferase.

B. SRE-Luciferase Plasmid:

The following oligonucleotides, GG TAT TTA TGA GGA GGC AGT GGC CCA CAG AGG AGC TCG AGG ATC (SEQ ID NO:3) and GAT CCT CGA GCT CCT CTG TGG GCC ACT GCC TCC TCA TAA ATA CC (SEQ ID NO:4) were annealed. The annealed product was digested with XhoI and ligated to PGL3-basic digested with MluI, blunt-ended with Klenow and digested with XhoI to obtain pSVT-luc (a luciferase construct with SV40 TATA box). Oligonucletides containing Smad4/DPC4 binding sites, CGT CTA GAC GTC TAG ACG TCT AGA CGT CTA GAC TGT AC (SEQ ID NO:5) and AGT CTA GAC GTC TAG ACG TCT AGA CGT CTA GAC GGT AC (SEQ ID NO:6) were annealed and ligated to pSVT-luciferase digested with KpnI to obtain SRE-luciferase plasmid.

Example 3

Construction Luciferase Plasmids with p53-Responsive Promoters

A. RGC-Luciferase Plasmid:

Two complimentary 5'-phosphorylated oligonucleotides containing p53 binding sites from the ribosomal gene cluster, AG AAA AGG CAA GGC CAG GCA AGT CCA GGC AAC TCG TGG TAG (SEQ ID NO:7) and CA CGA GTT GGC TGG ACT TGC CTG GCC TTG CGT TTT CTG TAC (SEQ ID NO:8) were annealed. The annealed fragment was ligated to pSVT-luciferase digested with KpnI to obtain RGC-luciferase plasmid.

B. p53CON-Luciferase Plasmid:

Two complimentary 5'-phosphorylated oligonucleotides containing consensus p53 binding sites (p53CON), CT CGA CGG ACA TGG CCG GGC ATG TCC TCG ACG GAG ATG CCC GGG CAT GTC GTG TAG (SEQ ID NO:9) and AG GAG ATG CCC GGG CAT GTG GGT GGA GGA CAT GCC CGG GCA TGT GCG TCG AGG TAG (SEQ ID NO:10) were annealed. The annealed fragment was ligated to pSVT-luciferase digested with KpnI to obtain p53CON-luciferase plasmid.

C. PAI-E2F-Rb Plasmid

The sequence containing the CMV promoter followed by adenovirus-5 tripartite leader sequence and a SV40 enhancer upstream of the coding sequence for E2F-RB fusion protein in plasmid pCTMIE-E2F-Rb was excised by digesting with BglI and XbaI and the resulting fragment was ligated to obtain the promoter-less E2F-RB plasmid. A fragment containing modified PAI promoter was excised from the plasmid PAI-luciferase by digesting with SacI and XhoI and was blunt ended by treating with Klenow. This fragment was ligated to the promoter-less E2F-RB plasmid that was digested with EcoRI and treated with Klenow fragment of DNA polymerase I to obtain PAI-E2F-RB plasmid.

Example 4

Generation of Recombinant Adenoviruses

A transfer plasmid containing Ad5 sequence with 3-kb deletion in the E3 region, pNEBΔE3, was constructed by cloning a 7.4 kb SnaBI fragment from pBHG11 (26676 to 34140) to pNEB193 (plasmid from NEB) treated with BamHI, AccI and Klenow. A multiple cloning site was introduced to the above plasmid by annealing 5-phosphorylated oligonucleotides, AAA TAG GTA ATG CAT TCT AGA GCG GGC GCT CGC GAG GAT CCT TAA T (SEQ ID NO:11) and TAA GGA TCC TCG CGA GCG GCC GCT CTA GAA TGC ATT ACG TAT TTA T (SEQ ID NO:12) and introducing the annealed fragment by ligating to the PacI digested pNEBΔE3 to obtain pNEBΔE3 (MCS) plasmid.

Transfer plasmid to generate a recombinant adenovirus encoding E2F-Rb under the control of PAI-promoter and enhanced green fluorescent protein (GFP) under the control of CMV promoter was constructed as follows. An intermediate vector pABS.4-E2F-Rb was prepared by ligating a fragment containing PAI promoter and E2F-Rb coding sequence prepared by digesting PAI-E2F-Rb with NacI and XbaI and ligating to pABS.4 plasmid (Microbix) fragment prepared by digesting with KpnI, treating with Klenow and redigesting with XbaI. A fragment containing PAI promoter, E2F-Rb coding sequence and Kanamycin gene was then excised from the plasmid PABS.4-E2F-Rb by digesting with PacI, treated with Klenow and ligated to the plasmid fragment obtained by digesting pNEBΔE3 plasmid with PacI and treating with Klenow to obtain the plasmid pNEBΔE3-PAI-E2F-Rb, with no PacI site. The kanamycin gene in this plasmid was replaced with CMV promoter operably linked to green fluorescent protein (GFP) gene by digesting pNEBΔE3-PAI-E2F-Rb with SwaI and ligating it to a fragment isolated from pEGFP-N (Clontech) by digesting with AflII and SspI and treating with Klenow, to obtain pΔE3-PAI-E2F-Rb-GFP plasmid.

Transfer plasmids to generate recombinant adenoviruses encoding E2F-Rb under the control of a TGF-β responsive promoter with SRE and enhanced green fluorescent protein (GFP) under the control of CMV promoter were constructed as follows. E2F-Rb coding sequence was introduced into the plasmid pNEBΔE3 (MCS) to obtain the plasmid pNEBΔE3-E2F-Rb by ligating a fragment isolated by digesting pNEBΔE3 (MCS) with XbaI and NruI and a fragment generated by digesting pCTMIE-E2F-Rb with XbaI and Nae I. A TGF-β-responsive promoter containing SRE was introduced to the above plasmid by amplifying this sequence by PCR using SRE-luciferase as the template and phosphorylated primers, GTA AGG TGC CAG AAC ATT TCT C (SEQ ID NO:13) and GAT AAC TAG TGC TCC TCT GTG GGC CAC T (SEQ ID NO:14) The resulting PCR product was digested with SpeI and ligated to SnaBI and XbaI digested pNEBΔE3-E2F-Rb to obtain pΔE3-DPC-E2F-Rb.

Transfer plasmids to generate recombinant adenoviruses encoding E2F-Rb under the control of p53 responsive promoters and enhanced green fluorescent protein (GFP) under the control of CMV promoter were constructed as follows, p53-responsive promoter containing p53-binding sites from ribosomal gene cluster or p53 consensus site (p53CON) was introduced to the plasmid pNEBΔE3-E2F-Rb by amplifying the promoter sequence by PCR using RGC-luciferase or p53CON-luciferase as the template and phosphorylated primers, GTA AGG TGC CAG AAC ATT TCT C (SEQ ID NO:15) and GAT ATC TAG ACG TCC TCT GTG GGC CAC T (SEQ ID NO:16). The resulting PCR products were digested with XbaI and ligated to SnaBI and XbaI digested pNEBΔE3-E2F-Rb to obtain pΔE3-RGC-E2F-Rb and pdelataE3-PCON-E2F-Rb.

Example 5

Homologous Recombination to Generate Recombinant Adenoviruses

Recombinant adenoviruses, PAI-Ad, SRE-Ad, RGC-Ad and CON-Ad were generated by performing homologous recombination in bacteria as described (Chartier et al. (1996) J. Virol. 70:4805-4810). The transfer plasmids were digested with AscI to obtain the fragments containing E2F-Rb under the control of pathway-responsive promoter and GFP under the control of CMV promoter flanked by Ad5 sequences. The resulting fragment was cotransformed into BJ 5183 bacterial strain with a fragment obtained by digesting PTG4609 (available from Transgene, Inc. and described in Chartier, et al. (1996) J. Virol. 70:4805-4810) with BstBI and SpeI. The resulting bacterial colonies were screened for the presence of desired recombinant Ad5 infectious plasmids, pPAI-GFP-Ad, pSRE-GFP-Ad, pRGC-GFP-Ad and pCON-GFP-Ad. These infectious plasmids were then linearized by digesting with PacI and purified by phenol-chloroform extraction and ethanol precipitatation and used for transfection of 293 cells.

Transfection was performed using Superfect (Qiagen) according to manufacturer's instructions. 2.5 µg of linearized plasmids were used for transfection of 250,000 cells grown in 6-well plates with 12 µl Superfect/well. After 8 days cytopathic effect due to virus production was observed. Cells were harvested along with the culture supernatants and subjected to three rounds of freeze-thaw cycles. Recombinant viruses in the resulting lysates were amplified by reinfecting 293 cells.

Example 6

Cell Lines

All cell lines used in this study were obtained from ATCC (Rockville, Md.) and grown as monolayer cultures maintained at 37° C. in a $CO_2$ incubator. 293, Hep3B, MRC9, A549, Panc1, U87, Caco2, MCF-7 and WIDR and were maintained in Dulbecco's modified Eagle's medium supplemented with 10% fetal bovine serum. MDA-MB 468 cells were cultured in Ham's supplemented with 10% fetal bovine serum, whereas MiaPaca-2 cells were grown in DMEM supplemented with 10% fetal bovine serum and 2.5% horse serum.

Example 7

Transfection

Cells were plated either in 6-well plates (250,000 cells/well) or in 24-well plates (62,500 cells/well) and allowed to attach overnight. Transfections were then carried out using calcium phosphate for 293 cells as described and with Superfect (Qiagen) for other cells according to manufacturer's instructions.

Example 8

Reporter/Luciferase Assays

Cells were transfected with 1.5 µg reporter plasmid and 1.0 µg of the inhibitors. 48 h post-transfection lysates were prepared by adding and incubating at room temperature for 10 min in 1× reporter lysis buffer (Promega). Luciferase activity was determined using Top Count (Packard) and an assay kit from Packard according to the instructions from Packard.

Example 9

Assays to Measure Virus-Mediated Cytopathic Effect

Cells were infected with indicated recombinant or wild-type adenoviruses and stained with 0.5% crystal violet prepared in 20% ethanol 6 days post-infection in substantial accordance with the procedure described in Bischoff, et al. (1996) Science 274:373-376.

Example 10

Construction of cU3EE and cT1LT Viruses

The MLP promoter sequence was amplified by PCR using the primers GAT CCG ATC GAT AGC GCG TAA TAT TTG TCT AGG GC (SEQ ID NO:17) and GAT CTT AAT TAA ATG GCA GTG ACC CGG AAG (SEQ ID NO:18) using Ad5 DNA such as in the plasmid pFG140 (Microbix) as the template. The MLP PCR product was then cloned at the PacI site in the plasmid pdelataE3-PCON-E2F-Rb to obtain pdelataE3-PCON-E2F-Rb-MLP. Adenovirus E3 10.5K protein coding sequence was amplified by PCR using the primers, GCG ACC CAC CCT AAC AGA (SEQ ID NO:19) and GAT CGG ATC CAA AGC GCA ACA AGG GTC A (SEQ ID NO:20) and the resulting PCR product was cloned at the Xho I site in the plasmid pCDNA3.1 (Invitrogen) to obtain pCDNA3-10.5 plasmid. Adenovirus E3 10.5K protein coding sequence was then excised from pCDNA3-10.5 by digesting with DraIII and XbaI followed by Klenow treatment and was ligated to PacI and Klenow treated pdelataE3-PCON-E2F-Rb-MLP to obtain pdelataE3-PCON-E2F-Rb-MLP-10.5K plasmid.

Recombinant adenoviruses cU3EE and cT1LT were generated by performing homologous recombination in bacteria as described (Chartier et al., 1996, J. Virol. 70:4805-4810). The transfer plasmid was digested with AscI to obtain the fragments containing E2F-Rb under the control of p53CON sequence and E310.5K under the control of MLP promoter flanked by Ad5 sequences. The resulting fragment was cotransformed into BJ 5283 bacterial strain with a fragment obtained by digesting PTG4609 (Transgene) with BstBI and SpeI. The resulting bacterial colonies were screened for the presence of desired recombinant Ad5 infectious plasmid pCEMD. The Ad5 infectious plasmid p01/CEMD was obtained by following a similar protocol but by using a derivative of PTG4609 (Transgene) in which wild-type E1A sequence was replaced with a sequence containing E1A with 01 mutation. These infectious plasmids were then linearized by digesting with PacI, purified by phenol-chloroform extraction and ethanol precipitatation and used for transfection of 293 cells.

Transfection of plasmids pCEMD and p01/CEMD was performed to generate recombinant viruses cU3EE and cT1LT respectively using Superfect (Qiagen) according to manufacturer's instructions. 2.5 µg of linearized plasmids were used for transfection of 500,000 cells grown in 6-well plates with 12 µl Superfect/well. After 8 days cytopathic effect due to virus production was observed. Cells were harvested along with the culture supernatants and subjected to three rounds of freeze-thaw cycles. Recombinant viruses in the resulting lysates were amplified by reinfecting 293 cells.

Example 11

Construction of 01/PEME

Figure 4A:
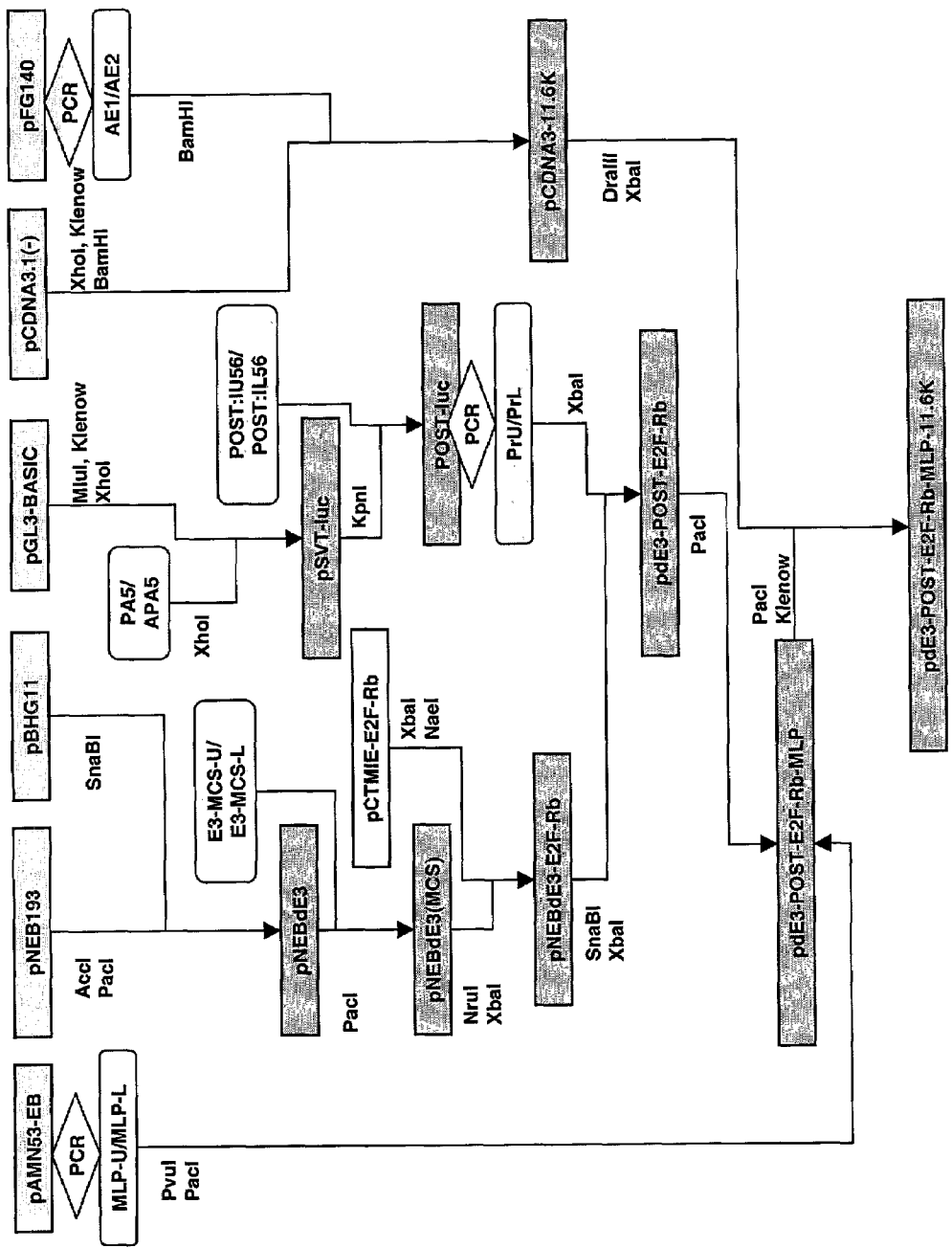
FIGS. 4A and 4B are a schematic representation of the synthesis of the vector designated 01/PEME as more fully described in Example 11 herein.
Figure 4B:
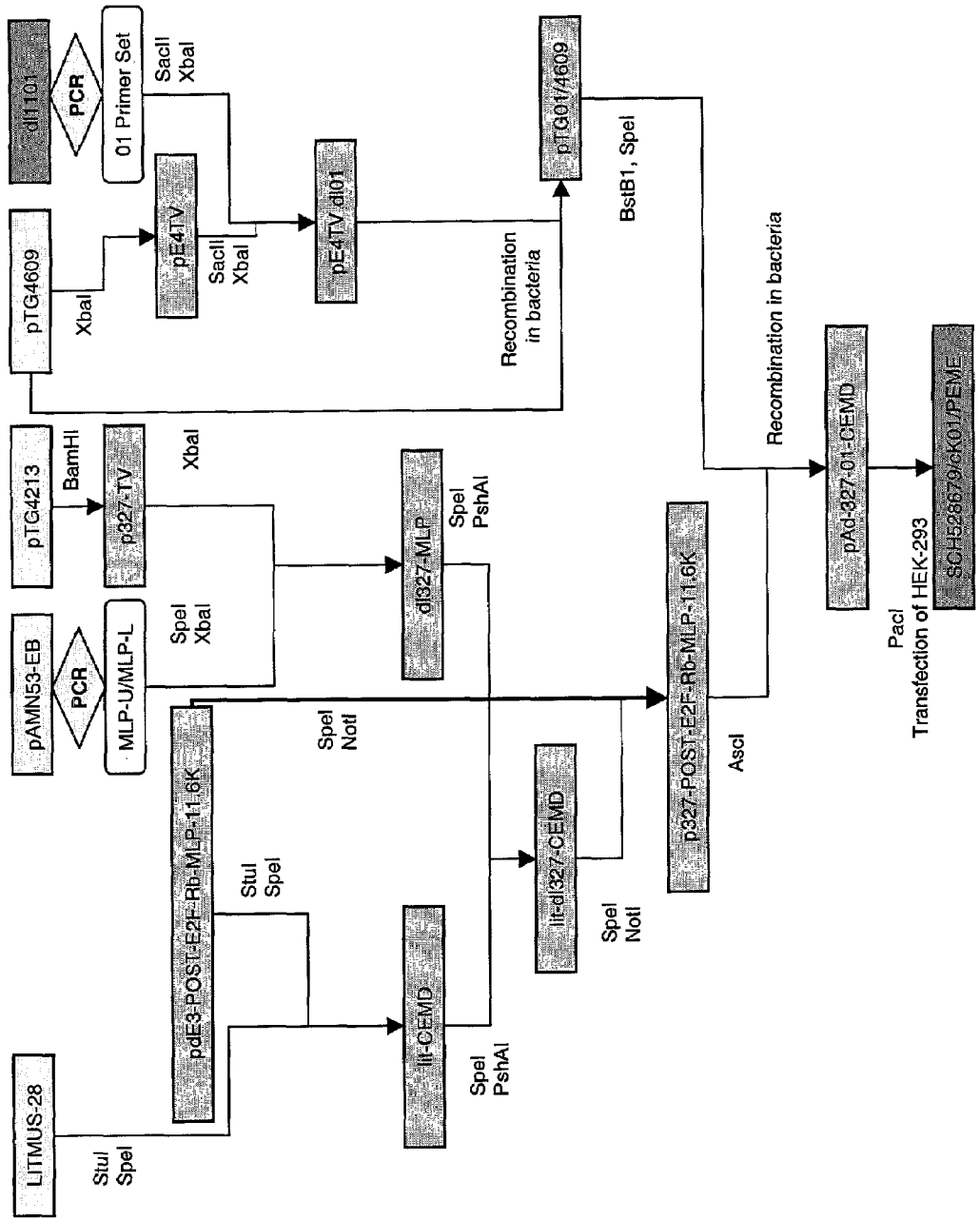

For purposes of convenience, the major features of the synthesis of 01/PEME are shown in FIGS. 4A and 4B of the attached drawings. The viral backbone was derived from the full-length adenovirus type 5 (Ad5) plasmid pTG4609 (Chartier, C. et al. J. Virol. 70, 4805-4810 (1996); U.S. Pat. No. 6,110,735 Chartier, et al. issued Aug. 29, 2000, and U.S. Pat. No. 6,281,000 Chartier, et al. issued Aug. 28, 2001, the entire teachings of which are herein incorporated by reference). E2F and retinoblastoma (Rb) coding sequences were from pCTMIE-E2F-Rb (Gregory, et al, supra), a plasmid previously constructed using pETRBc (Defeo-Jones, et al. Nature 352, 251-254. (1991)) as the source of Rb and pGEX2T-E2F-XH9 (Shan, B. et al. (1992) Mol Cell Biol 12, 5620-5631) as the source of E2F. The p53-responsive promoter was constructed using oligonucleotides encoding high affinity p53-binding sites (Funk, et al. (1992) Cell Biol 12, 2866-2871). The adenoviral major late promoter (MLP) in the E3 region was derived from Ad2.

01/PEME was constructed using standard DNA manipulation techniques as described by Sambrook et al. (Sambrook, J., Fritsch, E. F. & Maniatis, T. Molecular Cloning, Edn. 2nd. (Cold Spring Harbor Laboratory Press, 1989). Details of construction of 01/PEME are described below. All oligonucleotides were custom designed and synthesized by Ransom Hill Bioscience (Ramona, Calif.). Restriction enzymes were purchased from New England Biolabs (Beverly, Mass.). All plasmid intermediates were verified by restriction enzyme digestion. Elements inserted by PCR-based protocols were sequenced to confirm their identity. Prior to generation of the recombinant virus, a full-length recombinant infectious plasmid, pAd-327-01-CEMD, was generated by recombination in the bacterial strain BJ5183 between the transfer vector, p327-POST-E2F-Rb-MLP-11.6K and the full-length Ad5 plasmid pTG4609 (Chartier, et al. supra). The plasmid pAd-327-01-CEMD was linearized and transfected to HEK-293 cells to obtain the recombinant virus SCH 528679. The final vector has a large deletion in the E3 region which results in deletion of all E3-coding sequences except E3-12.5K and a partial deletion (dl1101 deletion) in the E1a gene that affects binding of E1a protein with the p300/CBP transcriptional co-activator (FIG. 1). Expression cassettes containing E3-11.6K controlled by a recombinant Ad2 MLP and a fusion protein containing the DNA-binding domain of E2F and the transcriptional repression domain of Rb under the control of a synthetic p53-responsive promoter are inserted in the E3 region.

A transfer plasmid containing Ad5 sequence with a 3-kb deletion in the E3 region, pNEBdE3, was constructed by cloning a 7.4 kb SnaBI fragment (26676 to 34141) from pBHG11 (Microbix, Inc. Toronto, ON) between PacI and AccI sites in pNEB193 (New England Biolabs). A multiple cloning site was introduced to the above plasmid by subcloning annealed 5-phosphorylated oligonucleotides, 5'-AAA TAC GTA ATG CAT TCT AGA GCG GCC GCT CGC GAG GAT CCT TAA T-3' (SEQ ID NO:21) (E3-MCS-U) and 5'-TAA GGA TCC TCG CGA GCG GCC GCT CTA GAA TGC ATT ACG TAT TTA T-3' (SEQ ID NO:22) (E3-MCS-L) at the PacI site of pNEBdE3 to obtain plasmid pNEBdE3 (MCS). The E2F-Rb coding sequence was introduced into the plasmid pNEBdE3 (MCS) to obtain the plasmid pNEBdE3-E2F-Rb by cloning a XbaI and NaeI fragment of pCTMIE-E2F-Rb between XbaI and NruI sites in pNEBΔE3 (MCS).

The p53-responsive promoter (PRP) was constructed by first constructing, pSVT-luc, a luciferase construct with TATA box from SV40 early promoter. To construct pSVT-luc, oligonucleotides 5'-GG TAT TTA TGA GGA GGC AGT GGC CCA CAG AGG AGC TCG AGG ATC-3' (SEQ ID NO:23) (APA5) and 5'-GAT CCT CGA GCT CCT CTG TGG GCC ACT GCC TCC TCA TAA ATA CC-3' (SEQ ID NO:24) (PA5) were annealed. The annealed product was digested with XhoI and ligated to a pGL3-BASIC (Promega, Madison, Wis.) fragment prepared by treating with MluI, followed by Klenow treatment and redigestion with XhoI to obtain pSVT-luc. Two complementary 5'-phosphorylated oligonucleotides containing consensus p53 binding sites (p53CON) (Funk, et al. (1992) Cell Biol 12:2866-2871), 5'-CT CGA CGG ACA TGC CCG GGC ATG TCC TCG ACG GAC ATG CCC GGG CAT GTC CTG TAC-3' (SEQ ID NO:25) (POST: 1U56) and 5'-AG GAC ATG CCC GGG CAT GTC CGT CGA GGA CAT GCC CGG GCA TGT CCG TCG AGG TAC-3' (SEQ ID NO:26) (POST: 1L56) were annealed. The annealed fragment was cloned at the KpnI site of pSVT-luc to obtain POST-luc plasmid.

The p53-responsive promoter containing p53 consensus site (p53CON) was introduced to the plasmid pNEBdE3-E2F-Rb by amplifying the promoter sequence by PCR using POST-luc as the template and phosphorylated primers, 5'-GTA AGG TGC CAG AAC ATT TCT C (SEQ ID NO:27) (PrU) and 5'-GAT ATC TAG ACG TCC TCT GTG GGC CAC T-3' (SEQ ID NO:28) (PrL). The resulting PCR product was digested with XbaI and ligated to SnaBI and XbaI digested pNEBdE3-E2F-Rb to obtain pdE3-POST-E2F-Rb. The MLP sequence was amplified by PCR using the primers 5'-GAT CCG ATC GAT AGC GCG TAA TAT TTG TCT AGG GC-3' (SEQ ID NO:29) (MLP-U) and 5'-GAT CTT AAT TAA ATG GCA GTG ACC CGG AAG-3' (SEQ ID NO:30) (MLP-L) using pAMN53-EB (Wills, et al. (1994) Hum Gene Ther 5, 1079-1088) as the template. The PCR product was digested with PvuI and PacI and cloned at the PacI site in the plasmid pdE3-POST-E2F-Rb to obtain pdE3-POST-E2F-Rb-MLP. Ad5 E3-11.6K protein coding sequence was amplified by PCR using the primers, 5'-GCG ACC CAC CCT AAC AGA (SEQ ID NO:31) (AE1) and 5'-GAT CGG ATC CAA AGC GCA ACA AGG GTC A-3' (SEQ ID NO:32) (AE2) using pFG140 (Microbix) as the template. E3-11.6K is also known as the adenoviral death protein (ADP) (Tollefson, et al. (1996) Virology 220: 152-162) and the size of this protein is 10.5K in Ad2. The resulting PCR product was digested with BamHI and ligated to pCDNA3.1 (−) (Invitrogen, Carlsbad, Calif.) fragment generated by digestion with XhoI followed by Klenow treatment and BamHI digestion to obtain pCDNA3-11.6K. The E3-11.6K coding sequence was then excised from pCDNA3-11.6K by digesting with DraIII and XbaI followed by Klenow treatment and ligated to PacI and Klenow treated pdE3-POST-E2F-Rb-MLP to obtain pdE3-POST-E2F-Rb-MLP-11.6K plasmid.

An intermediate vector p327TV with an E3 deletion as in dl327 (Jones, N. & Shenk, T. (1979) Proc. Natl. Acad. Sci. USA 76, 3665-3669) was first constructed by re-ligating a BamHI fragment of pTG4213 (Chartier, et al. supra). The Ad2 MLP promoter sequence was amplified by PCR from pAMN53, digested with SpeI and XbaI and inserted at the XbaI site to obtain dl327-MLP. Another intermediate vector, lit-CEMD was constructed by subcloning the StuI to SpeI fragment from pdE3-POST-E2F-Rb-MLP-11.6K between StuI and SpeI site of LITMUS-28 (New England Biolabs). The dl327 backbone from dl327-MLP was transferred to lit-CEMD by substituting SpeI to PshAI fragment in lit-CEMD with SpeI to PshAI fragment from dl327-MLP to generate lit-dl327-CEMD. Finally, the SpeI to NotI fragment in pdE3-POST-E2F-Rb-MLP-11.6K was replaced with SpeI to NotI fragment from lit-dl327-CEMD to obtain p327-POST-E2F-Rb-MLP-11.6K.

The transfer plasmid p327-POST-E2F-Rb-MLP-11.6K was digested with AscI to generate fragments containing E2F-Rb under the control of the previously described p53-responsive promoter and E3-11.6K under the control of Ad2 MLP flanked by Ad5 sequences. The resulting E3 expression cassette was co-transformed into the BJ5183 bacterial strain (Chartier, et al. supra) with a fragment obtained by digesting a variant of pTG4609 (FIG. 3) in which the wild-type E1a sequence was replaced with a sequence containing E1a with the dl1101 deletion (Chartier, et al. supra) via BstBI and SpeI (i.e., pTG01/4609). Bacterial colonies were screened for the presence of desired recombinant adenovirus infectious plasmid pAd-327-01-CEMD. The sequence of pAd-327-01-CEMD was verified by restriction analysis, partial DNA sequencing, and PCR. The infectious plasmid, pAd-327-01-CEMD, was then linearized with PacI, subjected to phenol-chloroform extraction and ethanol precipitation, and used for transfection of HEK-293 cells.

For generation of virus, $2.5 \times 10^5$ HEK-293 cells grown in each well of a 6-well plate were transfected with 2.5 µg of linearized plasmid using 12 µL Superfect (Qiagen)/well. After 8-15 days cytopathic effect due to virus production was observed. Cells were harvested along with the culture supernatants and subjected to three freeze-thaw cycles. Recombinant virus in resulting lysates were amplified by re-infecting 293 cells. Viruses were purified in substantial accordance with the teaching of Huyghe, et al. (1995) Hum. Gene Ther. 6, 1403-1416 and Shabram, et al., U.S. Pat. No. 5,837,520 Shabram, et al. issued Nov. 17, 1998 (the entire teaching of which is herein incorporated by reference), and quantified by chromatographic methods (Shabram, P. (1997) Hum. Gene Ther. 8, 453-465).

The cell line used for the production of 01/PEME was the human lung carcinoma cell line, A549, obtained from the American Type Culture Collection (ATCC cat. no. CCL-185). This cell line was developed in 1972 through explant culture of human lung carcinomatous tissue from a patient (Lieber, M. et al., (1976) Int. J. Cancer 17, 62-70). This cell line supports the replication of many viruses including wild-type adenovirus, but does not support the replication of E1-deleted recombinant adenovirus vectors.

The manufacturing process for 01/PEME includes steps for propagating A549 cells from the WCB in T-flasks and cell factories as the inoculum for culture in a bioreactor ranging in size from 1 liter to 2,000 liters. Techniques for the large scale production of adenovirus are well known in the scientific and patent literature. The seed for the production bioreactor originates either from T-flasks, multiple cell factories or from a seed bioreactor. Within the bioreactors, the cells are grown on the surface of microcarriers in liquid medium containing fetal bovine serum. When a suitable cell density has been achieved, cells are infected with the MVB. After intracellular proliferation of the adenovirus, viral particles are recovered from the cells in a series of cell separation and disruption steps followed by clarification, concentration, and filtration. The resulting crude viral concentrate is stored frozen at −20° C. or below.

A purification batch starts with crude viral concentrate originating from a fraction or the entirety of a single bioreactor run. The 01/PEME product is purified by anion exchange chromatography followed by zinc-charged metal affinity chromatography to remove impurities such as host cell proteins and DNA. The final step involves a 0.2-µm filtration of the bulk drug substance. The purified bulk 01/PEME is stored in solution refrigerated at 2-8° C. or frozen at −20° C. or below.

We claim:

1. A selectively replicating recombinant adenoviral vector comprising a p53 pathway-responsive promoter operably linked to a repressor of viral replication, wherein the promoter is activated by the presence of functional p53, wherein:
   the vector selectively replicates in neoplastic cells possessing a defect in the pathway to which the promoter is responsive;
   the repressor of viral replication is an E2F-Rb fusion protein;
   the vector comprises a deletion in an E3 region; and
   the vector comprises an expression cassette comprising a major late promoter (MLP) operably linked to a nucleic acid encoding an adenovirus E3-11.6K protein.

2. The vector of claim 1 wherein the p53 pathway responsive promoter is p53CON.

3. The vector of claim 1 further comprising a deletion in the adenoviral E1a coding region so as to eliminate p300 binding.

4. The vector of claim 3 wherein the deletion in the adenoviral E1a coding region comprises a deletion of amino acids 4-25 of the E1a 289R and 243R proteins.

5. The vector of claim 1, wherein the neoplastic cells are tumor cells.

6. A pharmaceutical formulation comprising a selectively replicating recombinant adenoviral vector comprising a p513 pathway-responsive promoter operably linked to a repressor of viral replication and a pharmaceutically acceptable carrier, wherein the promoter is activated by the presence of functional p53, wherein:
   the vector selectively replicates in neoplastic cells possessing a defect in the pathway to which the promoter is responsive,
   the repressor of viral replication is an E2F-Rb fusion protein;
   the vector comprises a deletion in an E3 region; and
   the vector comprises an expression cassette comprising a major late promoter (MLP) operably linked to a nucleic acid encoding an adenovirus 1E3-11.6K protein.

7. The formulation of claim 6 wherein the p53 pathway responsive promoter is p53CON.

8. The formulation of claim 6 wherein the vector further comprises a deletion in the adenoviral E1a coding region so as to eliminate p300 binding.

9. The formulation of claim 8 wherein the deletion in the adenoviral E1a coding region comprises a deletion of amino acids 4-25 of the E1a 289R and 243R proteins.

10. The formulation of claim 6, further comprising a delivery enhancing agent.

11. The formulation of claim 10 wherein the delivery enhancing agent is selected from the group consisting of detergents, alcohols, and surfactants.

12. The formulation of claim 6, wherein the neoplastic cells are tumor cells.

13. An isolated cell transformed with a selectively replicating recombinant adenoviral vector comprising a p53-responsive promoter operably linked to a repressor of viral replication, wherein the promoter is activated by the presence of functional p53, wherein:
   the vector selectively replicates in neoplastic cells possessing a defect in the pathway to which the promoter is responsive;
   the repressor of viral replication is an E2F-Rb fusion protein;
   the vector comprises a deletion in an E3 region; and
   the vector comprises an expression cassette comprising a major late promoter (MLP) operably linked to a nucleic acid encoding an adenovirus E3-11.6K protein.

14. The cell of claim 13 wherein the vector further comprises a deletion in the adenoviral E1a coding region so as to eliminate p300 binding.

15. The cell of claim 14 wherein the deletion in the adenoviral E1a coding region comprises a deletion of amino acids 4-25 of the E1a 289R and 243R proteins.

16. The cell of claim 13 wherein the cell is a tumor cell.

* * * * *

UNITED STATES PATENT AND TRADEMARK OFFICE
CERTIFICATE OF CORRECTION

PATENT NO.        : 7,691,370 B2
APPLICATION NO.   : 10/062216
DATED             : April 6, 2010
INVENTOR(S)       : Ramachandra et al.

It is certified that error appears in the above-identified patent and that said Letters Patent is hereby corrected as shown below:

Title page, item [54] and col. 1, line 5 title, please delete the word "Vector" and insert --Vectors--.

In claim 6, column 55, line 57, delete "p513" and insert --p53--.

In claim 6, column 56, line 34, delete "1E3-11.6K" and insert --E3-11.6K--.

Signed and Sealed this

Eighth Day of June, 2010

David J. Kappos
*Director of the United States Patent and Trademark Office*

SEQUENCE LISTING

<160> NUMBER OF SEQ ID NOS: 32

<210> SEQ ID NO 1
<211> LENGTH: 24
<212> TYPE: DNA
<213> ORGANISM: Artificial Sequence
<220> FEATURE:
<223> OTHER INFORMATION: 749 bp fragment PCR amplification primer

<400> SEQUENCE: 1
agtcgagctc caacctcagc caga                                    24

<210> SEQ ID NO 2
<211> LENGTH: 44
<212> TYPE: DNA
<213> ORGANISM: Artificial Sequence
<220> FEATURE:
<223> OTHER INFORMATION: 749 bp fragment PCR amplification primer
      containing SV40 TATA box

<400> SEQUENCE: 2
gatcctcgag ctcctctgtg ggccactgcc tcctcataaa tacc               44

<210> SEQ ID NO 3
<211> LENGTH: 44
<212> TYPE: DNA
<213> ORGANISM: Artificial Sequence
<220> FEATURE:
<223> OTHER INFORMATION: annealed oligonucleotide

<400> SEQUENCE: 3
ggtatttatg aggaggcagt ggcccacaga ggagctcgag gatc               44

<210> SEQ ID NO 4
<211> LENGTH: 44
<212> TYPE: DNA
<213> ORGANISM: Artificial Sequence
<220> FEATURE:
<223> OTHER INFORMATION: annealed oligonucleotide

<400> SEQUENCE: 4
gatcctcgag ctcctctgtg ggccactgcc tcctcataaa tacc               44

<210> SEQ ID NO 5
<211> LENGTH: 38
<212> TYPE: DNA
<213> ORGANISM: Artificial Sequence
<220> FEATURE:
<223> OTHER INFORMATION: annealed oligonucleotide containing Smad4/DPC4
      binding sites

<400> SEQUENCE: 5
cgtctagacg tctagacgtc tagacgtcta gactgtac                     38

<210> SEQ ID NO 6
<211> LENGTH: 38
<212> TYPE: DNA
<213> ORGANISM: Artificial Sequence
<220> FEATURE:
<223> OTHER INFORMATION: annealed oligonucleotide containing Smad4/DPC4
      binding sites

<400> SEQUENCE: 6
agtctagacg tctagacgtc tagacgtcta gacggtac                     38

<210> SEQ ID NO 7
<211> LENGTH: 41
<212> TYPE: DNA
<213> ORGANISM: Artificial Sequence
<220> FEATURE:
<223> OTHER INFORMATION: annealed complimentary 5'-phosphorylated
      oligonucleotide containing p53 binding sites from
      ribosomal gene cluster

<400> SEQUENCE: 7
agaaaaggca aggccaggca agtccaggca actcgtggta c                    41

<210> SEQ ID NO 8
<211> LENGTH: 41
<212> TYPE: DNA
<213> ORGANISM: Artificial Sequence
<220> FEATURE:
<223> OTHER INFORMATION: annealed complimentary 5'-phosphorylated
      oligonucleotide containing p53 binding sites from
      ribosomal gene cluster

<400> SEQUENCE: 8
cacgagttgc ctggacttgc ctggccttgc cttttctgta c                    41

<210> SEQ ID NO 9
<211> LENGTH: 56
<212> TYPE: DNA
<213> ORGANISM: Artificial Sequence
<220> FEATURE:
<223> OTHER INFORMATION: annealed complimentary 5'-phosphorylated
      oligonucleotide containing consensus p53 binding
      sites (p53CON)

<400> SEQUENCE: 9
ctcgacggac atgcccgggc atgtcctcga cggacatgcc cgggcatgtc ctgtac     56

<210> SEQ ID NO 10
<211> LENGTH: 56
<212> TYPE: DNA
<213> ORGANISM: Artificial Sequence
<220> FEATURE:
<223> OTHER INFORMATION: annealed complimentary 5'-phosphorylated
      oligonucleotide containing consensus p53 binding
      sites (p53CON)

<400> SEQUENCE: 10
aggacatgcc cgggcatgtc cgtcgaggac atgcccgggc atgtccgtcg aggtac     56

<210> SEQ ID NO 11
<211> LENGTH: 46
<212> TYPE: DNA
<213> ORGANISM: Artificial Sequence
<220> FEATURE:
<223> OTHER INFORMATION: annealed complimentary 5'-phosphorylated
      oligonucleotide introducing multiple cloning site
      into transfer plasmid

<400> SEQUENCE: 11
aaatacgtaa tgcattctag agcggccgct cgcgaggatc cttaat               46

<210> SEQ ID NO 12
<211> LENGTH: 46
<212> TYPE: DNA
<213> ORGANISM: Artificial Sequence
<220> FEATURE:
<223> OTHER INFORMATION: annealed complimentary 5'-phosphorylated
      oligonucleotide introducing multiple cloning site
      into transfer plasmid -continued

```
<400> SEQUENCE: 12
taaggatcct cgcgagcggc cgctctagaa tgcattacgt atttat          46

<210> SEQ ID NO 13
<211> LENGTH: 22
<212> TYPE: DNA
<213> ORGANISM: Artificial Sequence
<220> FEATURE:
<223> OTHER INFORMATION: 5'-phosphorylated PCR amplification primer
      introducing TGF-beta-responsive promoter
      containing SRE into transfer plasmid

<400> SEQUENCE: 13
gtaaggtgcc agaacatttc tc                                    22

<210> SEQ ID NO 14
<211> LENGTH: 28
<212> TYPE: DNA
<213> ORGANISM: Artificial Sequence
<220> FEATURE:
<223> OTHER INFORMATION: 5'-phosphorylated PCR amplification primer
      introducing TGF-beta-responsive promoter
      containing SRE into transfer plasmid

<400> SEQUENCE: 14
gataactagt gctcctctgt gggccact                              28

<210> SEQ ID NO 15
<211> LENGTH: 22
<212> TYPE: DNA
<213> ORGANISM: Artificial Sequence
<220> FEATURE:
<223> OTHER INFORMATION: 5'-phosphorylated PCR amplification primer for
      p53-responsive promoters

<400> SEQUENCE: 15
gtaaggtgcc agaacatttc tc                                    22

<210> SEQ ID NO 16
<211> LENGTH: 28
<212> TYPE: DNA
<213> ORGANISM: Artificial Sequence
<220> FEATURE:
<223> OTHER INFORMATION: 5'-phosphorylated PCR amplification primer for
      p53-responsive promoters

<400> SEQUENCE: 16
gatatctaga cgtcctctgt gggccact                              28

<210> SEQ ID NO 17
<211> LENGTH: 35
<212> TYPE: DNA
<213> ORGANISM: Artificial Sequence
<220> FEATURE:
<223> OTHER INFORMATION: PCR amplification primer for MLP promoter
      sequence

<400> SEQUENCE: 17
gatccgatcg atagcgcgta atatttgtct agggc                      35

<210> SEQ ID NO 18
<211> LENGTH: 30
<212> TYPE: DNA
<213> ORGANISM: Artificial Sequence
<220> FEATURE:
<223> OTHER INFORMATION: PCR amplification primer for MLP promoter
``` sequence

<400> SEQUENCE: 18
gatcttaatt aaatggcagt gacccggaag                               30

<210> SEQ ID NO 19
<211> LENGTH: 18
<212> TYPE: DNA
<213> ORGANISM: Artificial Sequence
<220> FEATURE:
<223> OTHER INFORMATION: PCR amplification primer for Adenovirus E3
      10.5K protein coding sequence

<400> SEQUENCE: 19
gcgacccacc ctaacaga                                            18

<210> SEQ ID NO 20
<211> LENGTH: 28
<212> TYPE: DNA
<213> ORGANISM: Artificial Sequence
<220> FEATURE:
<223> OTHER INFORMATION: PCR amplification primer for Adenovirus E3
      10.5K protein coding sequence

<400> SEQUENCE: 20
gatcggatcc aaagcgcaac aagggtca                                 28

<210> SEQ ID NO 21
<211> LENGTH: 46
<212> TYPE: DNA
<213> ORGANISM: Artificial Sequence
<220> FEATURE:
<223> OTHER INFORMATION: annealed 5'-phosphorylated E3-MCS-U
      oligonucleotide for introducing multiple cloning
      site into transfer plasmid

<400> SEQUENCE: 21
aaatacgtaa tgcattctag agcggccgct cgcgaggatc cttaat             46

<210> SEQ ID NO 22
<211> LENGTH: 46
<212> TYPE: DNA
<213> ORGANISM: Artificial Sequence
<220> FEATURE:
<223> OTHER INFORMATION: annealed 5'-phosphorylated E3-MCS-L
      oligonucleotide for introducing multiple cloning
      site into transfer plasmid

<400> SEQUENCE: 22
taaggatcct cgcgagcggc cgctctagaa tgcattacgt atttat             46

<210> SEQ ID NO 23
<211> LENGTH: 44
<212> TYPE: DNA
<213> ORGANISM: Artificial Sequence
<220> FEATURE:
<223> OTHER INFORMATION: APA5 annealed oligonucleotide for construct
      pSVT-luc

<400> SEQUENCE: 23
ggtatttatg aggaggcagt ggcccacaga ggagctcgag gatc               44

<210> SEQ ID NO 24
<211> LENGTH: 44
<212> TYPE: DNA
<213> ORGANISM: Artificial Sequence
<220> FEATURE:

```
<223> OTHER INFORMATION: PA5 annealed oligonucleotide for construct
      pSVT-luc

<400> SEQUENCE: 24
gatcctcgag ctcctctgtg ggccactgcc tcctcataaa tacc                    44

<210> SEQ ID NO 25
<211> LENGTH: 56
<212> TYPE: DNA
<213> ORGANISM: Artificial Sequence
<220> FEATURE:
<223> OTHER INFORMATION: annealed complimentary 5'-phosphorylated
      oligonucleotide POST:1U56 containing consensus p53
      binding sites (p53CON)

<400> SEQUENCE: 25
ctcgacggac atgcccgggc atgtcctcga cggacatgcc cgggcatgtc ctgtac       56

<210> SEQ ID NO 26
<211> LENGTH: 56
<212> TYPE: DNA
<213> ORGANISM: Artificial Sequence
<220> FEATURE:
<223> OTHER INFORMATION: annealed complimentary 5'-phosphorylated
      oligonucleotide POST:1L56 containing consensus p53
      binding sites (p53CON)

<400> SEQUENCE: 26
aggacatgcc cgggcatgtc cgtcgaggac atgcccgggc atgtccgtcg aggtac       56

<210> SEQ ID NO 27
<211> LENGTH: 22
<212> TYPE: DNA
<213> ORGANISM: Artificial Sequence
<220> FEATURE:
<223> OTHER INFORMATION: 5'-phosphorylated PCR amplification primer PrU
      for introducing consensus p53 binding sites (p53CON)
      into plasmid pNEBdE3-E2F-Rb

<400> SEQUENCE: 27
gtaaggtgcc agaacatttc tc                                            22

<210> SEQ ID NO 28
<211> LENGTH: 28
<212> TYPE: DNA
<213> ORGANISM: Artificial Sequence
<220> FEATURE:
<223> OTHER INFORMATION: 5'-phosphorylated PCR amplification primer PrL
      for introducing consensus p53 binding sites (p53CON)
      into plasmid pNEBdE3-E2F-Rb

<400> SEQUENCE: 28
gatatctaga cgtcctctgt gggccact                                      28

<210> SEQ ID NO 29
<211> LENGTH: 35
<212> TYPE: DNA
<213> ORGANISM: Artificial Sequence
<220> FEATURE:
<223> OTHER INFORMATION: MLP-U PCR amplification primer for MLP sequence

<400> SEQUENCE: 29
gatccgatcg atagcgcgta atatttgtct agggc                              35

<210> SEQ ID NO 30
<211> LENGTH: 30
<212> TYPE: DNA
```

```
<213> ORGANISM: Artificial Sequence
<220> FEATURE:
<223> OTHER INFORMATION: MLP-L PCR amplification primer for MLP sequence

<400> SEQUENCE: 30
gatcttaatt aaatggcagt gacccggaag                                       30

<210> SEQ ID NO 31
<211> LENGTH: 18
<212> TYPE: DNA
<213> ORGANISM: Artificial Sequence
<220> FEATURE:
<223> OTHER INFORMATION: AE1 PCR amplification primer for Ad5 E3-11.6K
      protein coding sequence

<400> SEQUENCE: 31
gcgacccacc ctaacaga                                                    18

<210> SEQ ID NO 32
<211> LENGTH: 28
<212> TYPE: DNA
<213> ORGANISM: Artificial Sequence
<220> FEATURE:
<223> OTHER INFORMATION: AE2 PCR amplification primer for Ad5 E3-11.6K
      protein coding sequence

<400> SEQUENCE: 32
gatcggatcc aaagcgcaac aagggtca                                         28
```